US008101727B2

(12) United States Patent
Stover et al.

(10) Patent No.: US 8,101,727 B2
(45) Date of Patent: Jan. 24, 2012

(54) COMPOSITIONS AND METHODS OF USE FOR ANTIBODIES OF C-MET

(75) Inventors: David Raymond Stover, Lexington, MA (US); Josef Prassler, Germering (DE); Catrin Berger, Germering (DE); Bodo Brocks, Gilching (DE)

(73) Assignee: Novartis AG, Basel (CH)

( * ) Notice: Subject to any disclaimer, the term of this patent is extended or adjusted under 35 U.S.C. 154(b) by 302 days.

(21) Appl. No.: 12/295,535

(22) PCT Filed: Mar. 29, 2007

(86) PCT No.: PCT/US2007/007543
§ 371 (c)(1),
(2), (4) Date: Sep. 30, 2008

(87) PCT Pub. No.: WO2007/126799
PCT Pub. Date: Nov. 8, 2007

(65) Prior Publication Data
US 2009/0175860 A1    Jul. 9, 2009

Related U.S. Application Data

(60) Provisional application No. 60/787,556, filed on Mar. 30, 2006.

(51) Int. Cl.
*C07K 16/28* (2006.01)
*C07K 16/00* (2006.01)
*A61K 39/395* (2006.01)

(52) U.S. Cl. ............. 530/388.22; 530/387.1; 530/387.3; 530/388.1; 424/130.1; 424/133.1; 424/135.1; 424/141.1; 424/143.1; 435/810

(58) Field of Classification Search .................. None
See application file for complete search history.

(56) References Cited

U.S. PATENT DOCUMENTS

| 5,646,036 | A  | 7/1997  | Schwall et al. |
| 5,686,292 | A  | 11/1997 | Schwall et al. |
| 6,207,152 | B1 | 3/2001  | Schwall et al. |
| 6,468,529 | B1 | 10/2002 | Schwall et al. |
| 7,498,420 | B2 | 3/2009  | Michaud et al. |

FOREIGN PATENT DOCUMENTS

| EP | 0520158 A1    | 12/1992 |
| EP | 1 746 160 A2  | 1/2007  |
| WO | 9220792 A1    | 11/1992 |
| WO | 9406909 A2    | 3/1994  |
| WO | 9638557 A1    | 12/1996 |
| WO | WO2005/016382 A1 | 2/2005 |

OTHER PUBLICATIONS

Rudikoff et al. (Proc Natl Acad Sci USA 1982 vol. 79 p. 1979.*
MacCallum et al. J. Mol. Biol. (1996) 262, 732-745.*
Pascalis et al. (The Journal of Immunology (2002) 169, 3076-3084.*
Casset et al. (BBRC 2003, 307:198-205.*
Vajdos et al. (J. Mol. Biol. (2002) 320, 415-428.*
Chen et al. (J. Mol. Bio. (1999) 293, 865-881.*
Wu et al. (J. Mol. Biol. (1999) 294, 151-162.*
Padlan et al. (PNAS 1989, 86:5938-5942.*
Lamminmaki et al. (JBC 2001, 276:36687-36694.*
The Merck Manuals Online Medical Library, [online]. Whitehouse Station, NJ: Merck Research Laboratories, 2006-2007. [retrieved on Nov. 19, 2007]. Retrieved from the Internet: < URL: http://www.merckmanuals.com/professional/sec18/ch253/ch253e.html>. Breast Cancer. see pp. 1-8.*
Gonzatti-Haces et al., "Characterization of the TPR-MET Oncogene p65 and the MET Protooncogene p140 Protein-tyrosine Kinases", Biochemistry, 1988 vol. 85 pp. 21-25.
Faletto et al., "Evidence for non-covalent clusters of the c-met proto-oncogene product," Oncogene 7:1149-1157 (1992).
Mark et al., "Expression and Characterization of Hepatocyte Growth Factor Receptor-IgG Fusion Proteins," The Journal of Biological Chemistry 267:26166-26171 (Dec. 25, 1992).
Park et al., "Sequence of MET protooncogene cDNA has features characteristic of the tyrosine kinase family of growth-factor receptors," Proc. Natl. Acad. Sci. USA 84:6379-6383 (Sep. 1987).
Prat et al., "C-Terminal Truncated Forms of Met, the Hepatocyte Growth Factor Receptor," Molecular and Cellular Biology 11(12):5954-5962 (Dec. 1991).
Prat et at, "The Receptor Encoded by the Human c-Met Oncogene is Expressed in Hepatocytes, Epithelial Cells and Solid Tumors," Int. J. Cancer 49:323-328 (1991).
Rong et al., "Tumorigenicity of the met Proto-Oncogene and the Gene for Hepatocyte Growth Factor," Molecular and Cellular Biology 12(11):5152-5158 (Nov. 1992).
Bauer et al.; "Targeting of Urokinase Plasminogen Activator Receptor in Human Pancreatic Carcinoma Cells Inhibits c-Met- and Insulin-like Growth Factor-I Receptor-Mediated Migration and Invasion and Orthotopic Tumor Growth in Mice"; Cancer Res; 65(17):7775-7781 (2005).
Burgess et al.; "Fully Human Monoclonal Antibodies to Hepatocyte Growth Factor with Therapeutic Potential against Hepatocyte Growth Factor/c-Met-Dependent Human Tumors"; Cancer Res; 66(3)1721-1729 (2006).
Christensen et al.; "A Selective Small Molecule Inhibitor of c-Met Kinase Inhibits c-Met-Dependent Phenotypes in Vitro and Exhibits Cytoreductive Antitumor Activity in Vivo"; Cancer Res; 63:7345-7355 (2003).
Eckerich et al.; "Hypoxia can induce c-Met expression in glioma cells and enhance SF/HGF-induced cell migration"; Int. J. Cancer; 121:276-283 (2007).
Goetsch et al.; "Abstract B127: Single or combined in vivo therapies of cancer with h224G11, a humanized antibody targeting the c-Met receptor"; Molecular Cancer Therapeutics; 8(12)(Suppl. 1) (2009)[Abstract].
Graveel et al.; "Activating Met mutations produce unique tumor profiles in mice with selective duplication of the mutant allele"; PNAS; 101(49):17198-17203 (2004).

(Continued)

*Primary Examiner* — Sharon Wen
(74) *Attorney, Agent, or Firm* — Kristin Konzak

(57) ABSTRACT

Antibodies and fragments that bind to the protein target c-Met, particularly to epitopes located in the c-Met extracellular domain, are provided, as are methods of use of the antibodies and kits, for treating an unwanted cell, in particular, a cell associated with a c-Met-related condition such as a cancer, a metastasis, or an inflammatory condition.

31 Claims, 5 Drawing Sheets

OTHER PUBLICATIONS

Graveel et al.; "Activating Met mutations produce unique tumor profiles in mice with selective duplication of the mutant allele"; PNAS; 101(49):17198-17203 (2004)[Supporting Information].

Kraus-Berthier et al.; "Histology and Sensitivity to Anticancer Drugs of Two Human Non-Small Cell Lung Carcinomas Implanted in the Pleural Cavity of Nude Mice"; Clin Cancer Res; 6:297-304 (2000).

Ma et al.; "A Selective Small Molecule c-MET Inhibitor, PHA665752, Cooperates with Rapamycin"; Clin Cancer Res; 11:2312-2319 (2005).

Martens et al.; "A Novel One-Armed Anti-c-Met Antibody Inhibits Glioblastoma Growth in vivo"; Clin Cancer Res; 12 (20):6144-6152 (2006).

Nguyen et al.; "Improved gene transfer selectivity to hepatocarcinoma cells by retrovirus vector displaying single-chain variable fragment antibody against c-Met"; Cancer Gene Therapy; 10:840-849 (2003).

Ohashi et al.; "Sustained survival of human hepatocytes in mice: a model for in vivo infection with human hepatitis B and hepatitis delta viruses"; Nature Medicine; 6(3):327-331 (2000).

Prat et al.; "Agonistic monoclonal antibodies against the Met receptor dissect the biological responses to HGF"; Journal of Cell Science; 111:237-247 (1998).

Zou et al.; "An Orally Available Small-Molecule Inhibitor of c-Met, PF-2341066, Exhibits Cytoreductive Antitumor Efficacy through Antiproliferative and Antiangiogenic Mechanisms"; Cancer Res; 67(9):4408-4417 (2007).

Zou et al.; "An Orally Available Small-Molecule Inhibitor of c-Met, PF-2341066, Exhibits Cytoreductive Antitumor Efficacy through Antiproliferative and Antiangiogenic Mechanisms"; Cancer Res; 67(9):4408-4417 (2007) [Supplemental Tables and Figures].

* cited by examiner

VH

| SEQ ID NO: | Position | Framework 1 / CDR 1 |
|---|---|---|
| | | 1........2........3 |
| | | 1 2 3 4 5 6 7 8 9 0 1 2 3 4 5 6 7 8 9 0 1 2 3 4 5 6 7 8 9 0 1 a b 2 3 4 5 |
| | | MfeI                                    BspEI |
| 97 | VH1A | Q V Q L V Q S G A E V K K P G S S V K V S C K A S |
| 58 | 4687 | Q V Q L V Q S G A E V K K P G S S V K V S C K A S |
| 59 | 5081 | Q V Q L V Q S G A E V K K P G S S V K V S C K A S |
| 60 | 5082 | Q V Q L V Q S G A E V K K P G S S V K V S C K A S |
| 98 | VH1B | Q V Q L V Q S G A E V K K P G A S V K V S C K A S |
| 65 | 4536 | Q V Q L V Q S G A E V K K P G A S V K V S C K A S |
| 69 | 5078 | Q V Q L V Q S G A E V K K P G A S V K V S C K A S |
| 57 | 5079 | Q V Q L V Q S G A E V K K P G A S V K V S C K A S |
| 99 | VH4 | Q V Q L Q E S G P G L V K P G E T L S L T C T V S |
| 61 | 4541 | Q V Q L Q E S G P G L V K P G E T L S L T C T V S |
| 100 | VH5 | Q V Q L V Q S G A E V K K P G E S L K I S C K G S |
| 62 | 4537 | Q V Q L V Q S G A E V K K P G E S L K I S C K G S |
| 64 | 4682 | Q V Q L V Q S G A E V K K P G E S L K I S C K G S |
| 101 | VH6 | Q V Q L Q Q S G P G L V K P S Q T L S L T C A I S |
| 63 | 4690 | Q V Q L Q Q S G P G L V K P S Q T L S L T C A I S |

Framework 2 / CDR 2

```
            4              5                6                  7
 6 7 8 9 0 1 2 3 4 5 6 7 8 9 0 1 2 a b c 3 4 5 6 7 8 9 0 1 2 3 4 5 6 7 8 9 0 1 2 3 4 5 6
         BstXI     XhoI                                    BstEII         BstBI

V Lambda

| SEQ ID NO: | Position | Framework 1 | CDR 1 |
|---|---|---|---|
| | | 1...10...20 (EcoRV ... SexA ... BssSI) | 30 a b c d e f 1 2 3 4 |
| 102 | VL1 | D EVLTQPP-SVSGAPGQRVTISC | SGSSNIGS......NYVS |
| 50 | 4682 | D EVLTQPP-SVSGAPGQRVTISC | SGSSNIGS......NYVV |
| 103 | VL3 | D ELTQPP-SVSVAPGQTARISC | SGDALGD......YYAS |
| 31 | 4536 | D ELTQPP-SVSVAPGQTARISC | SGDSIGN......KYVH |
| 51 | 5087 | D ELTQPP-SVSVAPGQTARISC | SGDSIGN......KYVH |
| 33 | 5088 | D ELTQPP-SVSVAPGQTARISC | SGDSIGN......YYVH |
| 52 | 5091 | D ELTQPP-SVSVAPGQTARISC | SGDSIGN......KYVH |
| 35 | 5092 | D ELTQPP-SVSVAPGQTARISC | SGDSIGN......KYVH |
| 45 | 4537 | D ELTQPP-SVSVAPGQTARISC | SGDSLRS......YFVS |
| 46 | 5102 | D ELTQPP-SVSVAPGQTARISC | SGDSLRS......YFVS |
| 47 | 5105 | D ELTQPP-SVSVAPGQTARISC | SGDSLRS......YFVS |
| 41 | 4541 | D ELTQPP-SVSVAPGQTARISC | SGDNIGS......YYVV |
| 42 | 5093 | D ELTQPP SVSVAPGQTARISC | SGDNIGS......YFVV |
| 43 | 5094 | D ELTQPP SVSVAPGQTARISC | SGDNIGS......YFVV |
| 44 | 5095 | D ELTQPP SVSVAPGQTARISC | SGDNIGS......YFVV |
| 48 | 4690 | D ELTQPP-SVSVAPGQTARISC | SGDKLGS......YFVV |
| 49 | 5106 | D ELTQPP SVSVAPGQTARISC | SGDKLGS......YFVV |

| CDR 2 | Framework 3 |
|---|---|
| (50...) | 60...70...80 (Bsu36I ... BamHI ... BbsI) |
| NNQRPS | G VPDRFS G S KSGTSASLAITGLQS E D EADYYC |
| DNNKRPS | G VPDRFS G S KSGTSASLAITGLQS E D EADYYC |
| DNDKRPS | G IPERFS G S NSGNTATLTISGTQA E D EADYYC |
| ADSDRPS | G IPERFS G S NSGNTATLTISGTQA E D EADYYC |
| ADSDRPS | G IPERFS G S NSGNTATLTISGTQA E D EADYYC |
| ADSDRPS | G IPERFS G S NSGNTATLTISGTQA E D EADYYC |
| ADSDRPS | G IPERFS G S NSGNTATLTISGTQA E D EADYYC |
| DDSDRPS | G IPERFS G S NSGNTATLTISGTQA E D EADYYC |
| DDSDRPS | G IPERFS G S NSGNTATLTISGTQA E D EADYYC |
| DDSDRPS | G IPERFS G S NSGNTATLTISGTQA E D EADYYC |
| DDNKRPS | G IPERFS G S NSGNTATLTISGTQA E D EADYYC |
| DDNKRPS | G IPERFS G S NSGNTATLTISGTQA E D EADYYC |
| DDNKRPS | G IPERFS G S NSGNTATLTISGTQA E D EADYYC |
| DDNKRPS | G IPERFS G S NSGNTATLTISGTQA E D EADYYC |
| DDNKRPS | G IPERFS G S NSGNTATLTISGTQA E D EADYYC |
| DDNKRPS | G IPERFS G S NSGNTATLTISGTQA E D EADYYC |

FIG. 2A

Vkappa

| SEQ ID NO: | Position | Framework 1 | CDR 1 |
|---|---|---|---|
| | | 1         2         3 | |
| | | 1 2 3 4 5 6 7 8 9 0 1 2 3 4 5 6 7 8 9 0 1 2 3 4 5 6 7 8 9 0 a b c d e f 1 2 3 4 | |
| | | EcoRV    BanII                    PstI | |
| 104 | VK4 | D I V M T Q S P D S L A V S L G E R A T I N C | R S S Q V L Y S S N K N Y L A |
| 36 | 4687 | D I V M T Q S P D S L A V S L G E R A T I N C | R S S Q S I L Y S N N N F L G |
| 37 | 5097 | D I V M T Q S P D S L A V S L G E R A T I N C | R S S Q S I L Y G N N N F L G |
| 82 | 5098 | D I V M T Q S P D S L A V S L G E R A T I N C | R S S Q S I L Y G N N N F L G |
| 39 | 5100 | D I V M T Q S P D S L A V S L G E R A T I N C | R S S Q S I L Y G N N N F L G |
| 40 | 5101 | D I V M T Q S P D S L A V S L G E R A T I N C | R S S Q S I L Y G N N N F L G |

| Framework 2 | CDR 2 | Framework 3 |
|---|---|---|
| 4         5 | | 6         7 |
| 5 6 7 8 9 0 1 2 3 4 5 6 7 8 9 | 0 1 2 3 4 5 6 7 8 9 | 0 1 2 3 4 5 6 7 8 9 0 1 2 3 4 5 |
| KpnI    SexAI         AseI | | SanDI        BamHI |
| W Y Q Q K P G Q P P K L L I Y | W A S T R E S | G V P D R F S G S G S G T D F T L T I |
| W Y Q Q K P G Q P P K L L I Y | W A S T R E S | G V P D R F S G S G S G T D F T L T I |
| W Y Q Q K P G Q P P K L L I Y | W A S T R E S | G V P D R F S G S G S G T D F T L T I |
| W Y Q Q K P G Q P P K L L I Y | W A S T R E S | G V P D R F S G S G S G T D F T L T I |
| W Y Q Q K P G Q P P K L L I Y | W A S T R E S | G V P D R F S G S G S G T D F T L T I |
| W Y Q Q K P G Q P P K L L I Y | W A S T R E S | G V P D R F S G S G S G T D F T L T I |

| | CDR 3 | Framework 4 |
|---|---|---|
| 8         9 | | 10 |
| 6 7 8 9 0 1 2 3 4 5 6 7 8 9 0 1 2 3 4 5 a 6 | 7 8 9 0 1 2 3 4 5 6 7 8 9 |
| BbsI | MscI    BsiWI |
| S S L Q A E D V A V Y Y C | Q Q Y Y S T P W T F G Q G T K V E I K R T |
| S S L Q A E D V A V Y Y C | Q Q Y Y N H P W T F G Q G T K V E I K R T |
| S S L Q A E D V A V Y Y C | Q Q Y A F S P W T F G Q G T K V E I K R T |
| S S L Q A E D V A V Y Y C | Q Q Y A S D P W T F G Q G T K V E I K R T |
| S S L Q A E D V A V Y Y C | Q Q Y A Y P P W T F G Q G T K V E I K R T |
| S S L Q A E D V A V Y Y C | Q Q Y A F S P W T F G Q G T K V E I K R T |

FIG. 3

COMPOSITIONS AND METHODS OF USE FOR ANTIBODIES OF C-MET

This application is a U.S. National Phase filing of International Application Serial No. PCT/US2007/007543 filed 29 Mar. 2007, and claims priority to U.S. Provisional Application Ser. No. 60/787,556 filed 30 Mar. 2006, the contents of which are incorporated herein by reference in their entirety.

TECHNICAL FIELD

The present invention relates to compositions containing antibodies that specifically bind to the protein-target c-Met, methods of making these antibodies, and methods of use to treat proliferative conditions, such as cancers and metastases, and inflammatory conditions.

BACKGROUND

The Hepatocyte Growth Factor Receptor, herein referred to as c-Met, is a receptor tyrosine kinase that has been shown to be over-expressed and/or mutated in a variety of malignancies, specifically, a number of c-Met mutations are found in various solid phase tumors. The c-Met ligand, hepatocyte growth factor (HGF), also known as scatter factor (SF), binds to c-Met in a pathway that is implicated in invasion and metastasis of tumor cells (Ma et al., 2003 Cancer and Metastasis Reviews. 22:309-325).

Interaction of HGF with c-Met initiates a cascade of intracellular events (Derman et al., 1996 J Biol Chem 23; 271(8): 4251-4255). Binding of HGF results in activation of the intrinsic tyrosine kinase activity of c-Met and autophosphorylation of several tyrosine residues on the intracellular domain (Ma et al., 2003 Cancer and Metastasis Reviews. 22:309-325). Activation of the HGF/c-Met pathway results in a wide array of cellular responses including cell scattering, angiogenesis, proliferation, enhanced cell miotility, invasion and metastasis. Antagonism may act to inhibit autophosphorylation and/or to induce internalization of the surface cMet, and/or to down regulate cMet activity.

Tumor cells can invade a tissue boundary, degrading and remodeling the surrounding extracellular matrix, such that the tumor cells can migrate through the extracellular matrix tissue boundary permitting dissemination and formation of metastases. HGF/c-Met signaling is a pathway that mediates normal and malignant invasive growth. Missense mutations of c-Met have been identified in a variety of cancers, with most mutations located in the kinase domain. Mutants are characterized by increased tyrosine kinase activity thereby promoting the biological actions of c-Met.

There is need for compositions and methods to treat cancers, metastasis of cancers and inflammatory conditions, such as agents that interfere with HGF/c-Met signaling in which c-Metactivity contributes to invasion and/or metastasis.

SUMMARY OF THE INVENTION

The receptor tyrosine kinase c-Met is involved in the processes of migration, invasion and morphogenesis that accompany embryogenesis and tissue regeneration. Several lines of evidence have indicated that, c-Met also plays a role in tumor pathogenesis. Activating germ line mutations within the kinase domain of c-Met are associated with development of hereditary papillary renal cell carcinoma (PRCC). Mutations within the kinase domain have also been reported, albeit rarely, in sporadic forms of PRCC, in head and neck squamous cell carcinoma and in gastric carcinoma. Elevated levels of c-Met, together with its unique ligand HGF/SF, are observed at high frequency in multiple clinically relevant tumors. A correlation between increased expression and disease progression, metastases and patient mortality has been reported in several cancers, including bladder, breast and gastric carcinoma as well as leiomyosarcoma and glioblastoma.

Antibodies of the invention specifically bind c-Met with high affinity and modulate the effect of c-Met of the disease. Antibodies that antagonize c-Met levels or activity are contemplated for treating proliferative diseases or inflammatory diseases. Proliferative diseases believed treatable by the antibodies of the invention include especially cancers. Antibodies that agonize c-Met levels or activity are contemplated for organ regeneration, wound healing, tissue regeneration, and the like.

An embodiment of the invention herein provides an antibody that selectively binds to a c-Met protein, or an immunologically active portion of this antibody, or a functional antibody fragment. In one embodiment the antibody or immunologically active portion of this antibody is from a mammal, having an origin such as rodent, human or camelid, or is a humanized antibody. In a particular embodiment, the anti-c-Met antibody is characterized as having an antigen-binding region that is specific for target protein c-Met, and the antibody or functional fragment binds to c-Met or a fragment of c-Met. The antibody may be polyclonal or monoclonal. In certain embodiments, the antibody or immunologically active portion of this antibody is a monoclonal antibody. Further embodiments of the invention include, e.g., a functional fragment, such as an antigen binding portion, or such a fragment provided on a non-traditional or non-immunoglobulin based scaffold or framework.

In another embodiment, the antibody or functional fragment of this antibody binds the target protein, c-Met, with a $K_D$ of $2.0 \times 10^{-5}$ M or less, $2.0 \times 10^{-6}$ M or less, $2.0 \times 10^{-7}$ M or less, $2.0 \times 10^{-8}$ M or less, or $2.0 \times 10^{-9}$ M or less. In a related embodiment the antibody or functional fragment of this antibody has an off rate ($K_{off}$) for target protein c-Met of $1.0 \times 10^{-2}$ per sec or smaller, $1.0 \times 10^{-3}$ per sec or smaller, $1 \times 10^{-4}$ per sec or smaller, or $1.0 \times 10^{-5}$ per sec or smaller. In a related embodiment, the antibody or functional fragment of this antibody binds the target protein c-Met with a $K_D$ of $2.0 \times 10^{-5}$ M or less, $2.0 \times 10^{-6}$ M or less, $2.0 \times 10^{-7}$ M or less, $2.0 \times 10^{-8}$ M or less, or $2.0 \times 10^{-9}$ M or less, and inhibits HGF binding to c-Met. In a related embodiment, the antibody or functional fragment thereof antagonizes cMet activity.

In certain embodiments, the antibody or functional fragment of this antibody binds the target protein c-Met and modulates, i.e., either activates (agonizes) or inhibits (antagonizes), c-Met activity, including but not limited to phosphorylation, especially autophosphorylation. In certain embodiments, agonism or activation of c-Met phosphorylation stimulates at least one of an activity selected from the group of organ regeneration, wound healing, and tissue regeneration. In a related embodiment, the organ is kidney, liver, pancreas, lung, stomach, intestine, skin, thymus, or thyroid.

In a preferred embodiment, the antibody of the invention antagonized cMet, wherein antagonism results in at least one activity selected from: inhibition of cellular proliferation; inhibition of cell migration, inhibition of cell survival, inhibition of metastasis and/or inhibition of HGS binding or from induction of cMet internalization. In most embodiments, the cMet antibody antagonist of the invention may be used in the treatment of a proliferative disease, especially a cancer or inflammatory disease.

In a related embodiment, the binding is determined by one or more assays that can be used to measure an activity which is either antagonism or agonism by the antibody. The assays measure at least one of the effects of the antibody on a c-Met ligand that include at least: induction of an activity of c-Met signal transduction pathway enzyme; induction of expression of a c-Met signal transduction pathway gene; electrochemiluminescence-based direct binding to c-Met; enzyme-linked immunosorbent assay of binding to c-Met; and proliferation, survival, migration or metastasis of a cell. Whether the antibody has an antagonistic or an agonistic effect is determined by comparing results to controls lacking the HGF natural ligand. Thus an antagonistic antibody blocks cMet induction even in the presence of HGF, while an agonistic antibody causes induction in the absence of HGF.

In another embodiment, the invention provides isolated amino acid and nucleotide sequences providing antibodies and the encoding isolated nucleotide sequence selected from the group of SEQ ID NOs: 1-30, 73-76, and 85-88. In a related embodiment, the invention provides isolated amino acid sequences encoded by these nucleotide sequences, respectively, and conservative variants of these amino acid sequences. In another related embodiment, the isolated nucleotide sequence of each of SEQ ID NOs: 1-20 encodes an amino acid sequence of antigen binding light chain. In still another related embodiment, the isolated nucleotide sequence of each of SEQ ID NOs: 21-30 encodes an amino acid sequence of an antigen binding heavy chain.

In another embodiment, the invention provides an isolated amino acid sequence selected from the group of SEQ ID NOs: 31-72, 77-84, and 89-96, and conservative variants of these sequences. In a related embodiment, the isolated amino acid sequence of each of SEQ ID NOs: 31-54 includes an antigen binding-light chain. In another related embodiment, the isolated amino acid sequence of each of SEQ ID NOs: 55-72 includes an antigen binding heavy chain.

In a certain embodiment, the invention provides an isolated amino acid sequence having at least 50, 60, 70, 80, 90, 95 or 99 percent identity with SEQ ID NOs: 31-72, 77-84, and 89-96. In a related embodiment, the invention provides an isolated nucleotide sequence having at least 60, 70, 80, 90, 95 or 99 percent identity with a sequence depicted in SEQ ID NOs: 1-30, 73-76, and 89-96.

In still another embodiment, the invention provides an isolated antigen-binding region of any of these antibodies, or a functional fragment of any of these antibodies. Thus in certain embodiments, the invention provides an isolated antigen-binding region having a light chain encoded by a nucleotide sequence selected from the group of SEQ ID NOs: 1-20. In related embodiment, the invention provides an isolated antigen-binding region having a heavy chain encoded by a nucleotide sequence selected from the group of SEQ ID NOs: 21-30. In another related embodiment, the invention provides an isolated antigen-binding region having a light chain encoded by a nucleotide sequence selected from the group of SEQ ID NOs: 1-20, and a heavy chain encoded by a nucleotide sequence selected from the group of SEQ ID NOs: 21-34.

In a related embodiment, the invention provides an isolated antigen-binding region having a light chain with an amino acid sequence selected from the group of SEQ ID NOs: 31-54. In another related embodiment, the invention provides an isolated antigen-binding region having a heavy chain with an amino acid sequence selected from the group of SEQ ID NOs: 55-72. In yet another related embodiment, the invention provides an isolated antigen-binding region having a light chain with an amino acid sequence selected from the group of SEQ ID NOs: 31-54 and conservative variants these sequences, and a heavy chain with an amino acid sequence selected from the group of SEQ ID NOs: 55-72 and conservative variants these sequences.

In another embodiment, the invention provides an isolated antigen-binding region having an Ig lambda light chain encoded by a nucleotide sequence of SEQ ID NO: 73. In a related embodiment, the invention provides an isolated antigen-binding region having an Ig kappa light chain encoded by a nucleotide sequence selected from the group of SEQ ID NOs: 74-76.

In a further embodiment, the invention provides an isolated antigen-binding region having an Ig lambda light chain with an amino acid sequence selected from the group of SEQ-ID NO: 77-80. In another related embodiment, the invention provides an isolated antigen-binding region having an Ig kappa light chain with an amino acid sequence selected from the group of SEQ ID NOs: 81-84.

In another embodiment, the invention provides an isolated human or humanized antibody or functional fragment of the antibody, the antibody having an antigen-binding region that is specific for an epitope found in c-Met protein, such that the antibody or functional fragment binds to c-Met surface receptors on a cell, and prevents or ameliorates development or metastasis of a cancer. In a related embodiment, the invention provides an isolated antibody or functional fragment having an, antigen-binding region that is specific for an epitope of the target protein c-Met, the epitope containing one or more amino acid residues of an extracellular domain (ECD) of c-Met. In a related embodiment, the epitope is a conformational epitope.

In yet another embodiment, the isolated antibody or functional fragment as described above is a Fab or scFv antibody fragment, or is a camelid nanobody. The Fab or scFv in certain embodiments are monovalent. The monovalent nature of the antibody is particularly suitable for an agent designed to antagonize c-Met protein. In a certain embodiment, any of the IgG antibodies is an IgG. In a related embodiment, any of the above antibodies is an IgG1, an IgG2, an IgG3 or an IgG4. In a particular embodiment, the IgG is an IgG4. In a more specific embodiment, the IgG4 is encoded by a nucleotide sequence selected from the group of SEQ ID NOs: 85-88. In yet another related embodiment, the IgG4 is encoded by a nucleotide sequence having at least 60, 70, 80, 90, 95 or 99 percent identity with a sequence selected from the group consisting of SEQ ID NOs: 85-88. In a further related embodiment, the IgG4 has an amino acid sequence selected from the group consisting of SEQ ID NOs: 89-96 and conservative variants of these sequences. Alternatively, the anti-c-Met antibody herein is an IgA, an IgD, an IgE or an IgM.

In another embodiment, the invention provides a pharmaceutical composition comprising at least one of the above antibodies or functional fragments or conservative variants of these antibodies, and a pharmaceutically acceptable carrier or excipient of it.

In still another embodiment, the invention provides a transgenic animal or a transgenic cell carrying a gene encoding any of the above antibodies or functional fragments of them.

In certain embodiments, the invention provides a method for treating a c-Met related disorder or condition, which involves administering to a subject in need thereof an effective amount of any of the above pharmaceutical compositions. The disorder or condition is a cancer or an inflammatory condition.

In one embodiment, the cancer is esophageal, breast, kidney including but not limited to papillary renal cell carcinoma, glioma, head and neck, epithelial, lung, skin, leukemia, lymphoma, myeloma, brain, pancreatic, gastric, gastrointestinal, stomach, colon, intestine, liver, genital, urinary, melanoma, or prostate, as well as other tumors known to one skilled in the art. In a particular embodiment, the cancer is liver or esophageal or is a sarcoma. More particularly, the cancer is selected from the group consisting of brain cancer, stomach cancer, genital cancer, urinary cancer, prostate cancer, bladder cancer (superficial and muscle invasive), breast cancer, cervical cancer, colon cancer, colorectal cancer, glioma (including glioblastoma, anaplastic astrocytoma, oligoastrocytoma, oligodendroglioma), esophageal cancer, gastric cancer, gastrointestinal cancer, liver cancer, hepatocellular carcinoma (HCC) including childhood HCC, head and neck cancer (including head and neck squamous-cell carcinoma, nasopharyngeal carcinoma); Hurthle cell carcinoma, epithelial cancer, skin cancer, melanoma including malignant melanoma, mesothelioma, lymphoma, myeloma including multiple myeloma, leukemias, lung cancer including non-small cell lung cancer (including all histological subtypes: adenocarcinoma, squamous cell carcinoma, bronchoalveolar carcinoma, large-cell carcinoma, and adenosquamous mixed type), small-cell lung cancer, ovarian cancer, pancreatic cancer, prostate cancer, kidney cancer, renal cell cancer including hereditary and sporadic papillary renal cell cancer, Type I and Type II, and clear cell renal cell cancer; sarcomas, in particular osteosarcomas, clear cell sarcomas, and soft tissue sarcomas (including alveolar and embryonal rhabdomyosarcomas, alveolar soft part sarcomas); thyroid carcinoma (papillary and other subtypes).

In a given embodiment, one exemplary inflammatory condition is due to an infection. In one embodiment, the method of treatment would be to block pathogen infection. In a particular embodiment, the infection is a bacterial infections, including, e.g., a *Listeria* infection. See, e.g., Shen et al. Cell 103: 501-10, (2000). Not meaning to be limited to a mechanism of action, it is thought that bacteria use a c-Met binding protein to internalize itself. Antibodies of the invention would block this interaction, thereby preventing internalization. In another embodiment, the treatment stimulates a cellular response, e.g., a wound healing response.

In certain embodiments, any of the above methods involve further administering a chemotherapeutic agent. In a related embodiment, the chemotherapeutic agent is an anti-cancer agent. Specific combinations are provided throughout the application.

In a related embodiment, any of the above methods involve further administering a pathway specific inhibitor. The pathway specific inhibitor may be a chemotherapeutic agent or may be a biologic agent, e.g., such as antibodies. Pathway specific inhibitors include, but are not limited to, inhibitors of EGFR, VEGFR, etc.

In still another embodiment, the invention provides a method for treating an unwanted cell that involves contacting the cell with any of the above antibodies or functional fragments of these antibodies. In a related embodiment, the cell bears c-Met on the cell surface. In another related embodiment, the above method further involves treating the cell with a chemotherapeutic agent or radiation.

In an embodiment related to several of the above methods, following administering to the subject or contacting the cell, these methods can further involve observing amelioration or retardation of development or metastasis of the cancer.

In yet another embodiment, the invention provides a method for identifying a cell bearing the c-Met surface receptor, the method involving contacting the cell with any of the above antibodies or functional fragments such that the antibodies or functional fragments have a detectable label. For example, the label is radioactive, fluorescent, magnetic, paramagnetic, or chemiluminescent. In a related embodiment, the above method further involves a step of imaging or separating the cell. For example, separating the cell is isolating the c-Met-bearing cell away from a larger population of cells.

In another embodiment, the above human or humanized antibody or antibody fragment is a synthetic antibody, for example, a polypeptide produced by a solid phase amino acid synthesizer.

In another embodiment, the invention provides a pharmaceutical composition that includes any of the above antibodies or functional fragments of these antibodies and an additional therapeutic agent. The additional therapeutic agent is selected from the group consisting of an anti-cancer agent; an antibiotic; an anti-inflammatory agent; a growth factor; and a cytokine.

The invention further relates to a method of preventing or treating proliferative diseases or diseases, such as a cancer, in a mammal, particularly a human, with a combination of pharmaceutical agents which comprises:
 (a) a c-Met antagonist of the invention; and
 (b) one or more pharmaceutically active agents;
wherein at least one pharmaceutically active agent is an anti-cancer therapeutic.

The invention further relates to pharmaceutical compositions comprising:
 (a) a c-Met antibody antagonist;
 (b) a pharmaceutically active agent; and
 (c) a pharmaceutically acceptable carrier;
wherein at least one pharmaceutically active agent is an anti-cancer therapeutic.

The present invention further relates to a commercial package or product comprising:
 (a) a pharmaceutical formulation of a c-Met antibody antagonist; and
 (b) a pharmaceutical formulation of a pharmaceutically active agent for simultaneous, concurrent, separate or sequential use;
wherein at least one pharmaceutically active agent is an anti-cancer therapeutic.

In a certain embodiment, the invention provides an isolated antibody having a first amino acid sequence which is a heavy chain such as SEQ ID NOs: 55-72, or a sequence having at least 60, 70, 80, 90, 95 or 99 percent sequence identity with a sequence selected from the group of SEQ ID NOs: 55-72; and a second amino acid sequence which is a light chain such as SEQ ID NOs: 31-54, or a sequence having at least 60, 70, 80, 90, 95 or 99% sequence identity with a sequence selected from the group of SEQ ID NOs: 31-54.

In still another embodiment, the invention provides an immunoconjugate having a first component which is an antibody or fragment as described above and a second component which is a second amino acid sequence. For example, the second compound of the immunoconjugate is a cytotoxin, or is a binding protein or antibody having a binding specificity for a target that is different from c-Met. For example, the target of the binding specificity different from c-Met is a tumor antigen or tumor-associated protein on a surface of a cancer cell. In certain embodiments, the invention provides any of the above antibodies as a bispecific antibody.

In another embodiment, the invention provides a kit having any of the above antibodies or antibody fragments. In some embodiments, the kit further contains a pharmaceutically acceptable carrier or excipient of it. In other related embodiments, any of the above antibodies in the kit is present in a unit dose. In yet another related embodiment, the kit includes instructions for use in administering any of the above antibodies, or functional fragments of these antibodies, to a subject, or for research use or screening.

Therapeutic agents that antagonize cMet activity would be predicted to have a beneficial impact on treatment of a wide range of clinically relevant tumors. Included in the invention are fully human antibodies that directly binds to the extracellular domain of c-Met and blocks interaction with HGF/SF.

BRIEF DESCRIPTION OF THE DRAWINGS

FIG. 1 is a sequence alignment of the $V_H$ chains of the invention, further delimiting the FR1, CDR1, FR2, CDR2, FR3, CDR3 and FR4 regions of each chain.

FIG. 3 is a sequence alignment of the $V_L$ kappa chains of the invention, further delimiting the FR1, CDR1, FR2, CDR2, FR3, CDR3 and FR4 regions of each chain.

DETAILED DESCRIPTION OF THE INVENTION

Figure 2B:
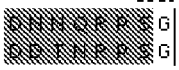
FIG. 2 is a sequence alignment of the $V_L$ lambda chains of the invention, further delimiting the FR1, CDR1, FR2, CDR2, FR3, CDR3 and FR4 regions of each chain.

The present invention relates to isolated antibodies, particularly antibodies having a human or humanized amino acid sequence, that bind specifically to c-Met, specifically to an extracellular portion of the c-Met protein and that inhibit functional properties of c-Met. In certain embodiments, the antibodies of the invention are derived from particular heavy and light chain sequences and/or comprise particular structural features such as CDR regions comprising particular amino acid sequences. The invention provides isolated antibodies, methods of making such antibodies, assays for detecting such antibodies, immunoconjugates and bispecific molecules comprising such antibodies and pharmaceutical compositions containing the antibodies, immunoconjugates or bispecific molecules of the invention. The invention also relates to methods of using the antibodies to inhibit, i.e., antagonize, function of c-Met in order to inhibit development of a disorder or condition associated with the presence of cell receptor target c-Met resulting in the treatment of a proliferative disease, e.g., a cancer or an inflammatory condition. The invention in a different embodiment also relates to antibodies that activate, i.e., agonize, c-Met phosphorylation, and methods of use of agonistic antibodies, which stimulate, for example, organ regeneration, wound healing, or tissue regeneration.

In a given embodiment, inflammatory condition is an infection. In one embodiment, the method of treatment would be to block pathogen infection. In a particular embodiment, the infection is a bacterial infections, including, e.g., a *Listeria* infection.

In order that the present invention may be more readily understood, certain terms are defined to have the meanings here, except as otherwise required by the context. Additional definitions are set forth throughout the detailed description.

A "c-Met polypeptide" or "c-Met receptor" or "c-Met" refers to the receptor tyrosine kinase that binds Hepatocyte Growth Factor. Specific examples include, e.g., a human polypeptide encoded by the nucleotide sequence provided in GenBank accno. NM_000245, or the human protein encoded by the polypeptide sequence provided in GenBank accno. NP_000236, or the extracellular domain of thereof. The primary single chain precursor protein is post-translationally cleaved to produce the alpha and beta subunits, which are disulfide linked to form the mature receptor. The receptor tyrosine kinase c-Met is involved in cell processes; including, e.g., the processes of migration, invasion and morphogenesis that accompany embryogenesis and tissue regeneration.

The phrase "c-Met related disorder or condition" refers to any disease, disorder or condition that results from undesired expression or lack of expression, undesired regulation or lack of regulation, or undesired activity or lack of activity, of c-Met, or that may be modulated, treated, or cured by modulating c-Met expression or activity. For example, activation of the HGF/c-Met pathway can be expected in a large proportion of cancer patients, or in patients whose disease is really driven by alterations related to the c-Met pathway. For example, up-regulation may be due to different mechanisms like over-expression of HGF and/or c-Met, or constitutive activation by c-Met mutation. A c-Met related disorder or condition includes, but is not limited to, e.g., proliferative diseases and disorders and inflammatory diseases and disorders. Proliferative diseases include but are not limited to, e.g., cancers including, e.g., gastric, esophageal, breast, kidney including papillary renal cell carcinoma, glioma, head and neck, epithelial, lung, skin, leukaemia, lymphoma, myeloma, brain, pancreatic, gastrointestinal, stomach, intestine, colon, liver, genital, urinary, melanoma, and prostate, as well as other tumors known to one skilled in the art. Inflammatory diseases include, but are not limited to, e.g., bacterial infection including, e.g., by *Listeria*. Further disorders are described herein and, e.g., in Online Mendelian Inheritance in Man ("OMIM") entries for, e.g., Met proto-oncogene in OMIN accno. 164860 and for Hepatocyte Growth Factor/Scatter Factor in OMIM accno. 142409. Other examples will be known to those skilled in the art, e.g., as reviewed by Corso et al., TRENDS in Mol. Med. 11(6): 2841 (2005) and Christensen et al., Cancer Letts. 225: 1-26 (2005), both of which are incorporated by reference.

The term "immune response" refers to any activity of lymphocytes, antigen presenting cells, phagocytic cells, granulocytes, and soluble macromolecules produced by these cells or by the liver (including production and/or secretion of antibodies, cytokines, and complement) that results in selective binding to, damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

A "surface receptor" includes, for example, molecules and complexes of molecules capable of receiving a signal and capable of the transmission of such a signal across the plasma membrane of a cell. An example of a cell surface receptor of the present invention is c-Met, to which a growth factor protein molecule binds e.g., a hepatocyte growth factor (HGF).

The term "antibody" encompasses any moiety having immunoglobulin-like binding function. The term includes whole antibody molecules and any antigen binding fragment (i.e., "antigen-binding portion") or single chains thereof, camelid antibodies including, e.g., nanobodies, phage-display binding constructs, and the like. A naturally occurring antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. There are only two types of light chain: lambda and kappa. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). As found in nature, each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody may be monoclonal or polyclonal.

The term "antigen-binding portion" of an antibody (or simply "antigen portion") refers to full length or one or more fragments of an antibody having the ability to specifically bind to an antigen (e.g., a portion of c-Met). It has been shown that the antigen-binding function of an antibody can be performed by fragments of a full-length antibody molecule. Examples of binding fragments containing an antigen-binding portion of an antibody include a Fab fragment, which is a monovalent fragment consisting of the $V_L$, $V_H$, $C_L$ and CH1 domains; a F(ab)$_2$ fragment, which is a bivalent fragment comprising two Fab fragments linked by a disulfide bridge at the hinge region; a Fd fragment having the $V_H$ and CH1 domains; a Fv fragment having the $V_L$ and $V_H$ domains of a single amino acid sequence of an antibody chain; a dAb fragment (Ward et al., 1989 Nature 341:544-546), which has a $V_H$ domain; and an isolated complementarity determining region (CDR).

Reference to an antibody fragments that contain the antigen-binding portions may contemplate the isolated fragment or conjugated to chemical or biological moieties, or to fragments attached to non-traditional immunoglobulin-derived frameworks or scaffolds, including but not limited to, e.g., ankyrins, fibronectins, domain antibodies, lipocalin, small modular immuno-pharmaceuticals, maxybodies, nanobodies, protein A, affilin, gamma-crystallin and ubiquitin, and other contemplated scaffolds known to one skilled in the art.

Furthermore, although in a naturally occurring antibody molecule there are two chains having Fv domains, $V_L$ and $V_H$, which are encoded by separate genes, they can be joined using recombinant methods, by a synthetic linker that enables them to be recombinantly expressed as a single protein chain in which the $V_L$ and $V_H$ regions form one monovalent molecule (known as single chain Fv (scFv); see e.g., Bird et al., 1988 Science 242:423-426; and Huston et al., 1988 Proc. Natl. Acad. Sci. 85:5879-5883). Such single chain antibodies are also encompassed within the term antigen-binding portion of an antibody. These antibody fragments are obtained using conventional techniques known to those of skill in the art, and the fragments are screened for utility in the same manner as are intact antibodies or other fragments thereof.

An "isolated antibody" refers to an antibody that is substantially free of other antibodies having different antigenic specificities (e.g., an isolated antibody that specifically binds to a determinant that is a set of amino acids on c-Met is substantially free of antibodies that bind specifically and substantially to antigens other than c-Met). An isolated antibody that specifically binds to a c-Met protein such as human c-Met may, however, have cross-reactivity to other antigens, such as to c-Met molecules from other species, or to proteins having a high amount of homology to a human c-Met amino acid sequence. Moreover, an isolated antibody may be substantially free of other cellular material and/or chemicals.

The terms "monoclonal antibody" or "monoclonal antibody composition" refer to a preparation of antibody molecules, all of which share a single molecular composition. A monoclonal antibody composition thus displays a single binding specificity and affinity for a particular epitope.

As used herein, the term "polyclonal antibody" refers to an antibody composition having a heterogeneous antibody population. Polyclonal antibodies are often derived from the pooled serum from immunized animals or from selected humans.

The term "human antibody", as used herein, is intended to include antibodies having variable regions in which at least one and generally both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations such as substitutions introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a heavy chain transgene, generally of human origin, and a light chain transgene, generally of human origin, fused to an immortalized cell, generally of human origin.

The term "recombinant human antibody", as used herein, includes human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of one or more human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis), so that the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgA, IgD, IgM, IgE, or IgG such as IgG1, an IgG2, an IgG3 or IgG4) that is provided by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human c-Met" is intended to refer to an antibody that binds to human c-Met with a $K_D$ of $2.0 \times 10^{-5}$ M or less, $2.0 \times 10^{-6}$ M or less, $2.0 \times 10^{-7}$ M or less, $2.0 \times 10^{-8}$ M or less, or $2.0 \times 10^{-9}$ M or less. As used herein, the term "cross-reactivity" refers to an antibody or population of antibodies binding to epitopes on other antigens. This can be caused either by low avidity or specificity of the antibody or by multiple distinct antigens having identity or very similar epitopes. Cross reactivity is sometimes desirable when one wants general binding to a related group of antigens or when attempting cross-species labeling if the antigen epitope sequence is not highly conserved in evolution.

An antibody that "cross-reacts with an antigen other than human c-Met" refers to an antibody that binds that antigen with a $K_D$ of $0.5 \times 10^{-7}$ M or less, $5 \times 10^{-8}$ M or less, or $2 \times 10^{-9}$ M or less. An antibody that "does not cross-react with a particular antigen" is intended to refer to an antibody that binds to that antigen, if at all, with a $K_D$ of $1.5 \times 10^{-8}$ M or greater, or a $K_D$ of $5\text{-}10 \times 10^{-7}$ M or $5 \times 10^{-6}$ M or greater. In certain embodiments, such antibodies that do not cross-react with the antigen exhibit essentially undetectable binding against these proteins in standard binding assays.

As used herein, an antibody that "inhibits binding to c-Met" refers to an antibody that inhibits HGF/SF ligand binding to the c-Met surface receptor with a $K_i$ of 10 nM or less, 5 nM or less, 1 nM or less, 0.75 nM or less, 0.5 nM or less, or 0.25 nM or less.

As used herein, an antibody that "inhibits c-Met signal transduction activity" is intended to refer to an antibody that inhibits c-Met induced proliferative activity or other induced activity with an $IC_{50}$ less than 10 nM, 5 nM, 2.5 nM, 1.0 nM, 0.5 nM, or less.

The term "$K_{assoc}$" or "$K_a$", as used herein, is intended to refer to the association rate of a particular antibody-antigen interaction, and the term "$K_{dis}$" or "$K_D$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "agonist antibody" or "activating antibody" is intended to refer to an antibody that increases one or more c-Met induced activities by at least 20%-40% when added to a cell, tissue or organism expressing c-Met. In some embodiments, the antibody activates c-Met activity by at least 50%, 60%, 70%, 80%, 85%, 90%, 95%, 100% or greater than 100%. In some embodiments, an agonist antibody of the invention increases at least one activity of c-Met by 10-fold. Generally, this increase is observed in the absence of the biological inducer, HGF. However, in some embodiments, such as in a control for an assay, the activating antibody is added in the presence of HGF.

As used herein, the term "affinity" refers to the strength of interaction between antibody and a portion of the antigen known as the "epitope", at a single antigenic site. Within each antigenic site, the variable region of the antibody "arm" interacts through weak non-covalent forces with antigen at numerous atomic locations or amino acid residue atoms of the antibody; generally, the larger the number of such interactions, the stronger the affinity of the antibody for the antigen.

As used herein, the term "avidity" refers to an informative measure of the overall stability or strength of the antibody-antigen complex. It is controlled by three major factors: antibody-epitope affinity; the valence of each of the antigen and antibody; and the structural arrangement or three-dimensional configuration of these interacting parts. Ultimately these factors define the specificity of the antibody, that is, the likelihood that the particular antibody binds to a precise antigen epitope and the stability and duration of the bond.

In order to obtain a probe having a higher avidity, a dimeric conjugate (two molecules of an antibody protein or polypeptide coupled to a FACS marker) can be constructed, thus making low affinity interactions (such as with a germline antibody) more readily detected by FACS. Another means to increase the avidity of antigen binding involves generating dimers or multimers of any of the constructs described herein of the c-Met antibodies. Such -multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in constructing anti-c-Met antibody hybrids such as bi-functional antibodies, to create such higher order structures.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, or $10^{-8}$ M or less.

As used herein, the term "subject" includes any mammal, including a human, or a nonhuman mammal, or other animal. The term "nonhuman animal" includes all vertebrates, e.g., mammals, such as nonhuman primates, sheep, dogs, cats, horses, cows, and non-mammals such as birds, amphibians, reptiles, etc.

The term, "optimized" means that a nucleotide sequence has been altered to encode an amino acid sequence using codons that are preferred in the production cell or organism, generally a eukaryotic cell, for example, a cell of a yeast such as *Pichia*, a mammalian cell such as Chinese Hamster Ovary cell (CHO) or a human cell. The optimized nucleotide sequence is engineered to retain completely or as much as possible the amino acid sequence encoded by the original starting nucleotide sequence, which is also known as the "parental" sequence. The optimized sequences herein have been engineered to have codons with nucleotide sequences that are preferred in human cells, however optimized expression of these sequences in other eukaryotic cells is also envisioned herein. The amino acid sequences of antibodies herein encoded by optimized nucleotide sequences are also referred to as optimized.

Various aspects of the invention are described in further detail in the following subsections.

Standard assays to evaluate the binding ability of the antibodies toward c-Met of various species are known in the art, including for example, ELISAs, western blots and RIAs. Suitable assays are known to ones skilled in the art. See, e.g., F. Ausubel, et al., ed. 2006, Current Protocols in Molecular Biology, Greene Publishing and Wiley Interscience, New York. The binding kinetics (e.g., binding affinity) of the antibodies also can be assessed by standard assays known in the art, such as by Biacore analysis. Assays to evaluate the effects of the antibodies on functional properties of c-Met (e.g., inducing internalization of the receptor, inhibiting growth factor binding to c-Met, inhibiting cMet autophosphorylation, inhibiting cMet pathway activation, thereby preventing or ameliorating proliferation, or kinase assays) are described in herein.

Accordingly, an antibody that "inhibits" one or more of these c-Met functional properties (e.g., biochemical, immunochemical, cellular, physiological or other biological activities, or the like) as determined according to methodologies known to the art and described herein, relates to a statistically significant antagonism or decrease in the particular activity relative to that seen in the absence of the antibody (e.g., or in the presence of a control antibody of irrelevant specificity). An antibody that inhibits c-Met activity effects such a statistically significant decrease by at least 10% of the measured parameter, by at least 50%, 80% or 90%, and in certain embodiments an antibody of the invention may inhibit greater than 95%, 98% or 99% of c-Met functional activity. Generally, the decrease of activity is measured following an induction event, such as addition of HGF.

Alternatively, an antibody that "agonizes" one or more of these c-Met functional properties (e.g., biochemical, immunochemical, cellular, physiological or other biological activities, or the like) as determined according to methodologies known to the art and described herein, relates to a statistically significant increase in the particular activity relative to that seen in the absence of the antibody (e.g., or in the presence of a control antibody of irrelevant specificity). An antibody that stimulates or agonizes c-Met activity effects such a statistically significant increase by at least 10% of the measured parameter, by at least 50%, 80% or 90%, and in certain embodiments an antibody of the invention may agonize greater than 95%, 98% or 99% or greater, of c-Met functional activity.

Recombinant Antibodies

Antibodies of the invention are the recombinant antibodies, isolated and structurally characterized as described in the Examples. The $V_H$ nucleotide sequences of the antibodies are shown in SEQ ID NOs: 21-30 respectively. Tables C-E provide examples of $V_H$ nucleotide sequences of different antibodies of the invention. The $V_L$ nucleotide sequences of the antibodies are shown in SEQ ID NOs: 1-20 respectively. (Tables C-E provide examples of $V_L$ nucleotide sequences of different antibodies of the invention). The Ig lambda and kappa light chain nucleotide sequences of the antibodies are shown in SEQ ID NOs: 73-76 and in Tables C-E. The IgG4 nucleotide sequences of the antibodies are shown in SEQ ID NOs: 85-88 and in Tables C-E. Other antibodies of the invention include nucleotides that have been -mutated, yet have at least 60, 70, 80, 90, 95 or 99 percent identity with the sequences described above.

The $V_H$ amino acid sequences of the antibodies are shown in SEQ ID NOs: 55-72 respectively and in Tables A-B and E. The $V_L$ amino acid sequences of the antibodies are shown in SEQ ID NOs: 31-54 respectively and in Tables A-B and E. The Ig lambda light chain amino acid sequences are shown in SEQ ID NOs: 77-80 respectively and in Tables A-B and E. The Ig kappa light chain amino acid sequences of the antibodies are shown in SEQ ID NOs: 81-84 respectively and in Tables A-B and E. The IgG4 amino acid sequences of the antibodies are shown in SEQ ID NOs: 89-96 respectively and in Tables A-B and E. Additional antibodies of the invention include amino acids that have been mutated, and retain at least 60, 70, 80, 90, 95 or 99 percent identity with the sequences described above.

Since each of these antibodies can bind to a site on an extracellular portion of c-Met, the $V_H/V_L$ (nucleotide sequences and amino acid sequences), $V_H$/Ig lambda light chain (nucleotide sequences and amino acid sequences), and $V_H$/Ig kappa light chain (nucleotide sequences and amino acid sequences) can be "mixed and matched" to yield additional combinations of anti-c-Met binding molecules of the invention. c-Met binding of such antibodies can be tested using the binding assays described above and in the Examples (e.g., ELISAs). The $V_H$, $V_L$, Ig lambda light chain, and Ig kappa light chain sequences of the antibodies of the present invention are particularly amenable for novel combinations, since these antibodies use $V_H$, $V_L$, Ig lambda light chain, and Ig Kappa light chain sequences derived from the same or similar germline sequences and thus exhibit structural similarity.

Accordingly, in one aspect, the invention provides an isolated recombinant antibody or antigen binding portion thereof having at least: a heavy chain variable region ($V_H$) comprising an amino acid sequence selected from the group consisting of SEQ ID NOs: 55-72; and a light chain variable region ($V_L$) comprising an amino acid sequence selected from the group consisting of SEQ ID NOs: 31-54; wherein the antibody specifically binds c-Met.

Examples of heavy and light chain combinations include at least: a $V_H$ of SEQ ID NO: 65 and a $V_L$ of SEQ ID NO: 32; or a $V_H$ of SEQ ID NO: 66 and a $V_L$ of SEQ ID NO: 34; or a $V_H$ of SEQ ID NO: 67 and a $V_L$ of SEQ ID NO: 37; or a $V_H$ of SEQ ID NO: 68 and a $V_L$ of SEQ ID NO: 38 or a $V_H$ of SEQ ID NO: 69 and a $V_L$ of SEQ ID NO: 51; or a $V_H$ of SEQ ID NO: 70 and a $V_L$ of SEQ ID NO: 52; or a $V_H$ of SEQ ID-NO: 71 and a $V_L$ of SEQ ID NO: 53; or a $V_H$ of SEQ ID NO: 72 and a $V_L$ of SEQ ID NO: 54; or a $V_H$ of SEQ ID NO: 55 and a $V_L$ of SEQ ID NO: 31; or a $V_H$ of SEQ ID NO; 58 and a $V_L$ of SEQ ID NO: 36; or a $V_H$ of SEQ ID NO: 61 and a $V_L$ of SEQ ID NO: 41; or a $V_H$ of SEQ ID NO: 62 and a $V_L$ of SEQ ID NO: 45. Tables A-B illustrate examples of "mixed and matched" pairings of $V_H$ and $V_L$ amino acid sequences of different antibodies of the invention. FIGS. 1-3 are tables illustrating examples of a $V_H$ and $V_L$ amino acid sequence. illustrating FR and CDR regions that may be provided on alternative scaffolds to provide constructs having same or similar cMet antagonistic activity as the antibodies herein.

Accordingly, in another aspect, the invention provides an isolated recombinant antibody or antigen binding portion thereof having at least: a $V_H$ region comprising an amino acid sequence selected from the group consisting of SEQ ID NOs: 55-72 and a Ig lambda light chain comprising an amino acid sequence selected from the group consisting of SEQ ID NOs: 77-80, wherein the antibody specifically binds c-Met.

Examples of $V_H$/Ig lambda light chain combinations include at least: a $V_H$ of SEQ ID NO: 66 and an Ig lambda light chain of SEQ ID NO: 77; or a $V_H$ of SEQ ID NO: 65 and an Ig lambda light chain of SEQ ID NO: 78; or a $V_H$ region comprising the amino acid sequence of SEQ. ID NO: 69 an Ig lambda light chain of SEQ ID NO: 79; or a $V_H$ region of SEQ ID NO: 70 and an Ig lambda light chain of SEQ ID NO: 80.

Accordingly, in another aspect, the invention provides an isolated recombinant antibody or antigen binding portion thereof having at least: a $V_H$ region comprising an amino acid sequence selected from the group consisting of SEQ ID NOs: 55-72 and a Ig kappa light chain comprising an amino acid sequence selected from the group consisting of SEQ ID NOs: 81-84 wherein the antibody specifically binds c-Met.

Examples of $V_H$/Ig kappa light chain combinations include at least: a $V_H$ region of SEQ ID NO: 71 and an Ig kappa light chain of SEQ ID NO: 81; or a $V_H$ region of SEQ ID NO: 68 and an Ig kappa light chain of SEQ ID NO: 82; or a $V_H$ region of SEQ ID NO: 67 and an Ig kappa light chain of SEQ ID NO: 83; or a $V_H$ region of SEQ ID NO: 72 and an Ig kappa light chain of SEQ ID NO: 84.

In another aspect, the invention provides an isolated recombinant antibody or antigen binding portion thereof having at least: a $V_H$ chain comprising a nucleotide sequence selected from the group consisting of SEQ ID NOs: 21-30 and a $V_L$ chain comprising a nucleotide sequence selected from the group consisting of SEQ ID NOs: 1-20.

Thus examples of heavy and light chain combinations include at least: a $V_H$ region comprising the nucleotide sequence of SEQ ID NO: 21 and a light chain variable region comprising the nucleotide sequence of SEQ ID NO: 1; or a $V_H$ region comprising the nucleotide sequence of SEQ ID NO: 24 and a light chain variable region comprising the nucleotide sequence of SEQ ID NO: 6; or a $V_H$ region comprising the nucleotide sequence of SEQ ID NO: 27 and a light chain variable region comprising the nucleotide sequence of SEQ ID NO: 11; or a $V_H$ region comprising the nucleotide sequence of SEQ ID NO: 28 and a light chain variable region comprising the nucleotide sequence of SEQ ID NO: 15; or a $V_H$ region comprising the nucleotide sequence of SEQ ID NO: 29 and a light chain variable region comprising the nucleotide sequence of SEQ. ID NO: 18; or a $V_H$ region comprising the nucleotide sequence of SEQ ID NO: 30 and a light chain variable region comprising the nucleotide sequence of SEQ ID NO: 20; or a $V_H$ region comprising the nucleotide sequence of SEQ ID NO: 22 and a light chain variable region comprising the nucleotide sequence of SEQ ID NO: 1, or a $V_H$ region comprising the nucleotide sequence of SEQ ID NO: 23 and a light chain variable region comprising the nucleotide sequence of SEQ ID NO: 1; or a $V_H$ region comprising the nucleotide sequence of SEQ ID NO: 24 and a light chains variable region comprising the nucleotide sequence of SEQ ID NO: 7; or a $V_H$ region comprising the nucleotide sequence of SEQ ID NO: 24 and a light chain variable region comprising the nucleotide sequence of SEQ ID NO: 8; or a $V_H$ region comprising the nucleotide sequence of SEQ ID NO: 24 and a light chain variable region comprising the nucleotide sequence of SEQ ID NO: 9; or a $V_H$ region comprising the nucleotide sequence of SEQ ID NO: 24 and a light chain variable region comprising the nucleotide sequence of SEQ ID NO: 10. See Tables A-B illustrate examples of "mixed and matched" pairings of $V_H$ and $V_L$ nucleotide sequences of different antibodies of the invention for further examples of pairings of $V_H$ and $V_L$ nucleotide sequences.

In another aspect, the invention provides an isolated recombinant antibody or antigen binding portion thereof having at least: a $V_H$ chain comprising a nucleotide sequence selected from the group consisting of SEQ ID NOs: 21-30 and an Ig lambda light chain comprising a nucleotide sequence selected from the group consisting of SEQ ID NOs: 73.

Thus an example of a $V_H$/Ig lambda light chain combination includes: a $V_H$ region comprising the nucleotide sequence of SEQ ID NO: 23 and an Ig lambda light chain comprising the nucleotide sequence of SEQ ID NO: 73.

In another aspect, the invention provides an isolated recombinant antibody or antigen binding portion thereof having at least: a $V_H$ chain comprising a nucleotide sequence selected from the group consisting of SEQ ID NOs: 21-30 and an Ig kappa light chain comprising a nucleotide sequence selected from the group consisting of SEQ ID NOs: 74-76.

Thus examples of $V_H$ and Ig kappa light chain combinations include at least: a $V_H$ region comprising the nucleotide sequence of SEQ ID NO: 24 and an Ig kappa light chain variable region comprising the nucleotide sequence of SEQ ID NO: 74; or a $V_H$ region comprising the nucleotide sequence of SEQ ID NO: 25 and an Ig kappa light chain variable region comprising the nucleotide sequence of SEQ ID NO: 75; or a $V_H$ region comprising the nucleotide sequence of SEQ ID NO: 27 and an Ig kappa light chain variable region comprising the nucleotide sequence of SEQ ID NO: 76.

As used herein, a human antibody comprises heavy or light chain variable regions that are "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest, or screening a human immunoglobulin gene library displayed on phage with the antigen of interest. A human antibody that is the product of or derived from a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is the product of or derived from a particular human germline immunoglobulin sequence may contain amino acid differences as compared to the germline sequence. Such differences are due to, for example, at least one naturally occurring somatic mutations or an intentionally introduction of site-directed mutation. However, a selected human antibody typically is at least 90% identical in amino acids sequence to an amino acid sequence encoded by a human germline immunoglobulin gene and contains amino acid residues that identify the human antibody as being of human origin when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identity in amino acid sequence to the amino acid sequence encoded by a germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Identity Antibodies

In yet another embodiment, an antibody of the invention has at least variable region heavy and light chain nucleotide sequences, or variable region heavy and light chain amino acid sequences, or Ig lambda nucleotide sequences, or Ig lambda amino acid sequences, or Ig kappa nucleotide sequences, or Ig kappa amino acid sequences or IgG4 nucleotide sequences, or IgG4 amino acid sequences that have homology or identity to the amino acid and nucleotide sequences of the antibodies described herein, and wherein the antibodies retain the desired functional properties of the anti-c-Met antibodies of the invention, i.e., demonstrate the parental functional activity or activities. The parental functional activities can be antagonistic or agonistic. In most embodiments, the activity is antagonistic.

For example, the invention provides an isolated recombinant antibody, or antigen binding portion thereof, having a $V_H$ region and a light chain variable region, such that the $V_H$ region comprises an amino acid sequence that has at least 80%, 85%, 90%, 95% or 99% identity to an amino acid sequence selected from the group consisting of SEQ ID NOs:

55-72, the light chain variable region comprises an amino acid sequence that has at least 80%, 85%, 90%, 95% or 99% identity to an amino acid sequence selected from the group consisting of SEQ ID NOs: 31-54, wherein the antibody specifically binds to c-Met and the antibody exhibits at least one of the following functional antagonistic properties: the antibody induces internalization of the cMet receptor or the antibody inhibits binding of a protein growth factor to c-Met, or the antibody inhibits autophosphorylation of c-Met thereby preventing activation of the c-Met pathway, or the antibody inhibits cMet pathway upregulation resulting from signal transduction, or the antibody -inhibits c-Met binding, thereby preventing or ameliorating cell proliferation, -survival, migration, invasion or changes in morphology, and especially preventing or ameliorating cancer such as tumor growth and or metastasis.

In an alternative embodiment, the antibody is responsive and activates c-Met phosphorylation stimulating a cellular response. In one embodiment, the cellular response is a wound healing response.

In a further example, the invention provides an isolated recombinant antibody, or antigen binding portion thereof, haying an Ig lambda light chain such that the Ig lambda light chain comprises an amino acid sequence that is at least 80% identity to an amino acid sequence selected from the group consisting of SEQ ID NOs: 77-80. In further embodiments, the antibody specifically binds to c-Met, and the antibody exhibits at least one of the following functional properties: the antibody activates induces internalization of the cMet receptor, the antibody inhibits binding of a protein growth factor to c-Met, with such inhibition thereby preventing activation of the receptor, e.g., preventing pathway upregulation resulting from cMet activation and/or signal transduction, or the antibody preventing or ameliorating cell proliferation, cell survival, migration, invasion or changes in morphology, or the antibody antagonizes c-Met activity, thereby preventing or ameliorating cancer such as tumor growth and or metastasis.

In an alternative embodiment, the antibody activates c-Met phosphorylation stimulating a cellular response.

In another example, the invention provides an: isolated recombinant antibody, or antigen binding portion thereof, having an Ig kappa light chain wherein: the Ig kappa light chain has an amino acid sequence that has at least 80% identity to an amino acid sequence selected from the group consisting of SEQ ID NOs: 81-84; the antibody specifically binds to c-Met, and the antibody exhibits at least one of the functional properties provided above and throughout the specification. In an alternative embodiment, the antibody activates c-Met phosphorylation stimulating a cellular response.

In another embodiment, the invention provides an isolated recombinant antibody, or antigen binding portion thereof in which the antibody is an IgG4 such that the IgG4 has an amino acid sequence that is at least 80% identity to an amino acid sequence selected from the group consisting of SEQ ID NOs: 89-96; the antibody specifically binds to c-Met, and the antibody exhibits at least one of the following functional properties provided above and throughout the specification. In an alternative embodiment, the antibody is agonistic, and activates c-Met phosphorylation stimulating a cellular response.

In various embodiments, the antibody may exhibit one or more, two or more, or three or more of the antagonistic functional properties discussed herein. The antibody can be, for example, a human antibody, a humanized antibody or a chimeric antibody.

In another embodiment, the invention provides an isolated recombinant antibody, or antigen binding portion thereof, having a $V_H$ region and a light chain variable region, such that the $V_H$ region is encoded by a nucleotide sequence that is at least 80% identity to a nucleotide sequence selected from the group consisting of SEQ ID NOs: 21-30; the light chain variable region is encoded by a nucleotide sequence that is at least 80% identity to a nucleotide sequence selected from the group consisting of SEQ ID NOs: 1-20; the encoded antibody specifically binds to c-Met, and the antibody exhibits at least one of the functional properties provided above and throughout the specification. In an alternative embodiment, the antibody activates c-Met phosphorylation stimulating a cellular response.

In a further example, the invention provides an isolated recombinant antibody, or antigen binding portion thereof, having an Ig lambda light chain such that the Ig lambda light chain encoded by a nucleotide sequence that is at least 80% identity to a nucleotide sequence selected from the group consisting of SEQ ID NO: 73; the encoded antibody specifically binds to c-Met, and the antibody exhibits at least one of the functional properties provided above and throughout the specification. In an alternative embodiment, the antibody is agonistic and activates c-Met phosphorylation stimulating a cellular response.

In another example, the invention provides an isolated recombinant antibody, or antigen binding portion thereof, having an Ig kappa light chain wherein: the Ig kappa light chain encoded by a nucleotide sequence that is at least 80% identity to a nucleotide sequence selected from the group consisting of SEQ ID NOs: 74-76; the antibody specifically binds to c-Met, and the antibody exhibits at least one of the functional properties provided above and throughout the specification. In an alternative embodiment, the antibody activates c-Met phosphorylation stimulating a cellular response.

In another embodiment, the invention provides an isolated recombinant antibody, or antigen binding portion thereof in which the antibody is an IgG4 in which the IgG4 is encoded by a nucleotide sequence that is at least 80% identity to a nucleotide sequence selected from the group consisting of SEQ ID NOs: 85-88; the encoded antibody specifically binds to c-Met, and the antibody exhibits at least one of the functional properties provided above and throughout the specification. In an alternative embodiment, the antibody is agonistic, and activates c-Met phosphorylation stimulating a cellular response.

In various embodiments, the antibody may exhibit one or more, two or more, or three of the antagonistic functional properties discussed herein. The antibody can be, for example, a human antibody, a humanized antibody or a chimeric antibody.

In other embodiments, the $V_H$ and/or $V_L$ amino acid sequences may be 50%, 60%, 70%, 80%, 90%, 95%, 96%, 97%, 98% or 99% identity to the sequences set forth above. An antibody having $V_H$ and $V_L$ regions having high (i.e., 80% or greater) identity to the $V_H$ and $V_L$ regions of SEQ ID NOs: 31-72 respectively, can be obtained by mutagenesis (e.g., site-directed or PCR-mediated mutagenesis) of nucleic acid molecules encoding SEQ ID NOs: 31-72, followed by testing of the encoded altered antibody for retained function (i.e., the functions set forth above) using the functional assays described herein.

In other embodiments, the variable regions of heavy chain and/or light chain nucleotide sequences may be 60%, 70%, 80%, 90%, 95%, 96%, 97%, 98% or 99% identity to the sequences set forth above. An antibody having a variable region heavy chain and light chain having high (i.e., 80% or greater) identity to the variable region heavy chains of SEQ ID NO: 21-30 and variable region light chains of SEQ ID NO: 1-20 respectively, can be obtained by mutagenesis (e.g., site-directed or PCR-mediated mutagenesis) of nucleic acid molecules comprising SEQ -ID NOs: 1-30 followed by testing of the encoded altered antibody for retained function (i.e., the functions set forth above) using the functional assays described herein.

In other embodiments, the Ig lambda light chain amino acid sequences may be 50%, 60%, 70%, 80%, 90%, 95%, 96%, 97%, 98% or 99% identical to the sequences set forth above. An antibody having a Ig lambda light chain with high (i.e., 80% or greater) identity to the Ig lambda light chains of SEQ ID NOs: 77-80 respectively, can be obtained by mutagenesis (e.g., site-directed or PCR-mediated mutagenesis) of nucleic acid molecules encoding SEQ ID NOs: 77-80, followed by testing of the encoded altered antibody for retained function (i.e., the functions set forth above) using the functional assays described herein.

In other embodiments, the Ig lambda light chain nucleotide sequence may be 60%, 70%, 80%, 90%, 95%, 96%, 97%, 98% or 99% identical to the sequence set forth above. An antibody having an Ig lambda light chain with high (i.e.; 80% or greater) identity to the Ig lambda light chain of SEQ ID NO: 73-respectively, can be obtained by mutagenesis (e.g., site directed or PCR-mediated mutagenesis) of nucleic acid molecules comprising SEQ ID NO: 73 followed by testing of the encoded altered antibody for retained function (i.e., the functions set forth above) using the functional assays described herein.

In other embodiments, the Ig kappa light chain amino acid sequences may be 50%, 60%, 70%; 80%, 90%, 95%, 96%, 97%, 98% or 99% identical to the sequences set forth above. An antibody having a Ig kappa light chain with high (i.e., 80% or, greater) identity to the Ig kappa light chains of SEQ ID NOs: 81-84 respectively, can be obtained by mutagenesis (e.g., site-directed or PCR-mediated mutagenesis) of nucleic acid molecules encoding SEQ ID NOs: 81-84, followed by, testing of the encoded altered antibody for retained function (i.e., the functions set forth above) using the functional assays described herein.

In other embodiments, the Ig kappa light chain nucleotide sequence may be 60%, 70%, 80%, 90%, 95%, 96%, 97%, 98% or 99% identical or homologous to the sequence set forth above. An antibody having an Ig kappa light chain with high (i.e., 80% or greater) identity to the Ig kappa light chains of SEQ ID NOs: 74-76 respectively, can be obtained by mutagenesis (e.g., site-directed or PCR-mediated mutagenesis) of nucleic acid molecules comprising SEQ ID NOs: 74-76 followed by testing of the encoded altered antibody for retained function (i.e., the functions set forth-above) using the functional assays described herein.

In other embodiments, the antibody that is an IgG4 may be 50%, 60%, 70%, 80%, 90%, 95%, 96%, 97%, 98% or 99% identical to the amino acid sequences set forth above. An IgG4 with high (i.e., 80% or greater) identity to the IgG4 compositions of SEQ ID NOs: 89-96 respectively, can be obtained by mutagenesis (e.g., site-directed or PCR-mediated mutagenesis) of the nucleic acid molecules encoding SEQ ID NOs: 89-96, followed by testing of the encoded altered antibody derived by mutagenesis for retained function (i.e., the functions set forth above) using the functional assays described herein.

In other embodiments, the antibody is an IgG4 that is 60%, 70%, 80%, 90%, 95%, 96%, 97%, 98% or 99% identical to the nucleotide sequence set forth above. An IgG4 with high (i.e., 80% or greater) identity to the IgG4's of SEQ ID NOs: 85-88 respectively, can be obtained by mutagenesis (e.g., site-directed or PCR-mediated mutagenesis) of nucleic acid molecules comprising SEQ ID NOs: 85-88 followed by testing of the encoded altered antibody for retained function (i.e., the functions set forth above) using the functional assays described herein.

As used herein, the percent identity between two amino acid sequences or two nucleotide sequences is equivalent to the percent identity between the two sequences, and these terms are used interchangeably herein. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences or two nucleotide sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences or two nucleotide sequences can be determined using the Needleman and Wunsch (J. Mol, Biol. 48:444-453, 1970) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al., 1990 J.Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used.

Conditions which will permit nucleotide sequences to hybridize to the nucleotide sequences shown herein, can be determined in accordance with known techniques. Hybridization of nucleotide sequences are carried out under conditions of reduced stringency, medium stringency or even stringent conditions. Exemplary low stringency conditions are a buffer containing 35-40% formamide with 5× Denhardt's solution, 0.5% SDS and 1×SSPE at 37° C. Exemplary medium stringency conditions are a buffer containing 40-45% formamide with 5× Denhardt's solution, 0.5% SDS, and 1×SSPE at 42° C. Exemplary high stringency conditions are a buffer containing 50% formamide with 5× Denhardt's solution, 0.5% SDS and 1×SSPE at 42° C. or higher temperature, depending on the percent G+C and length of the polynucleotides. See J. Sambrook et al. (1989) *Molecular Cloning: A Laboratory Manual* ($2^{nd}$ ed.) (Cold Spring Harbor Laboratory).

Hybridization of nucleotide sequences under any of the above exemplary stringency conditions is performed in solution and collected on a filter. Alternatively, hybridization of nucleotide sequences under any of the above exemplary stringency conditions is performed in gels, e.g. Southern Blotting.

Antibodies with Conservative Modifications

In certain embodiments, an antibody of the invention has a $V_H$ region including sequences selected from the group of SEQ-ID NOs: 55-72 and a light chain variable region including sequences selected from the group of SEQ ID NOs: 31-54, such that one or more of these sequences have specified amino acid sequences based on the antibodies described herein or conservative modifications thereof, and the antibodies have the desired functional properties of the anti-c-Met antibodies of the invention. Accordingly, the invention provides an isolated antibody, or antigen binding portion thereof, having a $V_H$ chain and a $V_L$ chain such that the $V_H$ chain has amino acid sequences selected from the group of SEQ ID NOs: 55-72 and conservative modifications thereof, and the $V_L$ chain has amino acid sequences selected from the group of SEQ ID NOs: 31-54 and conservative modifications thereof; the antibody specifically binds to c-Met; and the antibody exhibits at least one of the following functional properties: the antibody activates induces internalization of the cMet receptor, the antibody inhibits binding of a protein growth factor to c-Met, with such inhibition thereby preventing activation of the receptor, e.g., preventing pathway upregulation resulting from cMet activation and/or signal transduction, or the antibody preventing or ameliorating cell proliferation, cell survival, migration, invasion or changes in morphology, or the antibody antagonizes c-Met activity, thereby preventing or ameliorating cancer such as tumor growth and or metastasis.

In an alternative embodiment, the antibody is agonistic and activates c-Met phosphorylation stimulating a cellular response.

In certain embodiments, an antibody of the invention is an Ig lambda light chain having an amino acid sequence selected from the group of SEQ ID NOs: 77-80, such that one or more of these sequences have amino acid sequences derived from the amino acid sequences of the antibodies described herein, having conservative modifications thereof, such that the derived antibodies retain the desired functional properties of the anti-c-Met antibodies of the invention. Accordingly, the invention provides an isolated parental antibody, or antigen binding portion thereof, having an Ig lambda light chain such that the Ig lambda light chain has amino acid sequences selected from the group of SEQ ID NOs: 77-80 and conservative modifications thereof; the antibody specifically binds to c-Met; and the antibody exhibits at least one of the functional antagonistic properties described herein.

In an alternative embodiment, the antibody is agonistic and activates c-Met phosphorylation stimulating a cellular response.

In other embodiments, the invention provides an antibody with an Ig kappa light chain having an amino acid sequence selected from the group of SEQ ID NOs: 81-84, such that one or more of these antibodies have an amino acid sequence derived from the antibodies described herein, having conservative modifications thereof, and wherein the antibodies demonstrate the functional properties of the parent anti-c-Met antibodies of the invention. Accordingly, the invention provides an isolated monoclonal antibody, or antigen binding portion thereof, having an Ig kappa light chain such that the Ig kappa light chain has amino acid sequences selected from the group of SEQ ID NOs: 81-84 and conservative modifications thereof; the antibody specifically binds to c-Met; and the antibody exhibits at least one of the functional properties provided herein.

In an alternative embodiment, the antibody activates c-Met phosphorylation stimulating a cellular response.

In other embodiments, an antibody of the invention is an IgG4 having an amino acid sequence selected from the group of SEQ ID NOs: 89-96, wherein one or more of these sequences has an amino acid sequence derived from a parental amino acid sequence of the antibodies described herein or conservative modifications thereof, and the antibodies demonstrate the desired functional properties of the anti-c-Met antibodies of the invention. Accordingly, the invention provides an isolated antibody, or antigen binding portion thereof in which the antibody is an IgG4, wherein: the IgG4 has an amino acid sequence selected from the group of SEQ ID NOs: 89-96 and conservative modifications thereof; the antibody specifically binds to c-Met; and the antibody exhibits at least one of the functional antagonistic properties described herein.

In an alternative embodiment, the antibody is agonistic and activates c-Met phosphorylation stimulating a cellular response.

In various embodiments, the antibody may exhibit one or more, two or more, or three or more of the antagonistic functional properties listed discussed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions as described herein. Modifications are introduced into an antibody of the invention by standard techniques known in the art, such as site-directed mutagenesis and PCR-mediated mutagenesis.

Conservative amino acid substitutions replace an amino acid residue with a different amino acid residue having a chemically and physically similar side chain. Families of amino acid residues having similar side chains are know in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Antibody Frameworks

A wide variety of antibody/immunoglobulin frameworks or scaffolds can be employed so long as the resulting polypeptide includes one or more binding region which is specific for the cMet protein of the exemplary sequences herein. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

Alternatively, known or future non-immunoglobulin frameworks and scaffolds may be employed, as long as they comprise a binding region specific for the c-Met protein. Such compounds are known herein as "polypeptides comprising a c-Met-specific binding region". Known non-immunoglobulin frameworks or scaffolds include Adnectins (fibronectin)

(Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany)), small modular immunopharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany).

Antibodies that Bind to the Same Epitope as Anti-c-Met Antibodies of the Invention In another embodiment, the invention provides antibodies that bind to the same epitope as do the various anti-c-Met antibodies of the invention provided herein. Such additional antibodies can be identified based on their ability to cross-compete (e.g., to competitively inhibit the binding of, in a statistically significant manner) with other antibodies of the invention in standard c-Met binding assays. The ability of a test antibody to inhibit the binding of antibodies having known ability to bind to human c-Met demonstrates that the test antibody can compete with that antibody. Such an antibody may, according to non-limiting theory, bind to the same or a related (e.g., a structurally similar or spatially proximal) epitope on human c-Met as the antibody with which it competes. Such antibodies can be prepared and isolated as described in the Examples.

Camelid Antibodies

Antibody proteins obtained from members of the camel and dromedary family (*Camelus bactrianus* and *Calelus dromaderius*) including new world members such as *llama species* (*Lama paccos, Lama glama* and *Lama vicugna*) have been characterized with respect to; size, structural complexity and antigenicity in human subjects. Certain IgG antibodies from this family of mammals as found in nature lack light chains, and thus have structures that are distinct from the typical four chain quaternary structure having two heavy and two light chains, characteristic of antibodies from other animals. See PCT/EP93/02214 (WO 94/04678 published 3 Mar. 1994).

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijilemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520. Engineered libraries of camelid antibodies and antibody fragments are commercially available, for example, from Ablynx, Ghent, Belgium. As is known in the art for other antibodies of non-human origin, an amino acid sequence of a camelid antibody can be altered recombinantly to obtain a sequence that more closely resembles a human sequence, i.e., the nanobody can be humanized. Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents to, detect antigens that are otherwise cryptic using classical immunological techniques, and are also useful as possible therapeutic agents. For example, yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical high molecular weight antibody.

The low molecular weight and compact size further result in camelid nanobodies being extremely thermostable, stable to extreme pH and to stable proteolytic digestion, and have low: antigenicity. Another consequence is that camelid nanobodies readily move from the circulatory system into tissues, i.e., to extravasate, and even cross the blood-brain barrier and so can be engineered to treat disorders that affect nervous tissue. Nanobodies can further facilitate drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* are expressed as fusion proteins with bacteriophage, and the proteins so expressed are functional.

Accordingly, a feature of the present invention is a camelid antibody or nanobody having high affinity for target protein c-Met. In certain embodiments herein, the camelid antibody or nanobody is naturally produced in the camelid animal, i.e., is produced by the camelid following immunization with target protein c-Met or a peptide fragment thereof, using techniques described herein for other antibodies, or is recombinantly produced in a transgenic camelid animal. Alternatively, the anti-c-Met camelid nanobody is engineered, i.e., produced by selection for example from a library of phage displaying appropriately mutagenized camelid nanobody proteins using panning procedures, with c-Met as a target as described in the examples herein. Engineered nanobodies can further be customized by genetic engineering to have a half-life in a recipient subject of from 45 minutes to two weeks.

Engineered and Modified Antibodies

An antibody of the invention can be prepared using an antibody having one or more of the $V_H$ and/or $V_L$ sequences, Ig lambda light chain sequences, or Ig Kappa light chain sequences shown herein as starting material, i.e., as a parental sequence, to engineer a derivative modified antibody, which is a modified antibody, which may have altered and improved properties compared to the starting antibody. An antibody can be engineered by modifying one or more residues within one or both variable regions (i.e., $V_H$ and/or $V_L$) or within the Ig lambda light chain only, or within the Ig kappa light chain only, within one or more CDR regions and/or within one or more framework regions. Additionally or alternatively, an antibody can be engineered by modifying residues within the constant region(s), for example to alter an effector function of the antibody.

One type of variable region engineering that can be performed is CDR grafting. Antibodies interact with target antigens predominantly through amino acid residues that are located in the heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the a naturally occurring antibody, grafted onto framework sequences from a different antibody with different properties (see, e.g., Riechmann, L. et al., 1998 Nature 332:323-327; Jones, P. et al., 1986 Nature 321:522-

525; Queen, C. et al., 1989 Proc. Natl. Acad. See. U.S.A. 86:10029-10033; U.S. Pat. No. 5,225,539 to winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference. It has been found that in certain instances it is beneficial to mutate residues within the framework regions to maintain or enhance the antigen binding ability of the antibody (see e.g., U.S. Patent Nos. 5,530, 101; 5,585,089; 5,693,762 and 6,180,370 to Queen et al).

Another type of variable region modification is mutation of amino acid residues within the $V_H$ and/or $V_L$ CDR1, CDR2 and/or CDR3 regions to thereby improve one or more binding properties (e.g., affinity of the antibody of interest, known as "affinity maturation." Site directed mutagenesis or PCR-mediated mutagenesis can be performed to introduce the mutation(s), and the consequential effect on antibody binding or on another functional property of interest is evaluated by in vitro or in vivo assays as described herein and provided in the Examples. Conservative modifications (as discussed above) can be introduced. The mutations may be amino acid substitutions, additions or deletions. Typically, no more than one, two, three, four or five residues within a CDR region are altered, although additional alterations are also envisioned.

Engineered antibodies of the invention include those in which modifications have -been made to framework residues within $V_H$ and/or $V_L$, and/or Ig lambda light chains, and/or Ig kappa light chains, e.g. to improve the properties of the antibody. Typically, such framework modifications are made to decrease the immunogenicity of the antibody. For example, one approach is to "back mutate" one or more framework residues to that of the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations are back mutated to the germline residues by, for example, site-directed mutagenesis or PCR-mediated mutagenesis. Such back mutated antibodies are also, encompassed within the invention.

Another type of framework modification involves mutating one or more residues within the framework region, or even within one or more CDR regions, to -remove T cell -epitopes to thereby reduce the potential immunogenicity of the antibody. This approach is also referred to as "deimmunization" and is described in further detail in U.S. Patent Publication No. 20030153043 by Carr et al.

In addition or alternatively to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624, 821 and 5,648,260, both by Winter et al.

In another embodiment, one or more amino acids selected from amino acid residues can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ApCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chem. 276:6591-6604). Antibodies having such modified Fc regions are within the scope of the compositions herein.

In still another embodiment, the glycosylation of an antibody is modified. For example, an aglycoslated antibody can be made (i.e., the antibody lacks glycosylation). Glycosylation can be altered to, for example, increase the affinity of the antibody for the c-Met target antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC activity of antibodies. Such carbohydrate modifications can be accomplished by, for example, expressing the antibody in a host cell with altered glycosylation enzymatic machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies' expressed in such a cell line exhibit hypofucosylation. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde-derivative of PEG, under conditions in which one or more PEG groups become covalently attached to the antibody or antibody fragment. The pegylation can be carried out by an acylation reaction or by an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-c-Met antibodies having $V_H$, $V_L$, Ig lambda light chain, or Ig kappa light chain sequences shown herein can be used to engineer additional anti-c-Met antibodies by modifying residues in the $V_H$ and/or, $V_L$, and/or Ig lambda light chains, and/or Ig kappa light chain sequences, or by modifying the constant region(s) attached thereto. Thus, in another aspect of the invention, the structural features of an anti-c-Met antibody of the invention are used to create structurally related anti-c-Met antibodies that retain at least one functional property of the parental antagonistic or agonistic antibodies of the invention, such as binding to human c-Met and also inhibiting one or more functional properties of c-Met (e.g., inducing internalization, preventing activation, e.g., an upregulation resulting from signal transduction, preventing or ameliorating cell proliferation survival, migration, invasion or changes in morphology or the antibody inhibits c-Met receptor binding preventing or ameliorating cancer such as tumor growth and or metastasis) or in the agonistic case, activating c-Met phosphorylation and stimulating a cellular response, as well as other functional properties provided herein.

For example, one or more CDR regions of the antibodies of the present invention, or mutations thereof, can be combined recombinantly with known framework regions and/or other CDRs to create additional, recombinantly-engineered, anti-c-Met antibodies of the invention, as: discussed above. Other types of modifications include those described in the previous section. The starting material for the engineering method is one or more of the $V_H$ and/or $V_L$ sequences provided herein, or one or more CDR regions thereof to be used as a parental sequence. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the nucleotide or amino acid sequence(s) is used as the starting material for mutational techniques known in the art to create a "second generation" sequence(s) derived from the original sequence(s) and then the "second generation" nucleotide sequence(s) is prepared and expressed as a protein.

Accordingly, in certain embodiments, the invention provides a method for preparing an anti-c-Met antibody having as starting parental material a $V_H$ antibody sequence having a sequence selected from the group of SEQ ID NOs: 55-72 and a $V_L$ antibody sequence having a sequence selected from the group of SEQ ID NOs: 31-54. The method involves altering at least one amino acid residue within the $V_H$ and/or $V_L$ antibody parental sequence to create at least one altered antibody sequence; and expressing the altered antibody sequence as a protein.

In other embodiments, the invention provides a method for preparing an anti-c-Met antibody comprising: an Ig lambda light chain antibody sequence having a sequence selected from the group of SEQ ID NOs: 77-80, and altering at least one amino acid residue within the Ig lambda light chain antibody sequence to create at least one altered antibody sequence; and expressing the altered antibody sequence as a protein.

In related embodiments, the invention provides a method for preparing an anti-c-Met antibody comprising: an Ig kappa light chain antibody sequence having a sequence selected from the group of SEQ ID NOs: 81-84; altering at least one amino acid residue within the Ig kappa light chain antibody sequence to create at least one altered antibody sequence; and expressing the altered antibody sequence as a protein.

The altered antibody may exhibit one or more, two or more, or three or more of the functional properties discussed herein. The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-c-Met antibody coding sequence and the resulting modified anti-c-Meet antibodies can be expressed and screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Antibodies of the Invention

The nucleotide and polypeptide sequences of the antibodies of the invention are provided below. The amino acid and nucleotide sequences of the parental, or first screen, antibodies are provided in Table A and Table C, respectfully. The amino acid and nucleotide sequences of the affinity improved antibodies as compared to the parental antibodies are provided in Table B and Table D, respectfully.

TABLE A

Amino Acid Sequences of Heavy and Light Chain Variable Regions of Parental Anti-cMet Fab Antibodies 04536 VH: [SEQ ID NO: 55]
QVQLVQSGAEVKKPGASVKVSCKASGYTFTGYYMNWVRQAPGQGLEWMGI
INPWTGNTNYAQKFQGRVTMTRDTSISTAYMELSSLRSEDTAVYYCARDP
GFFYYTPSDLWGQGTLVTVSS 04536 VL: [SEQ ID NO: 31]
DIELTQPPSVSVAPGQTARISCSGDSIGNKYVHWYQQKPGQAPVLVIYAD
SDRPSGIPERFSGSNSGNTATLTISGTQAEDE
ADYYCQAYDSSMLRVFGGGTKLTVLGQ 04687 VH: [SEQ ID NO: 58]
QVQLVQSGAEVKKPGSSVKVSCKASGGTFSSYAISWVRQAFGQGLEWMGG
IDPFGTANYAQKFQGRVTITADESTSTAYMELSSLRSEDTAVYYCARVYQ
DVWGQGTLVTVSS 04687 VL: [SEQ ID NO: 36]
DIVMTQSPDSLAVSLGERATINCRSSQSILYGINNNFLGWYQQKPGQPPK
LLIYWASTRESGVPDRFSGSGSGTDFTLTISSLQAEDVAVYYCQQYYNHP
HTFGQGTKVEIKRT 04541 VH: [SEQ ID NO: 61]
QVQLQESGPGLVKPGETLSLTCTVSGGSISSSSYYWNWIRQAPGKGLEWI
GEIYFGWTYYNPSLKGRVTISVDTSKNQFSLKLSSVTAEDTAVYYCAAGY
EFHGYTTFDYWGQGTLVTVSS 04541 VL: [SEQ ID NO: 41]
DIELTQPPSVSVAPGQTARISCSGDNIGSYYVYWYQQKPGQAPVLVIYDD
NDRPSGIPERFSGSNSGNTATLTISGTQAEDEADYYCQSYDFPSIVFGGG
TKLTVLGQ 04537 VH: [SEQ ID NO: 62]
QVQLVQSGAEVKKPGESLKISCKGSGYSFSNYWIGWVRQMPGKGLEWMGF
IFPDTSYTRYSPSFQGQVTISADKSISTAYLQWSSLASDTAMYYCARRVK
LITDYWGQGTLVTVSS 04537 VL: [SEQ ID NO: 45]
DIELTQPPSVSVAPGQTARISCSGDSLRSYFVSWYQQKPGQAPVLVIYDD
DDRPSGIPERFSGSNSGNTATLTISGTQAEDEADYYCASWDTLSDVEVFG
GGTKLTVLGQ 04690 VH: [SEQ ID NO: 63]
QVQLQQSGPGLVKPSQTLSLTCAISGDSVSSNSAAWGWIRQSPGRGLEWL
GRIYYRSKWVNDYAVSVKSRITINPDTSKNQFSLQLNSVTPEDTAVYYCA
RQGAVYPGPYGFDVWGQGTLVTVSS 04690 VL: [SEQ ID NO: 48]
DIELTQPPSVSVAPGQTARISCSGDKLGSYFVYWYQQKPGQAPVLVIYDD
DNRPSGIPERFSGSNSGNTATLTISGTQAEDEADYYCQSFGISNFYVFGG
GTKLTVLGQ

TABLE A-continued

Amino Acid Sequences of Heavy and Light Chain Variable Regions of Parental Anti-cMet Fab Antibodies 04682 VH: [SEQ ID NO: 64]
QVQLVQSGAEVKKPGESLKISCKGSGYSFTNYGIAWVRQMPGKGLEWMGI
IYPSDSYTNYSPSFQGQVTISADKSISTAYLQWSSLKASDTAMYYCARMS
YDYQHQAPSMDSWGQGTLVTVSS 04682 VL: [SEQ ID NO: 50]
DIVLTQPPSVSGAPGQRVTTSCSGSSSNIGSNYVIWYQQLPGTAPKLLIY
DDTNRPSGVPDRFSGSKSGTSASLAITGLQSEDEADYYCSTYDNYQAGWV
FGGGTKLTVLGQ

TABLE B

Amino Acid Sequences of Heavy and Light Chain Variable Regions of Affinity-Improved Anti-cMet Fab Antibodies 05078 VH: [SEQ ID NO: 56]
QVQLVQSGAEVKKPGASVKVSCKASGYTFTGYYMNWVRQAPGQGLEWMGI
IDPWNGQTNYAQKFQGRVTMTRDTSISTAYMELSSLRSEDTAVYYCARDP
GFFYYTPSDLWGQGTLVTVSS 05078 VL = 04536 VL [SEQ ID NO: 31]
DIELTQPPSVSVAPGQTARISCSGDSIGNKYVHWYQQKPGQAPVLVIYAD
SDRPSGIPERFSGSNSGNTATLTISGTQAEDEADYYCQAYDSSMLRVFGG
GTKLTVLGQ 05079 VH: [SEQ ID NO: 57]
QVQLVQSGAEVKKPGASVKVSCPCASGYTFTGYYMNWVRQAPGQGLEWNG
VIDPWNGITNYAQKFQGRVTNTRDTSISTAYMELSSLRSEDTAVYYCARD
PGFFYYTPSDLWGQGTLVTVSS 05079 VL = 04536 VL [SEQ ID NO: 31]
DIELTQPPSVSVAPGQTARISCSGDSIGNKYVHWYQQKPGQAPVLVIYAD
SDRPSGIPERFSGSNSGNTATLTISGTQAEDEADYYCQAYDSSMLRVFGG
GTKLTVLGQ 05087 VH = 04536 VH [SEQ ID NO: 55]
QVQLVQSGAEVKKPGASVKVSCKASGYTFTGYYMNWVRQAPGQGLEWMGI
INPWTGNTNYAQKFQGRVTMTRDTSISTAYMELSSLRSEDTAVYYCARDP
GFFYYTPSDLWGQGTLVTVSS 05087 VL: [SEQ ID NO: 32]
DIELTQPPSVSVAPGQTARISCSGDSIGNKYVHWYQQKPGQAPVLVIYAD
SDRPSGIPERFSGSNSGNTATLTISGTQAEDEADYYCQSYANYHDSWVFG
GGTKLTVLGQ 05088 VH = 04536 VH [SEQ ID NO: 55]
QVQLVQSGAEVKKPGASVKVSCRASGYTFTGYYMNWVRQAPGQGLEWMGI
INPWTGNTNYAQKFQGRVTMTRDTSISTAYMELSSLRSEDTAVYYCARDP
GFFYYTPSDLWGQGTLVTVSS 05088 VL: [SEQ ID NO: 33]
DIELTQPPSVSVAPGQTARISCSGDSIGNKYVSWYQQKPGQAPVLVIYAD
SDRPSGIPERFSGSNSGNTATLTISGTQAEDEADYYCQSYASDYTSWVFG
GGTKLTVLGQ 05091 VH = 04536 VH [SEQ ID NO: 55]
QVQLVQSGAEVKKPGASVKVSCKASGYTFTGYYMNWVRQAPGQGLEWMGI
INPWTGNTNAQKFQGRVTMTRDTSISTYMELSSLRSEDTAVYYCARDPGF
FYYTPSDLWGQGTLVTVSS 05091 VL: [SEQ ID NO: 34]
DIELTQPPSVSVAPGQTARISCSGDSIGNKYVHWYQQKPGQAPVLVIYAD
SDRPSGIPERFSGSNSGNTATLTISGTQAEDEADYYCQSYAHYHDIWVFG
GGTKLTVLGQ

TABLE B-continued

Amino Acid Sequences of Heavy and Light Chain Variable Regions of Affinity-Improved Anti-cMet Fab Antibodies 05092 VH = 04536 VH [SEQ ID NO: 55]
QVQLVQSGAEVKKPGASVKVSCKASGYTFTGYYMNWVRQAPGQGLEWMGI
INPWTGNTNYAQKFQGRVTMTRDTSISTAYMELSSLRSEDTAVYYCARDP
GFFYYTPSDLWGQGTLVTVSS 05092 VL: [SEQ ID NO: 35]
DIELTQPPSVSVAPGQTARISCSGDSIGNKYVHWYQQKPGQAPVLVIYAD
SDRPSGIPERFSGSNSGNTATLTISGTQAEDEADYYCQAHDSLYSRVFGG
GTKLTVLGQ 05081 VH: [SEQ ID NO: 59]
QVQLVQSGAEVKKPGSSVKVSCKASGGTFSSYAISWVRQAPGQGLEWMGG
IDPIMGTEYAQKFQGRVTITADESTSTAYMELSSLRSEDTAVYYCARVYQ
DVWGQGTLVTVSS 05081 VL = 04687 VL [SEQ ID NO: 36]
DIVMTQSPDSLAVSLGEPATINCRSSQSILYGINNNFLGWYQQKPGQPPK
LLIYWASTRESGVFDRFSGSGSGTDFTLTISSLQAEDVAVYYCQQYYNHP
HTFGQGTKVEIKRT 05082 VH: [SEQ ID NO: 60]
QVQLVQSGAEVKKPGSSVKVSCKASGGTFSSYAISWVRQAPGQGLEWMGE
IDPVIGETDYAQKFQGRVTITADESTSTAYMELSSLRSEDTAVYYCARVY
QDVWGQGTLVTVSS 05082 VL = 04687 VL [SEQ ID NO: 36]
DIVMTQSPDSLAVSLGERATINCRSSQSILYGINNNFLGWYQQKPGQPPK
LLIYWASTRESGVPDRFSGSGSGTDFTLTISSLQAEDVAVYYCQQYYNHP
STFGQGTKVEIKRT 05097 VH = 04687 VH [SEQ ID NO: 58]
QVQLVQSGAEVKKPGSSVKVSCKASGGTFSSYAISWVRQAPGQGLEWMGG
IDPFGTANYAQKFQGRVTITADESTSTAYMELSSLRSEDTAVYYCARVYQ
DVWGQGTLVTVSS 05097 VL: [SEQ ID NO: 37]
DIVMTQSPDSLAVSLGERATINCRSSQSILYGINNNFLGWYQQKPGQPPK
LLIYWASTRESGVPDRFSGSGSGTDFTLTISSLQAEDVAVYYCQQYAFGW
TFGQGTKVEIKRT 05098 VH = 04687 VH [SEQ ID NO: 58]
QVQLVQSGAEVKKPGSSVKVSCKASGGTFSSYAISWVRQAPGQGLEWMGG
IDPFGTANYAQKFQGRVTITADESTSTAYMELSSLRSEDTAVYYCARVYQ
DVWGQGTLVTVSS 05098 VL: [SEQ ID NO: 38]
DIVMTQSPDSLAVSLGERATINCRSSQSILYGINNNFLGWYQQKPGQPPK
LLIYWASTRESGVPDRFSGSGSGTDFTLTISSLQAEDVAVYYCLQYSDEP
WTFGQGTKVEIKRT 05100 VH = 04687 VH [SEQ ID NO: 58]
QVQLVQSGAEVKKPGSSVKVSCKASGGTFSSYAISWVRQAPGQGLEWMGG
IDPFGTANYAQKFQGRVTITADESTSTAYMELSSLRSEDTAVYYCARVYQ
DVWGQGTLVTVSS 05100 VL: [SEQ ID NO: 39]
DIVNTQSPDSLAVSLGERATINCRSSQSILYGINNNFLGWYQQKPGQPFK
LLIYWASTRESGVPDRFSGSGSGTDFTLTISSLQAEDVAVYYCQQYAYEP
NTFGQGTKVEIKRT 05101 VH = 04687 VH [SEQ ID NO: 58]
QVQLVQSGEVKKPGSSVKVSCKASGGTFSSYAISWVRQAPGQGLEWMGGI
DPFGTANYAQKFQGRVTITADESTSTAYMELSSLREDTAVYYCARVYQDV
WGQGTLVTVSS 05101 VL: [SEQ ID NO: 40]
DIVMTQSPDSLAVSLGETATINCRSSQSILYGINNNFLGWYQQKPGQPPK
LLIYWASTRESGVPDRFSGSGSGTDFTLTISSLQAEDVAVYYCLQYAFSP
WTFGQGTKVEIKRT 05093 VH = 04541 VH [SEQ ID NO: 61]
QVQLQESGPGLVKPGETLSLTCTVSGGSISSSSYYWNWIRQAPGKGLEWI
GEIYFGWTYYNPSLKGRVTISVDTSKNQFSLKLSSVTAEDTAVYYCARGY
EFHGYTTFDYWGQGTLVTVSS 05093 VL: [SEQ ID NO: 42]
DIELTQPPSVSVAPGQTARISCSGDNIGSYYVYWYQQKPGQAPVLVIYDD
NDRPSGIPERFSGSNSGNTATLTISGTQAEDEADYYCQSYDSYIFVFGGG
TICLTVLGQ 05094 VH = 04541 VH [SEQ ID NO: 61]
QVQLQESGPGLVKPGETLSLTCTVSGGSISSSSYYWNWIRQAPGKGLEWI
GEIYFGWTYYNPSLKGRVTISVDTSKNQFSLKLSSVTAEDTAVYYCARGY
EFHGYTTFDYWGQGTLVTVSS 05094 VL: [SEQ ID NO: 43]
DIELTQPPSVSVAPGQTARISCSGDNIGSYYVYWYQQKPGQAPVLVIYDD
NDRPSGIPERFSGSNSGNTATLTISGTQAEDEADYYCSTYDAFTFVFGGG
TKLTVLGQ 05095 VH = 04541 VH [SEQ ID NO: 61]
QVQLQESGPGLVKPGETLSLTCTVSGCSISSSSYYWNWIRQAPGKGLEWI
GEIYFGWTYYNPSLKGRVTISVDTVKNQFSLKLSSVTAEDTAVYYCARGY
EFHGYTTFDYWGQGTLVTVSS 05095 VL: [SEQ ID NO: 44]
DIELTQPPSVSVAPGQTARISCSGDNIGSYYVYWYQQKPGQAPVLVIYDD
NDRPSGIPERFSGSNSGNTATLTISGTQAEDEADYYCQSYDKYVFVFGGG
TKLTVLGQ 05102 VH = 04537 VH [SEQ ID NO: 62]
QVQLVQSGAEVKKPGESLKISCKGSGYSFSNYWIGWVRQMPGKGLEWMGF
IFPDTSYTRYSPSFQGQVTISADKSISTAYLQWSSLKASDTAMYYCARVK
LITDYWGQGTLVTVSS 05102 VL: [SEQ ID NO: 46]
DIELTQPPSVSVAPGQTARISCSGDSLRSYFVSWYQQKPGQAPVLVIYDD
DDRPSGIPERFSGSWSGNTATLTISGTQAEDEADYYCASWDPPSAFEVFG
GGTKLTVLGQ 05105 VH = 04537 VH [SEQ ID NO: 62]
QVQLVQSGAEVKKPGESLKTSCKGSGYSFSNYWIGWVRQMPGKGLEWMGF
IFPDTSYTRYSPSFQGQVTISADKSISTAYLQWSSLKASDTAMYYCARVK
LITDYWGQGTLVTVSS 05105 VL: [SEQ ID NO: 47]
DIELTQPPSVSVAPGQTARISCSGDSLRSYFVSWYQQKPGQAPVLVIYDD
DDRPSGIPERFSGSNSGNTATLTISGTQAEDEADYYCASWDNDHFEVFGG
GTKLTVLGQ 05106 VH = 04690 VH [SEQ ID NO: 63]
QVQLQQSGPGLVKPSQTLSLTCAISGDSVSSNSAAWGWIRQSPGRGLEWL
GRIYYRSKWVNDYAVSVKRITINPRTSGNQFSLQLNSVTPEDTAVYYCA
RQGAVYPGPYGFDVWGQGTLVTVSS 05106 VL: [SEQ ID NO: 49]
DIELTQPPSVSVAPGQTARISCSGDKLGSYFVYWYQQKPGQAPVLVIYDD
DNRPSGIPERFSGSNSGNTATLTISGTQAEDEADYYCGSWAYLGDVFGGG
TKLTVLGQ 05174 VH = 05078 VH [SEQ ID NO: 56]
QVQLVQSGAEVKKPGASVKVSCKASGYTFTGYYMNWVRQAPGQGLEWMGI
IDPWNGQTNYAQKFQGRVTMTRDTSISTAYMELSSLRSEDTAVYYCARDP
GFFYYTPSDLWGQGTLVTVSS 05174 VL = 05087 VL [SEQ ID NO: 51]
DIELTQPPSVSVAPGQTARISCSGDSIGNKYVHWYQQKPGQAPVLVIYAD
SDRPSGIPERFSGSNSGNTATLTISGTQAEDEADYYCQSYANYHDSWVFG
GGTKLTVLGQ

TABLE B-continued

Amino Acid Sequences of Heavy and Light Chain Variable Regions of Affinity-Improved Anti-cMet Fab Antibodies 05184 VH = 05078 VH [SEQ ID NO: 56]
QVQLVQSGAEVKKPGASVKVSCKASGYTFTGYYMNWVRQAPGQGLEWMGI
IDPWNGQTNYAQKFQGRVTMTRDTSISTAYMELSSLRSEDTAVYYCARDP
GFFYYTPSDLWGQGTLVTVSS 05184 VL = 05091 VL [SEQ ID NO: 34]
DIELTQPPSVSVAPGQTARISCSGDSIGNKYVHWYQQKPGQAPVLVIYAD
SDRPSGIPERFSGSNSGNTATLTISGTQAEDEADYYCQSYAHYHDIWVFG
GGTKLTVLGQ 05185 VH = 05081 VH [SEQ ID NO: 59]
QVQLVQSGAEVKKPGSSVKVSCKASGGTFSSYAISWVRQAPGQGLEWMGG
IDPIMGTEYAQKFQGRVTITADESTSTAYMELSSLRSEDTAVYYCARVYQ
DVWGQGTLVTVSS 05185 VL = 05100 VL [SEQ ID NO: 39]
DIVMTQSPDSLAVSLGERATINCRSSQSILYGINNNFLGWYQQKPGQPPK
LLIYWASTRESGVPDRFSGSGSGTDFTLTISSLQAEDVAVYYCQQYAYEP
NTFGQGTKVEIKRT 05186 VH = 05081 VH [SEQ ID NO: 59]
QVQLVQSGAEVKKPGSSVKVSCKASGGTFSSYAISWVRQAPGQGLEWMGG
IDPIMGTEYAQKFQGRVTITADESTSTAYMELSSLRSEDTAVYYCARVYQ
DVWGQGTLVTVSS 05186 VL = 05101 VL [SEQ ID NO: 40]
DIVMTQSPDSLAVSLGERATINCRSSQSILYGINNNFLGWYQQKPGQPFK
LLIYWASTRESGVPDRFSGSGSGTDFTLTISSLQAEDVAVYYCLQYAFSP
WTFGQGTKVEIKRT

TABLE C

Nucleotide Sequences of Heavy and Light Chain Variable Regions of Parental Anti-cMet Fab Antibodies 04536 VH: [SEQ ID NO: 21]
CAGGTGCAATTGGTTCAGAGCGGCGCGGAAGTGAAAAAACCGGGCGCGAG
CGTGAAAGTGAGCTGCAAAGCCTCCGGATATACCTTTACTGGTTATTATA
TGAATTGGGTTCGCCAAGCCCCTGGGCAGGGTCTCGAGTGGATGGGCATT
ATCAATCCGTGGACTGGCAATACGAATTACGCGCAGAAGTTTCAGGGCCG
GGTGACCATGACCCGTGATACCAGCATTAGACCGCGTATATGGAACTGAG
CAGCCTGCGTAGCGAAGATACGGCCGTGTATTATTGCGCGCGTGATCCTG
GTTTTTTTTATTATACTCCTTCTGATCTTTGGGGCCAAGGCACCCTGGTG
ACGGTTAGCTCA 04536 VL: [SEQ ID NO: 1]
GATATCGAACTGACCCAGCCGCCTTCAGTGAGCGTTGCACCAGGTCAGAC
CGCGCGTATCTCGTGTAGCGGCTATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGGCTTATGATTCTTCTATGCTTCGTGTGTTTGGCGGC
GGCACGAAGTTAACCGTTCTTGGCCAG 04687 VH: [SEQ ID NO: 24]
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCCTGGGCAGGGTCTCGAGTGGATGGGCGGT
ATCGATCCGTTTGGCACTGCGAATTACGCGCAGAAGTTTCAGGGCCGGGT
GACCATTACCGCGGATGAAAGCACCAGCACCGCGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA 04687 VL: [SEQ ID NO: 6]
GATATCGTGATGACCCAGAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT

TABLE C-continued

Nucleotide Sequences of Heavy and Light Chain Variable Regions of Parental Anti-cMet Fab Antibodies TAGCGGCTCTGGATCCGGCACTGATTTTACCCTGACCATTTCGTCCCTGC
AAGCTGAAGACGTGGCGGTGTATTATTGCCAGCAGTATTATAATCATCCT
CATACCTTTGGCCAGGGTACGAAAGTTGAAATTAAACGTACG 04541 VH: [SEQ ID NO: 27]
CAGGTGCAATTGCAAGAAGTGGTCCGGGCCTGGTGAAACCGGGCGAAACC
CTGAGCCTGACCTGCACCGTTTCCGGAGGTAGCATTTCTTCTTCTTCTTA
TTATTGGAATTGGATTCGCCAGGCCCCTGGGAAGGTCTCGAGTGGATTGG
CGAGATCTATTTTGGCTGGACCTATTATAATCCGAGCCTGAAGGCCGGGT
GACCATTAGCGTTGATACTTCGAAAAACCAGTTTAGCCTGAAACTGAGCA
GCGTGACGGCGGAAGATACGGCCGTGTATTATTGCGCGCGTGGTTATGAG
TTTCATGGTTATACTACTTTTGATTATTGGGGCCAAGGCACCCTGGTGAC
GGTTAGCTCA 04541 VL: [SEQ ID NO: 11]
GATATCGAACTGACCCAGCCGCCTTCAGTGAGCGTTGCACCAGGTCAGAC
CGCGCGTATCTCGTGTAGCGGCGATAATATTGGTTCTTATTATGTTTATT
GGTACCAGCAGAAACCCGGGCAGGCGCCAGTTCTTGTGATTTATGATGAT
AATGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGTCTTATGATTTTCCTTCATTGTGTTTGGCGGCGGC
ACGAAGTTAACCGTTCTTGGCCAG 04537 VH: [SEQ ID NO: 28]
CAGGTGCAATTGTTCAGAGCGGCGCGGAAGTGAAAAAACCGGGCGAAAG
CCTGAAAATTAGCTGCAAAGGTTCCGGATATTCCTTTTCTAATTATTGGA
TTGGTTGGGTGCGCCAGATGCCTGGGAAGGGTCTCGAGTGGATGGGCTTT
ATCTTTCCGGATACTAGCTATACCCGTTATTCTCCGAGCTTTCAGGGCCA
GGTGACCATTAGCGCGGATAAAAGCATTAGCACCGCGTATCTTCAATGGA
GCAGCCTGAAAGCGAGCGATACGGCCATGTATTATTGCGCGCGTGTTAAG
CTTATTACTGATTATTGGGGCCAAGGCACCCTGGTGACGGTTAGCTCA 04537 VL: [SEQ ID NO: 15]
GATATCGAACTGACCCAGCCGCCTTCAGTGAGCGTTGCACCAGGTCAGAC
CGCGCGTATCTCGTGTAGCGGCGATTCTCTTCGTTCTTATTTTGTTTCTT
GGTACCAGCAGAAACCCGGGCAGGCGCCAGTTCTTGTGATTTATGATGAT
GATGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCGCTTCTTGGGATACTCTTTCTGATGTTGAGGTGTTTGGC
GGCGGCACGAAGTTAACCGTTCTTGGCCAG 04690 VH: [SEQ ID NO: 29]
CAGGTGCAATTGCAACAGTCTGGTCCGGGCCTGGTGAAACCGAGCCAAAC
CCTGAGCCTGACCTGTGCGATTTCCGGAGATAGCGTGAGCTCTAATTCTG
CTGCTTGGGGTTGGATTCGCCAGTCTCCTGGGCGTGGCCTCGAGTGGCTG
GGCCGTATCTATTATCGTAGCAAGTGGGTTAACGATTATGCGGTGAGCGT
GAAAAGCCGGATTACCATCAACCCGGATACTTCGAAAAACCAGTTTAGCC
TGCAACTGAACAGCGTGACCCCGGAAGATACGGCCGTGTATTATTGCGCG
CGTCAGGGTGCTGTTTATCCTGGTCCTTATGGTTTTGATGTTTGGGGCCA
AGGCACCCTGGTGACGGTTAGCTCA 04690 VL: [SEQ ID NO: 18]
GATATCGAACTGACCCAGCCGCCTTCAGTGAGCGTTGCACCAGGTCAGAC
CGCGCGTATCTCGTGTAGCGGCGATAAGCTTGGTTCTTATTTTGTTTATT
GGTACCAGCAGAAACCCGGGCAGGCGCCAGTTCTTGTGATTTATGATGAT
GATAATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGTCTTTTGGTATTCTAATTTTTATGTGTTTGGCGGC
GGCACGAAGTTAACCGTTCTTGGCCAG 04682 VH: [SEQ ID NO: 30]
GATATCGTGCTGACCCAGCCGCCTTCAGTGAGTGGCGCACCAGGTCAGCG
TGTGACCATCTCGTGTAGCGGCAGCAGCAACATTGGTTCTAATTATG
TGATTTGGTACCAGCAGTTGCCCGGGACGGCGCCGAAACTTCTGATTTAT
GATGATACTAATCGTCCCTCAGGCGTGCCGGATCGTTTTAGCGGATCCAA
AAGCGGCACCAGCGCGAGCCTTGCGATTACGGGCCTGCAAAGCGAAGACG
AAGCGGATTATTATTGCTCTACTTATGATAATTATCAGGCTGGTTGGGTG
TTTGGCGGCGGCACGAAGTTAACCGTTCTTGGCCAG 04682 VL: [SEQ ID NO: 20]
CAGGTGCAATTGGTTCAGAGCGGCGCGGAAGTGAAAAAACCGGGCGAAAG
CCTGAAAATTAGCTGCAAAGGTTCCGGATATTCCTTTACTAATTATGGTA
TTGCTTGGGTGCGCCAGATGCCTGGGAAGGGTCTCGAGTGGATGGGCATT
ATCTATCCGTCTGATAGCTATACCAATTATTCTCCGAGCTTTCAGGGCCA

TABLE C-continued

Nucleotide Sequences of Heavy and
Light Chain Variable Regions of
Parental Anti-cMet Fab Antibodies

```
GGTGACCATTAGCGCGGATAAAAGCATTAGCACCGCGTATCTTCAATGGA
GCAGCCTGAAAGCGAGCGATACGGCCATGTATTATTGCGCGCGTATGTCT
TATGATTATCAGCATCAGGCTCCTTCTATGGATTCTTGGGGCCAAGGCAC
CCTGGTGACGGTTAGCTCA
```

TABLE D

Nucleotide Sequences of Heavy and
Light Chain Variable Regions of
Affinity-Improved Anti-cMet Fab Antibodies 05078 VH: [SEQ ID NO: 22]
```
CAGGTGCAATTGGTTCAGAGCGGCGCGGAAGTGAAAAAACCGGGCGCGAG
CGTGAAAGTGAGCTGCAAAGCCTCCGGATATACCTTTACTGGTTATTATA
TGAATTGGGTCCGCCAAGCCCCTGGGCAGGGTCTCGAGTGGATGGGCATT
ATTGATCCTTGGAATGGTCAGACTAATTATGCTCAGAAGTTTCAGGGTCG
GGTCACCATGACCCGTGATACCAGCATTAGCACCGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA
```

05078 VL = 04536 VL [SEQ ID NO: 1]
```
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGGCTTATGATTCTTCTATGCTTCGTGTGTTTGGCGGC
GGCACGAAGTTAACCGTTCTTGGCCAG
```

05079 VH: [SEQ ID NO: 23]
```
CAGGTGCAATTGGTTCAGAGCGGCGCGGAAGTGAAAAAACCGCGCGCGAG
CGTGAAAGTGAGCTGCAAAGCCTCCGGATATACCTTTACTGGTTATTATA
TGAATTGGGTCCGCCAAGCCCCTGGGCAGGGTCTCGAGTGGATGGGCGTT
ATTGATCCTTGGAATGGTATTACTAATTATGCTCAGAAGTTTCAGGGTCG
GGTCACCATGACCCGTGATACCAGCATTAGCACCGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA
```

05079 VL = 04536 VL [SEQ ID NO: 1]
```
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGGCTTATGATTCTTCTATGCTTCGTGTGTTTGGCGGC
GGCACGAAGTTAACCGTTCTTGGCCAG
```

05087 VH = 04536 VH [SEQ ID NO: 21]
```
CAGGTGCAATTGGTTCAGAGCGGCGCGGAAGTGAAAAAACCGGGCGCGAG
CGTGAAAGTGAGCTGCAAAGCCTCCGGATATACCTTTACTGGTTATTATA
TGAATTGGGTCCGCCAAGCCCCTGGGCAGGGTCTCGAGTGGATGGGCATT
ATCAATCCGTGGACTGGCAATACGAATTACGCGCAGAAGTTTCAGGGCCG
GGTGACCATGACCCGTGATACCAGCATTAGCACCGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA
```

05087 VL: [SEQ ID NO: 2]
```
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGTCTTATGCTAATTATCATGATTCTTGGGTGTTTGGC
GGCGGCACGAAGTTAACCGTTCTTGGCCAG
```

05088 VH = 04536 VH [SEQ ID NO: 21]
```
CAGGTGCAATTGGTTCAGAGCGGCGCGGAAGTGAAAAAACCGGGCGCGAG
CGTGAAAGTGAGCTGCAAAGCCTCCGGATATACCTTTACTGGTTATTATA
TGAATTGGGTCCGCCAAGCCCCTGGGCAGGGTCTCGAGTGGATGGGCATT
ATCAATCCGTGGACTGGCAATACGAATTACGCGCAGAAGTTTCAGGGCCG
```

TABLE D-continued

Nucleotide Sequences of Heavy and
Light Chain Variable Regions of
Affinity-Improved Anti-cMet Fab Antibodies

```
GGTGACCATGACCCGTGATTCCAGCATTAGCACcGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA
```

05088 VL: [SEQ ID NO: 3]
```
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGTCTTATGCTTCTGATTATACTTCTTGGGTGTTTGGC
GGCGGCACGAAGTTAACCGTTCTTGGCCAG
```

05091 VH = 04536 VH [SEQ ID NO: 21]
```
CAGGTGCAATTGGTTCAGAGCGGCGCGGAAGTGAAAAAACCGGGCGCGAG
CGTGAAAGTGAGCTGCAAAGCCTCCGGATATACCTTTACTGGTTATTATA
TGAATTGGGTCCGCCAAGCCCCTGGGCAGGGTCTCGAGTGGATGGGCATT
ATCAATCCGTGGACTGGCAATACGAATTACGCGCAGAAGTTTCAGGGCCG
GGTGACCATGACCCGTGATACCAGCATTAGCACCGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA
```

05091 VL: [SEQ ID NO: 4]
```
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGTCTTATGCTCATTATCATGATATTTGGGTGTTTGGC
GGCGGCACGAAGTTAACCGTTCTTGGCCAG
```

05092 VH = 04536 VH [SEQ ID NO: 21]
```
CAGGTGCAATTGGTTCAGAGCGGCGCGGAAGTGAAAAAACCGGGCGCGAA
AGCGTGAGTGAGCTGCAAAGCCTCCGGATATACCTTTACTGGTTATTATA
TGAATTGGGTCCGCCAAGCCCCTGGGCAGGGTCTCGAGTGGATGGGCATT
ATCAATCCGTGGACTGGCAATACGAATTACGCGCAGAAGTTTCAGGGCCG
GGTGACCATGACCCGTGATACCAGCATTAGCACCGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA
```

05092 VL: [SEQ ID NO: 5]
```
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGGCTCATGATTCTCTTTATTCTCGTGTGTTTGGCGGC
GGCACGAAGTTAACCGTTCTTGGCCAG
```

05081 VH: [SEQ ID NO: 25]
```
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCCCCAAGCCCCTGGGCAGGGTCTCGAGTGGATGGGCGTT
ATTGATCCTATTATGGGTACTGAGTATGCTCAGAAGTTTCAGGGTCGGGT
GACCATTACCGCGGATGAAAGCACCAGCACCGCGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA
```

05081 VL = 04687 VL [SEQ ID NO: 6]
```
GATATCGTGATGACCCAGAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTTCGTCCCTGC
AAGCTGAAGACGTGGCGGTGTATTATTGCCAGCAGTATTATAATCATCCT
CATACCTTTGGCCAGGGTACGAAAGTTGAAATTAAACGTACG
```

05082 VH: [SEQ ID NO: 26]
```
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCCTGGGCAGGGTCTCGAGTGGATGGGCGAG
ATTGATCCTGTTATTGGTGAGACTGATTATGCTCAGAAGTTTCAGGGTCG
```

TABLE D-continued

Nucleotide Sequences of Heavy and
Light Chain Variable Regions of
Affinity-Improved Anti-cMet Fab Antibodies GGTGACCATTACCGCGGATGAAAGCACCAGCACCGCGTATATGGAACTGA
GCAGCCTGCGTAGCGAAGATACGGCCGTGTATTATTGCGCGCGTGTTTAT
CAGGATGTTTGGGGCCAAGGCACCCTGGTGACGGTTAGCTCA 05082 VL = 04687 VL [SEQ ID NO: 6]
GATATCGTGATGACCCACAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTTCGTCCCTGC
AAGCTGAAGACGTGGCGGTGTATTATTGCCAGCAGTATTATAATCATCCT
CATACCTTTGGCCAGGGTACGAAAGTTGAAATTAAACGTACG 05097 VH = 04687 VH [SEQ ID NO: 24]
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCTGGGCAGGGTCTCGAGTGGATGGGCGGT
ATCGATCCGTTTGGCACTGCGAATTACGCGCAGAAGTTTCAGGGCGGGT
GACCATTACCGCGGATGAAAGCACCAGCACCGCGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA 05097 VL: [SEQ ID NO: 7]
GATATCGTGATGACCCAGAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTTCGTCCCTGC
AAGCTGAAGACGTGGCGGTGTATTATTGCCAGCAGTATGCTTTTGGTTGG
ACCTTTGGCCAGGGTACGAAAGTTGAAATTAAACGTACG 05098 VH = 04687 VH [SEQ ID NO: 24]
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCTGGGCAGGGTCTCGAGTGGATGGGCGGT
ATCGATCCGTTTGGCACTGCGAATTACGCGCAGAAGTTTCAGGGCCGGGT
GACCATTACCGCGGATGAAAGCACCAGCACCGCGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA 05098 VL: [SEQ ID NO: 8]
GATATCGTGATGACCCAGAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTCGTCCCTGC
AAGCTGAAGACGTGGCGGTGTATTATTGCCTTCAGTATTCTGATGAGCCT
TGGACCTTTGGCCAGGGTACGAAAGTTGAAATTAAACGTACG 05100 VH = 04687 VH [SEQ ID NO: 24]
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCTGGGCAGGGTCTCGAGTGGATGGGCGGT
ATCGATCCGTTTGGCACTGCGAATTACGCGCAGAAGTTTCAGGGCCGGGT
GACCATTACCGCGGATGAAAGCACCAGCACCGbGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA 05100 VL: [SEQ ID NO: 9]
GATATCGTGATGACCCAGAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTCGTCCCTGC
AAGCTGAAGACGTGGCGGTGTATTATTGCCAGCAGTATGCTTATGAGCCT
AATACCTTTGGCCAGGGTACGAAAGTTGAAATTAAACGTACG 05101 VH = 04687 VH [SEQ ID NO: 24]
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCTGGGCAGGGTCTCGAGTGGATGGGCGGT
ATCGATCCGTTTGGCACTGCGAATTACGCGCAGAAGTTTCAGGGCCGGGT
GACCATTACCGCGGATGAAAGCACCAGCACCGCGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA TABLE D-continued Nucleotide Sequences of Heavy and
Light Chain Variable Regions of
Affinity-Improved Anti-cMet Fab Antibodies 05101 VL: [SEQ ID NO: 10]
GATATCGTGATGACCCAGAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTTCGTCCCTGC
AAGCTGAAGACGTGGCGGTGTATTATTGCCTTCAGTATGCTTTTTCTCCT
TGGACCTTTGGCCAGGGTACGAAAGTTCAAATTAAACGTACG 05093 VH = 04541 VH [SEQ ID NO: 27]
CAGGTGCAATTGCAAGAAAGTGGTCCGGGCCTGGTGAAACCGGGCGAAAC
CCTGAGCCTGACCTGCACCGTTTCCGGAGGTAGCATTTCTTCTTCTTCTT
ATTATTGGAATTGGATTCGCCAGGCCCCTGGGAAGGGTCTCGAGTGGATT
GGCGAGATCTATTTTGGCTGGACCTATTATAATCCGAGCCTGAAAGGCCG
GGTGACCATTAGCGTTGATACTTCGAAAAACCAGTTTAGCCTGAAACTGA
GCAGCGTGACGGCGGAAGATACGGCCGTGTATTATTGCGCGCGTGGTTAT
GAGTTTCATGGTTATACTACTTTTGATTATTGGGGCCAAGGCACCCTGGT
GACGGTTAGCTCA 05093 VL: [SEQ ID NO: 12]
GATATCGAACTGACCCAGCCGCCTTCAGTGAGCGTTGCACCAGGTCAGAC
CGCGCCTATCTCGTCTAGCGGCGATAATATTGGTTCTTATTATGTTTATT
GGTACCAGCAGAAACCCGGGCAGGCGCCAGTTCTTGTGATTATGATGAT
AATGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCACTCTTATGATTCTTATATTTTTGTGTTTGGCGGCGGC
ACGAAGTTAACCGTTCTTGGCCAG 05094 VH = 04541 VH [SEQ ID NO: 27]
CAGGTGCAATTGCAAGAAAGTGGTCCGGGCCTGGTGAAACCGGGCGAAAC
CCTGAGCCTGACCTGCACCGTTTCCGGAGGTAGCATTTCTTCTTCTTCTT
ATTATTGGAATTGGATTCGCCAGGCCCCTGGGAAGGGTCTCGAGTGGATT
GGCGAGATCTATTTTGGCTGGACCTATTATAATCCGAGCCTGAAAGGCCG
GGTGACCATTAGCGTTGATACTTCGAAAAACCAGTTTAGCCTGAAACTGA
GCAGCGTGACGGCGGAAGATACGGCCGTGTATTATTGCGCGCGTGGTTAT
GAGTTTCATGGTTATACTACTTTTGATTATTGGGGCCAAGGCACCCTGGT
GACGGTTAGCTCA 05094 VL: [SEQ ID NO: 13]
GATATCGAACTGACCCAGCCGCCTTCAGTGAGCGTTGCACCAGGTCAGAC
CGCGCGTATCTCGTGTAGCGGCGATAATATTGGTTCTTATTATGTTTATT
GGTACCACCAGAAACCCGGGCAGGCGCCAGTTCTTGTGATTATGATGAT
AATGATCGTCCCTCAGGCATCCCGGAACGCTTTAGCGGATCCAACAGCGG
CAACACCGCGACCCTGACCATTAGCGGCACTCAGGCAGAAGACGAAGCGG
ATTATTATTGCTCTACTTATGATGCTTTTACTTTTGTGTTTGGCGGCGGC
ACGAAGTTAACCGTTCTTGGCCAG 05095 VH = 04541 VH [SEQ ID NO: 27]
CAGGTGCAATTGCAAGAAAGTGGTCCGGGCCTGGTGAAACCGGGCGAAAC
CCTGAGCCTGACCTGCACCGTTTCCGGAGGTAGCATTTCTTCTTCTTCTT
ATTATTGGAATTGGATTCGCCAGGCCCCTGGGAAGGGTCTCGAGTGGATT
GGCGAGATCTATTTTGGCTGGACCTATTATAATCCGAGCCTGAAAGGCCG
GGTGACCATTAGCGTTGATACTTCGAAAAACCAGTTTAGCCTGAAACTGA
GCAGCGTGACGGCGGAAGATACGGCCGTGTATTATTGCGCGCGTGGTTAT
GAGTTTCATGGTTATACTACTTTTGATTATTGGGGCCAAGGCACCCTGGT
GACGGTTAGCTCA 05095 VL: [SEQ ID NO: 14]
GATATCGAACTGACCCAGCCGCCTTCAGTGAGCGTTGCACCAGGTCAGAC
CGCGCGTATCTCGTGTAGCGGCGATAATATTGGTTCTTATTATGTTTATT
GGTACCAGCAGAAACCCGGGCAGGCGCCAGTTCTTGTGATTATGATGAT
AATGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGTCTTATGATAAAGTATGTTTTTGTGTTTGGCGGCGG
CACGAAGTTAACCGTTCTTGGCCAG 05102 VH = 04537 VH [SEQ ID NO: 28]
CAGGTGCAATTGGTTCAGAGCGGCGGAGTGAAAAAACCGGGCGAAAG
CCTGAAAATTAGCTGCAAAGGTTCCGGATATTCCTTTTCTAATTATTGGA
TTGGTTGGGTGCGCCAGATGCCTGGGAAGGGTCTCGAGTGGATGGGCTTT
ATCTTTCCGGATACTAGCTATACCCGTTATTCTCCGAGCTTTCAGGGCCA
GGTGACCATTAGCGCGGATAAAGCATTAGCACCGCGTATCTTCAATGGA
GCAGCCTGAAAGCGAGCGATACGGCCATGTATTATTGCGCGCGTGTTAAG
CTTATTACTGATTATTGGGGCCAAGGCACCCTGGTGACGGTTAGCTCA

TABLE D-continued

Nucleotide Sequences of Heavy and Light Chain Variable Regions of Affinity-Improved Anti-cMet Fab Antibodies 05102 VL: [SEQ ID NO: 16]
GATATCGAACTGACCCAGCCGCCTTCAGTGAGCGTTGCACCAGGTCAGAC
CGCGCGTATCTCGTGTAGCGGCGATTCTCTTCGTTCTTATTTTGTTTCTT
GGTACCAGCAGAAACCCGGGCAGGCGCCAGTTCTTGTGATTTATGATGAT
GATGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCGCTTCTTGGGATCCTCCTTCTGCTTTTGAGGTGTTTGGC
GGCGGCACGAAGTTAACCGTTCTTGGCCAG 05105 VH = 04537 VH [SEQ ID NO: 28]
CAGGTGCAATTGGTTCAGAGCGGCGCGGAAGTGAAAAAACCGGGCGAAAG
CCTGAAAATTAGCTGCAAAGGTTCCGGATATTCCTTTTCTAATTATTGGA
TTGGTTGGGTGCGCCAGATGCCTGGGAAGGGTCTCGAGTGGATGGGCTTT
ATCTTTCCGGATACTAGCTATACCCGTTATTCTCCGAGCTTTCAGGGCCA
GGTGACCATTAGCGCGGATAAAGCATTAGCACCGCGTATCTTCAATGGA
GCAGCCTGAAAGCGAGCGATACGGCCATGTATTATTGCGCGCGTGTTAAG
CTTATTACTGATTATTGGGGCCAAGGCACCCTGGTGACGGTTAGCTCA 05105 VL: [SEQ ID NO: 17]
GATATCGAACTGACCCAGCCGCCTTCAGTGAGCGTTGCACCAGGTCAGAC
CGCGCGTATCTCGTGTAGCGGCGATTCTCTTCGTTCTTATTTTGTTTCTT
GGTACCAGCAGAAACCCGGGCAGGCGCCAGTTCTTGTGATTTATGATGAT
GATGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCGCTTCTTGGGATAATGATCATTTTGAGGTGTTTGGCGGC
GGCACGAAGTTAACCGTTCTTGGCCAG 05106 VH = 04690 VH [SEQ ID NO: 29]
CAGGTGCAATTGCAACAGTCTGGTCCGGGCCTGGTGAAACCGAGCCAAAC
CCTGAGCCTGACCTGTGCGATTTCCGGAGATAGCGTGAGCTCTAATTCTG
CTGCTTGGGGTTGGATTCGCCAGTCTCCTGGGCGTGGCCTCGAGTGGCTG
GGCCGTATCTATTATCGTAGCAAGTGGGTTAACGATTATGCGGTGAGCGT
GAAAGCCGGATTACCATCAACCCGGATACTTCGAAAAACCAGTTTAGCC
TGCAACTGAACAGCGTGACCCCGGAAGATACGGCCGTGTATTATTGCGCG
CGTCAGGGTGCTGTTTATCCTGGTCCTTATGGTTTTGATGTTTGGGGCCA
AGGCACCCTGGTGACGGTTAGCTCA 05106 VL: [SEQ ID NO: 19]
GATATCGAACTGACCCAGCCGCCTTCAGTGAGCGTTGCACCAGGTCAGAC
CGCGCGTATCTCGTGTAGCGGCGATAAGCTTGGTTCTTATTTTGTTTATT
GGTACCAGCAGAAACCCGGGCAGGCGCCAGTTCTTGTGATTTATGATGAT
GATAATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCGGTTCTTGGGCTTATCTTGGTGATGTGTTTGGCGGCGGC
ACGAAGTTAACCGTTCTTGGCCAG 05174 VH = 05078 VH [SEQ ID NO: 22]
CAGGTGCAATTGGTTCAGAGCGGCGCGGAAGTGAAAAAACCGGGCGCGAG
CGTGAAAGTGAGCTGCAAAGCCTCCGGATATACCTTTACTGGTTATTATA
TGAATTGGGTCCGCCAAGCCCCTGGGCAGGGTCTCGAGTGGATGGGCATT
ATTGATCCTTGGAATGGTCAGACTAATTATGCTCAGAAGTTTCAGGGTCG
GGTCACCATGACCCGTGATACCAGCATTAGCACCGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA 05174 VL = 05087 VL [SEQ ID NO: 2]
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCAGTCTTATGCTAATTATCATGATTCTTGGGTGTTTGGC
GGCGGCACGAAGTTAACCGTTCTTGGCCAG 05184 VH = 05078 VH [SEQ ID NO: 22]
CAGGTGCAATTGGTTCAGAGCGGCGCGGAAGTGAAAAAACCGGGCGCGAG
CGTGAAAGTGAGCTGCAAAGCCTCCGGATATACCTTTACTGGTTATTATA
TGAATTGGGTCCGCCAAGCCCCTGGGCAGGGTCTCGAGTGGATGGGCATT
ATTGATCCTTGGAATGGTCAGACTAATTATGCTCAGAAGTTTCAGGGTCG
GGTCACCATGACCCGTGATACCAGCATTAGCACCGCGTATATGGAACTGA
GCAGCCTGCGTAGCGAAGATACGGCCGTGTATTATTGCGCGCGTGATCCT
GGTTTTTTTTATTATACTCCTTCTGATCTTTGGGGCCAAGGCACCCTGGT
GACGGTTAGCTCA 05184 VL = 05091 VL [SEQ ID NO: 4]
GATATCGAACTGACCCAGCCGCCTTCAGTGAGCGTTGCACCAGGTCAGAC
CGCGCGTATCTCGTGTAGCGGCGATTCTATTGGTAATAAGTATGTTCATT
GGTACCAGCAGAAACCCGGGCAGGCGCCAGTTCTTGTGATTTATGCTGAT
TCTGATCGTCCCTCAGGCATCCCGGAACGCTTTAGCGGATCCAACAGCGG
CAACACCGCGACCCTGACCATTAGCGGCACTCAGGCGGAAGACGAAGCGG
ATTATTATTGCCAGTCTTATGCTCATTATCATGATATTTGGGTGTTTGGC
GGCGGCACGAAGTTAACCGTTCTTGGCCAG 05185 VH = 05081 VH [SEQ ID NO: 25]
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCTGGGCAGGGTCTCGAGTGGATGGGCGGT
ATTGATCCTATTATGGGTACTGAGTATGCTCAGAAGTTTCAGGGTCGGGT
GACCATTACCGCGGATGAAAGCACCAGCACCGCGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA 05185 VL = 05100 VL [SEQ ID NO: 9]
GATATCGTGATGACCCAGAGCdCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTTCGTCCCTGC
AAGCTGAAGACGTGGCCGGTGTATTATTGCCAGCAGTATGCTTATGAGCCT
AATACCTTTGGCCAGGGTACGAAAGTTGAAATTAAACGTACG 05186 VH = 05081 VH [SEQ ID NO: 25]
CAGGTGCAATTGGTTCAGTCTGGCGCGGAAGTGAAAAAACCGGGCAGCAG
CGTGAAAGTGAGCTGCAAAGCCTCCGGAGGCACTTTTTCTTCTTATGCTA
TTTCTTGGGTGCGCCAAGCCCTGGGCAGGGTCTCGAGTGGATGGGCGGT
ATTGATCCTATTATGGGTACTGACTATGCTCAGAAGTTTCAGGGTCGGGT
GACCATTACCGCGGATGAAAGCACCAGCACCGCGTATATGGAACTGAGCA
GCCTGCGTAGCGAAGATACGGCCGTGTATTATTGCGCGCGTGTTTATCAG
GATGTTTGGGGCCAAGGCACCCTGGTGACGGTTAGCTCA 05186 VL = 05101 VL [SEQ ID NO: 10]
GATATCGTGATGACCCAGAGCCCGGATAGCCTGGCGGTGAGCCTGGGCGA
ACGTGCGACCATTAACTGCAGAAGCAGCCAGTCTATTCTTTATGGTATTA
ACAATAATTTTCTGGGTTGGTACCAGCAGAAACCAGGTCAGCCGCCGAAA
CTATTAATTTATTGGGCTTCTACTCGTGAAAGCGGGGTCCCGGATCGTTT
TAGCGGCTCTGGATCCGGCACTGATTTTACCCTGACCATTTCGTCCCTGC
AAGCTGAAGACGTGGCCGGTGTATTATTGCCTTCAGTATGCTTTTTCTCCT
TGGACCTTTGGCCAGGGTACGAAAGTTGAAATTAAACGTACG Additional related nucleotide sequences are contemplated within the scope of the invention that have, e.g., wobble base changes, optimized codon usage, optimized sequences for host expression, e.g., modifications to remove cryptic splice sequences, and conservative mutations. Additional related polypeptide sequences are contemplated within the scope of the invention that have, e.g., conservative amino acid changes, or contain additional amino acid sequences such as 6×His tags or other tags or are fused to a second polypeptide sequence, or contain residue changes that reduce immune response to the antibody therapeutic, or that have modified FR1, FR2, FR3 or FR4 residues. FR and CDR regions are provided in FIGS. 1-3. Preferred CDR sequences are as provided in the Figures.

Protein kinase dependent diseases are especially proliferative diseases, preferably a benign or especially malignant tumour, more preferably carcinoma of the brain, kidney, liver, adrenal gland, bladder, breast, stomach (especially gastric tumors), ovaries, colon, rectum, prostate, pancreas, lung, vagina, thyroid, sarcoma, glioblastomas, multiple myeloma or gastrointestinal cancer, especially colon carcinoma or colorectal adenoma, or a tumour of the neck and head, an epidermal hyperproliferation, especially psoriasis, prostate hyperplasia, a neoplasia, especially of epithelial character, preferably mammary carcinoma, or a leukaemia, especially as far as c-Met is involved. They are able to bring about the regression of tumours and to prevent the formation of tumour metastases and the growth of (also micro)metastases. In addition they can be used in epidermal hyperproliferation (e.g. psoriasis), in prostate hyperplasia, in the treatment of neoplasias, especially of epithelial character, for example mammary carcinoma, and in leukaemias. It is also possible to use the antibodies of the invention in the treatment of diseases of the immune system insofar as several or, especially, individual tyrosine protein kinases and/or (further) serine/threonine protein kinases are involved; furthermore, the antibodies of the invention can be used also in the treatment of diseases of the central or peripheral nervous system where signal transmission by at least one tyrosine protein kinase and/or (further) serine/threonine protein kinase is involved.

In certain embodiments, the antibody or functional fragment of this antibody binds the target protein c-Met and modulates, i.e., either activates or inhibits, c-Met phosphorylation. In certain embodiments, activation of c-Met phosphorylation stimulates at least one of an activity selected from the group of organ regeneration, wound healing, and tissue regeneration. In a related embodiment, the organ is skin, kidney, liver, pancreas, lung, intestine, thymus, or thyroid. In alternative embodiments, antibodies to c-Met would block pathogen infection, particularly *Listeria* infection, or ameliorate pathogenic diseases such as malaria (Carrolo, et al., Nature Med. 9: 1363-1369, 2003).

Antibodies that show inhibition of c-Met are useful in the treatment of colon cancer, including metastases, e.g. in the liver, and of non-small-cell lung carcinoma. Anti-cMet antibodies may also be used in the treatment of hereditary papillary renal carcinoma (Schmidt, L. et al. Nat. Genet. 16, 68-73, 1997) and other proliferative diseases in which c-MET is overexpressed or constitutively activated by mutations (Jeffers and Vande Woude. Oncogene 18, 5120-5125, 1999; and reference cited therein) or chromosomal rearrangements (e.g. TPR-MET; Cooper et al. Nature 311, 29-33, 1984; Park. et al. Cell 45, 895-904, 1986). Antibody antagonists of the invention are especially useful for treating an unwanted cell, in particular, a cell associated with a c-Met-related condition such as a cancer, a metastasis, or an inflammatory condition. Exemplary cancers include, but are not limited to, e.g., esophageal, breast, kidney including but not limited to papillary renal cell carcinoma, glioma, head and neck, epithelial, lung, skin, leukemia, lymphoma, myeloma, brain, pancreatic, gastric, gastrointestinal, stomach, intestine, colon, liver, genital, urinary, melanoma, and prostate. Additional cancers and conditions are provided herein or known in the art.

Further, antibodies that show antagonism of c-Met are useful in the treatment of bladder cancer (superficial and muscle invasive), breast cancer, cervical cancer, colorectal cancer, glioma (including glioblastoma, anaplastic astrocytoma, oligoastrocytoma, oligodendroglioma), esophageal cancer, gastric cancer, hepatocellular carcinoma (HCC) including childhood HCC, head and neck cancer (including head and neck squamous-cell carcinoma, nasopharyngeal-carcinoma), Hurthle cell carcinoma, malignant melanoma, mesothelioma, multiple myeloma, leukemias, non-small cell lung cancer (including all histological subtypes: adenocarcinoma, squamous cell carcinoma, bronchoalveolar carcinoma, large-cell carcinoma, and adenosquamous mixed type), small-cell lung cancer, ovarian cancer, pancreatic cancer, prostate cancer, renal cell cancer including hereditary and sporadic papillary renal cell cancer, Type I and Type II, and clear cell renal cell cancer; sarcomas, in particular osteosarcomas, clear cell sarcomas, and soft tissue sarcomas (including alveolar and embryonal rhabdomyosarcomas, alveolar soft part sarcomas); thyroid carcinoma (papillary and other subtypes).

In certain embodiments, the invention provides a method for treating a c-Met related disorder or condition, which involves administering to a subject in need thereof an effective amount of any of the above pharmaceutical compositions. The disorder or condition is a cancer or an inflammatory condition. In another related embodiment, the cancer is esophageal, breast, kidney, head and neck, epithelial, lung, leukemia, lymphoma, myeloma, brain, pancreatic, stomach, colon, liver, genital, urinary, melanoma, or prostate. In a particular embodiment the cancer is liver or esophageal.

In certain embodiments, any of the above methods involve further administering a chemotherapeutic agent. In a related embodiment, the chemotherapeutic agent is an anti-cancer agent.

In still another embodiment, the invention provides a method for treating an unwanted cell that involves contacting the cell with any of the above antibodies or functional fragments of these antibodies. In a related embodiment, the cell bears a c-Met receptor. In another related embodiment, the above method further involves treating the cell with a chemotherapeutic agent or radiation.

In an alternative embodiment, the antibody is responsive and activates c-Met phosphorylation stimulating a cellular response, such as in wound healing.

In another embodiment, the invention provides a pharmaceutical composition that includes any of the above antibodies or functional fragments of these antibodies and an additional therapeutic agent. The additional therapeutic agent is selected from the group consisting of an anti-cancer agent; an antibiotic; an anti-inflammatory agent; a growth factor; and a cytokine.

Nucleic Acid Molecules Encoding Antibodies of the Invention

Another aspect of the invention pertains to nucleic acid molecules that encode the antibodies of the invention. Examples of $V_H$ sequences are shown in SEQ ID NOs: 21-30. Examples of $V_L$ sequences are shown in SEQ ID NOs: 1-20. An example of an Ig lambda nucleotide sequence is shown in SEQ ID NO: 73. Examples of Ig kappa nucleotide sequences are shown in SEQ ID NOs: 74-76. Examples of IgG4 nucleotide sequences are shown in SEQ ID NOs: 85-88.

The nucleic acids provided herein that encode the antibodies may be present in whole cells, in a cell lysate, or may be nucleic acids in a partially purified or in a substantially pure form. A nucleic acid is isolated or rendered substantially pure when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 2006, Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene by ligating the encoding nucleotides into known vectors. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., el al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al.; 1988 Science 242:423-426; Huston et at., 1988 Proc. Natl. Acad. Sci. USA 85:5879-5883; McCafferty et al., 1990 Nature 348:552-554).

Production of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.)

In a certain embodiment, the antibodies of the invention are human monoclonal antibodies. Such human monoclonal antibodies directed against c-Met can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, production of the human antibodies of the invention can be elicited ("raised") using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-c-Met antibodies of the invention. For example, an alternative transgenic system referred to as the Xenomouse (Abgenix, Inc.) can be used; such mice are described in, for example, U.S. Pat. Nos. 5,939,598; 6,075; 181; 6,114,598; 6,150,584 and 6,162,963 to Kucherlapati et al. Moreover, alternative transchromosomic animal systems expressing human immunoglobulin genes are available in the art and can be used to raise anti-c-Met antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-c-Met antibodies of the invention.

Human antibodies or human monoclonal antibodies can also be prepared using phage display methods for screening libraries of human immunoglobulin genes. Such phage display methods for identifying and cloning human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Human Monoclonal Antibodies Against c-Met

Purified recombinant extracellular human c-Met expressed in *E. coli* (R & D Systems, Minneapolis, Minn.), or purified recombinant human c-Met conjugated to keyhole limpet hemocyanin (KLH), is used as the antigen. Other sources of expressed c-Met are also contemplated as being within the scope of the invention, including, e.g., cMet isolated from expression systems such as baculovirus, CHO cells, and other known to one skilled in the arts.

Fully human monoclonal antibodies to c-Met are prepared using HCo7, HCo12 and HCo17 strains of HuMab transgenic mice and the KM strain of transgenic transchromosomic mice, each of which express human antibody genes. In each of these mouse strains, the endogenous mouse kappa light chain gene can be homozygously disrupted as described in Chen et al., 1993 EMBO J. 12:811-820 and the endogenous mouse heavy chain gene can be homozygously disrupted as described in Example 1 of PCT Publication WO 01109187. Each of these mouse strains carries a human kappa light chain transgene, KCo5, as described in Fishwild et al., 1996 Nature Biotechnology 14:845-851. The HCo7 strain carries the HCo7 human heavy chain transgene as described in U.S. Pat. Nos. 5,545,806; 5,625,825; and 5,545,807. The HCo12 strain carries the HCo12 human heavy chain transgene as described in Example 2 of PCT Publication WO 01/09187. The HCo17 stain carries the HCo17 human heavy chain transgene. The KNM strain contains the SC20 transchromosome as described in PCT Publication WO 02/43478.

To generate fully human monoclonal antibodies to c-Met, HuMab mice and KM mice are immunized with purified recombinant c-Met extracellular domain expressed in *E. coli* or with c-Met-KLH conjugate as antigen. General immunization schemes for HuMab mice are described in Lonberg, N. et al., 1994 Nature 368(6474): 856-859; Fishwild, D. et al., 1996 Nature Biotechnology 14:845-851 and PCT Publication WO 98/24884. The mice are 6-16 weeks of age-upon the first infusion of antigen. A purified recombinant preparation (5-50 μg) of c-Met antigen (e.g., purified from transfected *E. coli* cells expressing c-Met extracellular domain) is used to immunize the HuMab mice and KM mice intraperitonealy, subcutaneously (Sc) or by footpad injection.

Transgenic mice are immunized twice with antigen in complete Freund's adjuvant or Ribi adjuvant either intraperitonealy (IP), subcutaneously (Sc) or by footpad (FP), followed by 3-21 days IP, Sc or FP immunization (up to a total of 11 immunizations) with the antigen in incomplete Freund's or Ribi adjuvant. The immune response is monitored by retro-orbital bleeds. The plasma is screened by ELISA, and mice with sufficient titers of anti-c-Met human immunoglobulin are used for fusions. Mice are boosted intravenously with antigen 3 and 2 days before sacrifice and removal of the spleen. Typically, 10-35 fusions for each antigen are performed. Several dozen mice are immunized for each antigen. A total of 82 mice of the HCo7, HCo12, HCo17 and KM mice strains are immunized with c-Met.

To select HuMab or KM mice producing antibodies that bound c-Met, sera from immunized mice can be tested by ELISA as described by Fishwild, D. et al., 1996. Briefly, in an exemplary protocol, microtiter plates are coated with purified recombinant c-Met from *E. coli* at 1-2 μg /ml in PBS, 50 μl/wells incubated 4° C. overnight then blocked with 200 μl/well of 5% chicken serum in PBS/Tween (0.05%). Other alternative concentrations and sources may also be used. Dilutions of plasma from c-Met-immunized mice are added to each well and incubated for 1-2 hours at ambient temperature. The plates are washed with PBS/Tween and then incubated with a goat-anti-human IgG Fc polyclonal antibody conjugated with horseradish peroxidase (HRP) for 1 hour at room temperature. After washing, the plates are developed with ABTS substrate (Sigma, A-1888, 0.22 mg/ml) and analyzed by spectrophotometer at a wavelength λ of 415-495 nm. Alternatively, other types of detection are possible, and may be provided be one skilled in the art. Mice that develop the highest titers of anti-c-Met antibodies are used to obtain cells for fusions. Fusions are performed and hybridoma supernatants are tested for anti-c-Met activity by ELISA.

Mouse splenocytes isolated from the HuMab mice and KM mice, are fused to a mouse myeloma cell line based upon standard protocols using PEG. The resulting hybridomas are then screened for production of antigen-specific antibodies. Single cell suspensions of splenic lymphocytes from immunized mice are fused to one-fourth the number of SP2/0 nonsecreting mouse myeloma cells (ATCC, CRL 1581) with 50% PEG (Sigma). Cells are plated at approximately $1 \times 10^5$/ well in flat bottom microtiter plate, followed by about two week incubation in selective medium containing 10% fetal bovine serum, 10% P388D 1(ATCC, CRL TIB-63) conditioned medium, 3-5% Origen® (IGEN) cloning factor in DMEM (Mediatech, CRL 10013, with high-glucose, L-glutamine and sodium pyruvate) plus 5 mM HEPES, 0.055 mM 2-mercaptoethanol, 50 mg/l gentamycin and 1×HAT (Sigma, CRL P-7185). After 1-2 weeks, cells are cultured in medium in which the HAT is replaced with HT. Individual wells are then screened by ELISA for human anti-c-Met monoclonal IgG antibodies. Once extensive hybridoma growth occurred, medium is monitored usually after 10-14 days. The antibody secreting hybridomas are replated, screened again and, if still positive for human IgG, anti-c-Met monoclonal antibodies are subcloned at least twice by limiting dilution. The stable subclones are then cultured in vitro to generate small amounts of antibody in tissue culture medium for further characterization.

Immunization of Human Ig Mice

Human Ig mice used to raise human antibodies of the invention, are immunized with a purified or enriched preparation of c-Met antigen and/or recombinant c-Met, or a c-Met fusion protein, as described by Lonberg, N. et al., 1994 Nature 368(6474): 856-859; Fishwild, D. et al., 1996 Nature Biotechnology 14: 845-851; and PCT Publication. WO 98124884 and WO 01/14424. The mice are 6-16 weeks of age upon the first infusion. For example, a purified or recombinant preparation (5-50 µg) of c-Met antigen is used to immunize the human Ig mice intraperitoneally.

Detailed procedures to generate fully human monoclonal antibodies to c-Met are described above. Cumulative experience with various antigens has shown that the transgenic mice respond when initially immunized intraperitoneally (IP) with antigen in complete Freund's adjuvant, followed by immunizations IP (up to a total of 6) with antigen in incomplete Freund's adjuvant every other week. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA, and mice with sufficient titers of anti-c-Met human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo21 strains are used. In addition, both HCo7 and HCo12 transgene can be bred together into a single mouse having two different human heavy chain transgenes (HCo7/HCo12).

Generation of Hybridomas Producing Human Monoclonal Antibodies

To generate hybridomas producing human monoclonal antibodies of the invention, splenocytes and/or lymph node cells from immunized mice are isolated and fused to an appropriate immortalized cell line, such as a mouse myeloma cell line. The resulting hybridomas are screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. In an exemplary embodiment, cells are plated in flat bottom microtiter plates, followed by a two week incubation in selective medium containing 20% fetal Clone Serum, 18% "653" conditioned media, 5% Origen® (IGEN), 4 mM L-glutamine, 1 mM sodium pyruvate, 5 mM HEPES, 0:055 mM 2-mercaptoethanol, 50 units/ml penicillin, 50 µg/ml streptomycin, 50 µg/ml gentamycin and 1×HAT (Sigma; the-HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be analyzed, usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas are grown in two-liter spinner-flasks for monoclonal antibody purification. Supernatants are filtered and concentrated before affinity chromatography with protein A-sepharose (Pharmacia, Piscataway, N.J.). Eluted IgG is checked by gel electrophoresis and high performance liquid chromatography to ensure purity. The buffer solution is exchanged to PBS, and the concentration is determined by $OD_{280}$ using extinction of an coefficient 1.43. The monoclonal antibodies are aliquoted and stored at −80° C.

Generation of Transfectomas Producing Monoclonal Antibodies

Antibodies of the invention are also produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding-heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression-vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells), including dhfr- CHO cells, described in Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Immunoconjugates

In another aspect, the present invention features an anti-c-Met antibody, or a fragment thereof, conjugated to a therapeutic moiety, such as a cytptoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytosine arabinoside, 5-fluorouracil decarbazine), ablating agents (e.g., mechlorethamine, thiotepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP)-cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating, therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G., 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including ZEVALIN™ (Ibritumomab tiuxetan, DEC Pharmaceuticals) and BEXXAR™ (iodine ($^{131}$I) tositumomab, Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or Diphtheria toxin; a protein such as tumor necrosis factor or interferon-γ; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et at., "Antibodies For Drug Delivery", in Controlled Drug Delivery (2nd Ed.), Robinson et al. (eds.), pp., 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific-molecules comprising an anti-c-Met antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule -results.

In certain embodiments, bispecific molecules are directed against other receptor tyrosine kinases, including but not limited to, e.g., cRon or EGFR, or other targets in the cMet pathway. Additional-bispecific molecule targets include receptors and ligands targeted by anti-cancer therapeutics, such as those provided herein.

Accordingly, the present invention includes bispecific molecules comprising at least one first binding specificity for c-Met and a second binding specificity for a second target epitope. For example, the second target epitope is an Fc receptor, e.g., human FcγRI (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs), and to target cells expressing c-Met. These bispecific molecules target c-Met expressing cells to effector cell and trigger Fc receptor-mediated effector cell activities, such as phagocytosis of an c-Met expressing cells, antibody dependent cell-mediated cytotoxicity (ADCC), cytokine release, or generation of superoxide anion.

Additionally, for the invention in which the bispecific molecule is multi-specific, the molecule can further include a third binding specificity, in addition to an anti-Fc binding specificity and an anti-c-Met binding specificity. For example, the third binding specificity could be an anti-enhancement factor (EF) portion, e.g., a molecule which binds to a surface protein involved in cytotoxic activity and thereby increases the immune response against the target cell. The "anti-enhancement factor portion" could be an antibody, functional antibody fragment or a ligand that binds to a given molecule, e.g., an antigen or a receptor, and thereby results in an enhancement of the effect of the binding determinants for the Fc receptor or target cell antigen.

The "anti-enhancement factor portion" can bind an Fc receptor or a target cell antigen. Alternatively, the anti-enhancement factor portion could bind to an entity that is different from the entity to which the first and second binding specificities bind. For example, the anti-enhancement factor portion can bind a cytotoxic T-cell (e.g. by CD2, CD3, CD8, CD28, CD4, CD44, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which are expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fγ receptor classes: FcγRI (CD64), FcγRII (CD32), and FcγRIII (CD 16). In another embodiment, the Fcγ receptor is a human high affinity FcγRI. Human FcγRI is a 72 kDa molecule, and has high affinity for monomeric IgG ($10^8$-$10^9$ $M^{-1}$).

The production and characterization of certain anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al., 1995 J. Immunol. 155 (10): 4996-5002 and PCT Publication WO 94/10332. The 1122 antibody producing cell line was deposited at the American Type Culture Collection under the designation HA022CL1 and has the accession no. CRL 11177.

In still other embodiments, the binding specificity for an Fc receptor is provided by an antibody that binds to a human IgA receptor, e.g., an Fc-alpha receptor FcαRI (CD89), the binding of which does not have to be blocked by human immunoglobulin A (IgA). The term "IgA receptor" is intended to include the gene product of one a gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has an inter-mediate or medium affinity ($5 \times 10^7$ M$^{-1}$) for both IgA1 and IgA2, which is increased upon exposure to cytokines such as G-CSF or GM-CSF (Morton, H.C. et al., 1996 Critical Reviews in Immunology 116:423-440). Four FcαRI-specific monoclonal antibodies, identified as A3, A59, A62 and A77, which bind FcαRI outside the IgA ligand binding domain, have been described (Monteiro, R.C. et al., 1992 J. Immunol. 148:1764).

FcαRI and FcγRI are trigger receptors for use in the bispecific molecules of the invention because they are expressed primarily on immune effector cells, e.g., monocytes, PMNs, macrophages and dendritic cells; expressed at high levels (e.g., 5,000-100,000 per cell); mediators of cytotoxic activities (e.g., ADCC, phagocytosis); mediate enhanced antigen presentation of antigens, including self-antigens, targeted to them.

Other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-c-Met binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

Antibodies are conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, genes encoding both binding specificities can be engineered into the same vector and expressed and assembled, e.g., as a fusion protein, in the same host cell. This method is particularly useful where the bispecific molecule is a mAb×mAb, mAb×Fab, Fab×F(ab')$_2$ or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub; B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Assays for Modulation of c-Met Activity (Agonism or Antagonism)

The anti-c-Met antibodies are assayed for having a c-Met agonistic or antagonistic ability. Agonism is the ability to replace the positive effector HGF by binding to and activating c-Met, for example, a human c-Met receptor carried on a cell of an established cell line in culture, or carried on a primary cell line established from a sample of human tissue, or purified c-Met protein that is commercially available (R&D Systems #358 MT) which is immobilized on an assay plate or on a bead. A measure of the agonistic activity is the concentration of the effector, in this case an antibody or antibody fragment herein, which produces 50% of control HGF activity, i.e., EC$_{50}$. The EC$_{50}$ can be determined using a ligand binding assay as determined by a standard immunological technique such as ELISA, RIA or by a cell-based assay such as cell scattering, soft agar growth and/or matrix invasion assay (tubulomorphogenesis assay). Preferably the EC$_{50}$ inhibitory activity is less than 5 μg/ml, less than 1 μg/ml, less than 0.5 μg/ml, less than 0.1 μg/ml, and even preferably less than 50 ng/ml, as measured, for example, by ELISA. Antagonism is the ability to prevent interaction with and inhibit the action of the positive effector HGF by binding to the c-Met receptor, for example, a human c-Met carried on a cell of an established cell line in culture, or carried on a primary cell line established from a sample of human tissue, or purified c-Met protein that is commercially available (R&D Systems #358 MT) which is immobilized on an assay plate or on a bead. A measure of the antagonistic activity is the concentration of the effector, in this case an antibody or antibody fragment herein, which inhibits 50% of control HGF activity, i.e., IC$_{50}$. The IC$_{50}$ can be determined using a ligand binding assay as determined by a standard immunological technique such as ELISA, RIA or by a cell-based assay such as cell scattering, soft agar growth and/or matrix invasion assay (tubulomorphogenesis assay). Preferably the IC$_{50}$ inhibitory activity is less than 5 μg/ml, less than 1 μg/ml, less than 0.5 μg/ml, less than 0.1 μg/ml, and even preferably less than 50 ng/ml, as measured, for example, by ELISA Assay of Modulation of c-Met Phosphorylation by Agonistic or Antagonistic Anti-c-Met Antibodies Agonism or antagonism by anti-c-Met antibodies of the invention is measured by activation or inhibition of c-Met phosphorylation in cells with and without stimulation with HGF. Cells of a cell line such as A549 cells are plated at a density of $3 \times 10^4$ cells per well in a total volume of 100 μl/well DMEM supplemented with 10% FBS in 96-well flat-bottom tissue culture treated plates (Costar, #3595). The plates are incubated at 37° C. in a 5% CO$_2$ atmosphere for 24 hrs, after which the medium is gently aspirated from each well of the plates and a volume of 100 μl/well DMEM added. The plates are incubated at 37° C. in a 5% CO$_2$ atmosphere for 24 hrs, after which a sample of a purified antibody to be tested, 100 μl per well of the antibody or a dilution, is added to cells in the well diluted in DMEM. As a negative control for lack of activation, a sample of an unrelated antibody (having a known specificity unrelated to c-Met epitope determinants), or buffer, is added to designated wells.

The cells are incubated at 37° C. for a short time period (e.g., 2 hours) or a longer time period (e.g., 24 hours). Where appropriate, cells are stimulated by the addition of HGF in serum-free DMEM media at a final concentration of 200 ng/well. In general, when assaying the agonistic activity of the antibodies, except for the positive control (not treated with antibody), HGF is omitted from the test sample antibody wells. In general, when assaying the antagonistic activity of the antibodies, HGF is included in the test sample antibody wells. Plates are further incubated for 10 min at 37° C., then the medium is gently aspirated from the wells of the plates. The cells are washed with cold PBS and the solution is gently aspirated from the plates. The cells are lysed with 50 μl lysis buffer (NP-40 Lysis buffer: 120 mM NaCl, 50 mM Tris-HCl pH 7.5, 1% NP-40, 1 mM EDTA, 6 mM EGTA, 20 mM NaF, 1 mM Benzamidine with freshly added 0.5 mM $Na_3VO_4$, and 0.1 mM. PMSF . The plates are shaken at room temperature for 15 minutes, and are then stored at −80° C. until needed for ELISA.

An ELISA is used to determine c-Met phosphorylation levels. For ELISA plate preparation, Nunc-Immuno™ Plate, MaxiSorb™ Surface (VWR International AG, No 391-8786) are washed twice with wash buffer (PBS-0.05% Tween Bio-rad #670-6531); and 100 μl of c-Met monoclonal capture antibody (DO-24) in PBS is added. The plates are incubated overnight at 4° C. washed three times with PBS-0.05% Tween. Non-specific binding sites are blocked with 200 μl/well 3% BSA in PBS-T for 2 hours at room temperature, with shaking. Immediately before use blocking solution in removed.

Frozen cell lysates are melted by shaking at room temperature and 40 μl of lysate is added to the Nunc-Immuno plates and the plates are incubated at 4° C. for 4 hours. The plates are washed three times with PBS-T, and 50 μl/well of 0.2 μg/ml anti-phosphotyrosine antibody PY20-HRP (ZYMED, # 03-7722) in 3% bovine serum albumin-PBS-T. The plates are incubated overnight at 4° C. and washed three times with PBS-T. The PBS-T is aspirated and 90 μl/well alkaline phosphatase substrate (CDR-Star, TROPIX, #MS100RY) added and developed while gently shaking for 45 min at room temperature. The plates are read using a 96-well plate reader.

These results demonstrate that members of the antagonistic class of anti-c-Met antibodies inhibit the ability of HGF to stimulate c-Met phosphorylation Modulation of HGF Induced Proliferation with Agonistic and Antagonistic Clones of Anti-c-Met Antibodies An assay is performed to measure the antagonistic or agonistic effect of anti-c-Met antibodies, in the absence or upon stimulation with HGF. Cells of a cell line, such as 4 MBr-5, are plated at a density of $3 \times 10^3$ cells per well in a total volume of 100 μl/well Ham's F12K supplemented with 10% FBS in 96-well flat-bottom tissue culture treated plates (Costar, #3610). The plates are incubated at 37° C. in a 5% $CO_2$ atmosphere for 2 hrs, after which 50 μl of medium containing the purified antibody to be tested is added. As a negative control for lack of modulation, a sample of an unrelated antibody (having a known specificity unrelated to c-Met epitope determinants), or buffer, is added to designated wells. The plates are incubated at 37° C. in a 5% $CO_2$ atmosphere for 1 hr, after which, 50 μl of the medium alone or 50 μl containing HGF (e.g., about 0.5 μg/μl to about 50 ng/ml) is added. The plates are incubated at 37° C. in a 5% $CO_2$ atmosphere for 72 hrs, after which BrDU incorporation is assayed using the cell proliferation ELISA, BrdU-Assay (Roche) Cat No. 1 669 915. Briefly, 20 μM/well of BrdU solution (#1) is added and the plates incubated for 22 hrs at 37° C. in a 5% $CO_2$ atmosphere. Medium is gently removed and the plate dried for 1 hr at 60° C. 200 μl of FixDenat (solution #2) is added and the plates incubated at room temperature with gentle shaking for 30 minutes. The solution is gently removed and 100 μl/well anti-BrDU working solution added. The plates are incubated at room temperature with gentle shaking for 90 minutes. The solution is gently removed and the wells washed three times with 250 μl of washing solution. The solution is gently removed and 100 μl/well substrate solution added plates are measured at A405 nm.

These results demonstrate that HGF stimulated proliferation of cells expressing c-Met levels is inhibited in cells that have been treated with antagonistic anti-c-Met antibody clones.

Modulation of c-Met-dependent Cellular Migration with an Antagonistic Class of Anti-c-Met Antibodies Cells of certain cell lines, such as NCI-H441 cells that express c-Met, are known to migrate in response to an HGF concentration gradient. Assays are performed using NCI-H441 cells where the ability of the anti-cMet antibodies to modulate migration through a perforated membrane (Boyden Chamber Assay) from an area of low HGF concentration to an area of high HGF concentration is measured.

Cellular migration is assayed using QCM™ chemotaxis 8 μM 96-well cell migration assay. Accordingly, 24 hrs prior to the assay cells are washed twice with sterile PBS and starved in the DMEM containing 1% FBS at 37° C. in a 5%. $CO_2$ atmosphere. Subsequently, the cells are trypsinised and resuspended at $1.0 \times 10^6$ cells per mL in the presence of appropriate concentration of the purified antibody for 30 min at 37° C. As a negative control for lack of modulation, a sample of an unrelated antibody (having a known specificity unrelated to c-Met epitope determinants), or buffer, is added to designated wells.

Under sterile conditions the lid of the migration chamber plate is removed and 150 μL of serum free media containing 50 ng/ml HGF (R&D Cat No. 294-HGN) is added to the wells of the feeder tray (lower chamber). 100 μL of $5-10 \times 10^4$ cells in DMEM with 1% FBS preincubated with antibody is gently added to the top chamber. The plate is covered and incubated for 16 hours at 37° C. in 4-6% $CO_2$. Following the manufacturers instructions, the cells/media in the top chamber is discarded and the chamber placed into a 96-well Feeder Tray into which 150 μL/well prewarmed-cell detachment solution has been added. Cells are dislodged by incubating for 30 minutes at 37° C. with periodic gentle agitation. Subsequently, 50 μl of prediluted CyQuant GR Dye is added to each well of the feeder tray. The plate is incubated for 15 minutes at room temperature and 150 μL of the mixture transferred to a new 96-well plate suitable for fluorescence measurement using a 480/520 nm filter set.

Data obtained show that a class of the antagonistic anti-c-Met antibody clones are capable of inhibiting a biological consequence of c-Met activation, namely, HGF stimulated migration of NCI-H441 cells through a microporous membrane.

Determination of Affinity Constants $K_D$ of Anti-c-Met Antibodies by BIACORE™

The binding affinity of purified antibody is determined using surface plasmon resonance using the BIACORE™ 3000 instrument (Pharmacia Biosensor AB, Uppsala, Sweden and Piscataway, N.J.), following the manufacturer's protocols, as described above for antagonistic antibodies.

Determination of Affinity Constants ($K_D$) of Anti-c-Met Antibodies with Flow Cytometry The binding affinity of purified antibodies for c-Met expressed on the surface of human A549 lung carcinoma cells and cynomolgus lung cells is determined by flow cytometry using the BD™. Biosciences LSR flow cytometer according to manufacturer's protocols, as described above for antagonistic antibodies.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-c-Met antibody of the present invention combined with at least one other anti-cancer or anti-inflammatory agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that does not affect the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include at least: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-c-Met antibody of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more antibodies with the same or different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-c-Met antibody of the invention results in a decrease in severity of disease symptoms, an increase in frequency and duration of disease symptom-free periods, or a prevention of impairment or disability-due to the disease affliction. Disease symptoms include standard diagnostic criteria of cancer; such as stage, size of primary tumor, member and size of metastases, or extent of inflammation.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. Nos. 5,399,163; 5,383, 851; 5,312,335; 5,064,413; 4,941,880; 4,790,824 or 4,596, 556. Examples of well known implants and modules useful in the present invention include at least: U.S. Pat. No. 4,487,603, which shows an implantable micro-infusion pump for dispensing medication at a controlled rate; U.S. Pat. No. 4,486, 194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. These patents are incorporated herein by reference. Many other such implants, delivery systems, and modules are known to those skilled in the art.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

The Combinations

The invention further relates to a method of preventing or treating proliferative diseases or diseases, such as a cancer, in a mammal, particularly a human, with a combination of pharmaceutical agents which comprises
 (a) a c-Met antibody antagonist composition; and
 (b) one or more pharmaceutically active agents.
The invention further relates to pharmaceutical compositions comprising:
 (a) a c-Met antibody antagonist composition;
 (b) a pharmaceutically active agent; and
 (c) a pharmaceutically acceptable carrier.
The present invention further relates to a commercial package or product comprising:
 (a) a pharmaceutical formulation of a c-Met antibody antagonist composition; and
 (b) a pharmaceutical formulation of a pharmaceutically active agent for simultaneous, concurrent, separate or sequential use.

The Pharmaceutically Active Agents

The term "pharmaceutically active agents" is a broad one covering many pharmaceutically active agents having different mechanisms of action. Combinations of some of these with C-Met antagonist antibodies/compositions can result in improvements in cancer therapy. Generally, pharmaceutically active agents are classified according to the mechanism of action. Many of the available agents are anti-metabolites of development pathways of various tumors, or react with the DNA of the tumor cells. There are also agents which inhibit enzymes, such as topoisomerase I and topoisomerase II, or which are anti-mitotic agents.

By the term "pharmaceutically active agent" is meant especially any pharmaceutically active agent other than a c-Met antibody antagonist composition or a derivative thereof. It includes, but is not limited to:
 i. an aromatase inhibitor;
 ii. an anti-estrogen, an anti-androgen or a gonadorelin agonist;
 iii. a topoisomerase I inhibitor or a topoisomerase II inhibitor;
 iv. a microtubule active agent, an alkylating agent, an antineoplastic anti-metabolite or a platin compound;
 v. a compound targeting/decreasing a protein or lipid kinase activity or a protein or lipid phosphatase activity, a further anti-angiogenic compound or a compound which induces cell differentiation processes;
 vi. monoclonal antibodies;
 vii. a cyclooxygenase inhibitor, a bisphosphonate, a heparanase inhibitor, a biological response modifier;
 viii. an inhibitor of Ras oncogenic isoforms;
 ix. a telomerase inhibitor;
 x. a protease inhibitor, a matrix metalloproteinase inhibitor, a methionine aminopeptidase inhibitor, or a proteasome inhibitor;
 xi. agents used in the treatment of hematologic malignancies or compounds which target, decrease or inhibit the activity of Flt-3;
 xii. an HSP90 inhibitor,
 xiii. antiproliferative antibodies;
 xiv. a histone deacetylase (HDAC) inhibitor;
 xv. a compound which targets, decreases or inhibits the activity/function of serine/threonine mTOR kinase;
 xvi. a somatostatin receptor antagonist;
 xvii. an anti-leukemic compound;
 xviii. tumor cell damaging approaches;
 xix. an EDG binder;
 xx. a ribonucleotide reductase inhibitor;
 xxi. an S-adenosylmethionine decarboxylase inhibitor;
 xxii. a monoclonal antibody of VEGF or VEGFR;
 xxiii. photodynamic therapy;
 xxiv. an angiostatic steroid;
 xxv. an implant containing corticosteroids;
 xxvi. an AT1 receptor antagonist; and
 xxvii. an ACE inhibitor.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketoconazole, vorozole, fadrozole, anastrozole and letrozole. Exemestane is marketed as AROMASIN; formestane as LENTARON; fadrozole as AFEMA; anastrozole as ARIMIDEX; letrozole as FEMARA or FEMAR; and aminoglutethimide as ORIMETEN. A combination of the invention comprising a pharmaceutically active agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered in the form as it is marketed, e.g., NOLVADEX; and raloxifene hydrochloride is marketed as EVISTA. Fulvestrant can be formulated as disclosed in U.S. Pat. No. 4,659,516 and is marketed as FASLODEX. A combination of the invention comprising a pharmaceutically active agent which is an anti-estrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and is marketed as ZOLADEX. Abarelix can be formulated, e.g., as disclosed in U.S. Pat. No. 5,843,901.

The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The term "topoisomerase II inhibitor", as used herein, includes, but is not limited to, the anthracyclines, such as doxorubicin, including liposomal formulation, e.g., CAELYX, daunorubicin, including liposomal formulation, e.g., DAUNOSOME, epirubicin, idarubicin and nemorubicin; the anthraquinones mitoxantrone and losoxantrone; and the podophillotoxines etoposide and teniposide. Etoposide is marketed as ETOPOPHOS; teniposide as VM 26-BRISTOL; doxorubicin as ADRIBLASTIN or ADRIAMYCIN; epirubicin as FARMORUBiCIN; idarubicin as ZAVEDOS; and mitoxantrone as NOVANTRON.

The term "microtubule active agent" as used herein, relates to microtubule stabilizing, microtubule destabilizing agents and microtubulin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; colchicine and epothilones and derivatives thereof, e.g., epothilone B or a derivative thereof Paclitaxel is marketed as TAXOL; docetaxel as TAXOTERE; vinblastine sulfate as VINBLASTIN R. P; and vincristine sulfate as FARMISTIN. Also included are the generic forms of paclitaxel as well as various dosage forms of paclitaxel. Generic forms of paclitaxel include, but are not limited to, betaxolol hydrochloride. Various dosage forms of paclitaxel include, but are not limited to albumin nanoparticle paclitaxel marketed as ABRAXANE; ONXOL, CYTOTAX Discodermolide can be obtained, e.g., as disclosed in U.S. Pat. No. 5,010,099. Also included are Epotholine derivatives which are disclosed in U.S. Pat. No. 6,194,181, WO 98/10121, WO 98/25929, WO 98/08849, WO 99/43653, WO 98/22461 and WO 00/31247. Especially preferred are Epotholine A and/or B.

The term "alkylating agent", as used herein, includes, but is not limited to, cyclophosphamide, ifosfamide, melphalan or nitrosourea (BCNU or Gliadel), or temozolamide (TEMODAR). Cyclophosphamide can be administered, e.g., in the form as it is marketed, e.g., under the trademark CYCLOSTIN; and ifosfamide as HOLOXAN.

The term "anti-neoplastic anti-metabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists such as, but not limited to, pemetrexed. Capecitabine can be administered, e.g., in the form as it is marketed, e.g., under the trademark XELODA; and gemcitabine as GEMZAR.

The term "platin compound", as used herein, includes, but is not limited to, carboplatin, cis-platin, cisplatinum, oxaliplatin, Satraplatin and platinum agents such as ZD0473. Carboplatin can be administered, e.g., in the form as it is marketed, e.g., CARBOPLAT; and oxaliplatin as ELOXATIN.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or theroine kinase inhibitors or lipid kinase inhibitors, for example:

i) compounds targeting, decreasing or inhibiting the activity of the vascular endothelial growth factor-receptors (VEGF), such as compounds which target, decrease or inhibit the activity of VEGF, especially compounds which inhibit the VEGF receptor, such as, but not limited to, 7H-pyrrolo[2,3-d]pyrimidine derivatives (AEE788); BAY 43-9006; isolcholine compounds disclosed in WO 00/09495 such as (4-tert-butyl-phenyl)-94-pyridin-4-yl-methyl-isoquinolin-1-yl)-amine (AAL881); and ii) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;

iii) compounds targeting, decreasing or inhibiting the activity of the fibroblast growth factor-receptors (FGFR);

iv) compounds targeting, decreasing or inhibiting the activity of the insulin-like growth factor receptor 1 (IGF-1R), such as compounds which target, decrease or inhibit the activity of IGF-1R, especially compounds which inhibit the IGF-1R receptor. Compounds include but are not limited to the compounds disclosed in WO 02/092599 and derivatives thereof of 4-amino-5-phenyl-7-cyclobutyl-pyrrolo[2,3-d]pyrimidine derivatives (AEW541);

v) compounds targeting, decreasing or inhibiting the activity of the Trk receptor tyrosine kinase family;

vi) compounds targeting, decreasing or inhibiting the activity of the Axl receptor tyrosine kinase family;

vii) compounds targeting, decreasing or inhibiting the activity of the c-Met receptor;

viii) compounds targeting, decreasing or inhibiting the activity of the Ret receptor tyrosine kinase;

ix) compounds targeting, decreasing or inhibiting the activity of the Kit/SCFR receptor tyrosine kinase;

x) compounds targeting, decreasing or inhibiting the activity of the C-kit receptor tyrosine kinases (part of the PDGFR family), such as compounds which target, decrease or inhibit the activity of the c-Kit receptor tyrosine kinase family, especially compounds which inhibit the c-Kit receptor, e.g., imatinib;

xi) compounds targeting, decreasing or inhibiting the activity of members of the c Abl family and their gene-fusion products, e.g., BCR-Abl kinase, such as compounds which target decrease or inhibit the activity of c-AbI family members and their gene fusion products, e.g., a N-phenyl-2-pyrimidine-amine derivative, e.g., imatinib, PD180970, AG957, NSC 680410 or PD173955 from ParkeDavis; BMS354825 xii) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352 or QAN697, a P13K inhibitor;

xiii) compounds targeting, decreasing or inhibiting the activity of protein-tyrosine kinase, such as imatinib mesylate (GLEEVEC™); tyrphostin or pyrymidylaminobenzamide and derivatives thereof (AMN107). A tyrphostin is preferably a low molecular weight (Mr<1500) compound, or a pharmaceutically acceptable salt thereof, especially a compound selected from the benzylidenemalonitrile class or the S arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556; AG957 and adaphostin (4-{[(2,5-dihydroxyphenyl)methyl]amino}-benzoic acid adamantyl ester, NSC 680410, adaphostin);

xiv) compounds targeting, decreasing or inhibiting the activity of the epidermal growth factor family of receptor tyrosine kinases (EGFR, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF-related ligands, and are in particular those compounds, proteins or monoclonal antibodies generically and specifically disclosed in WO 97/02266, e.g., the compound of Example 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347, e.g., compound known as CP 358774, WO 96/33980, e.g., compound ZD 1839; and WO 95/03283, e.g., compound ZM105180, e.g., trastuzumab (HERCEPTIN®), cetuximab, Iressa, OSI-774, CI 1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541, erlotinib and gefitinib. Erlotinib can be administered in the form as it is marketed, e.g. TARCEVA, and gefitinib as IRESSA, human monoclonal antibodies against the epidermal growth factor receptor including ABX-EGFR; and xv) Compounds which target, decrease or inhibit the activity/function of serine/threonine mTOR kinase are especially compounds, proteins or antibodies which target/inhibit members of the mTOR kinase family, e.g., RAD, RAD001, CCI-779, ABT578, SAR543, rapamycin and derivatives/analogs thereof, AP23573 and AP23841 from Ariad, everolimus (CERTICAN™) and sirolimus.

CERTICAN™ (everolimus, RAD) an investigational novel proliferation signal inhibitor that prevents proliferation of T-cells and vascular smooth muscle cells.

When referring to antibody, it is to include intact monoclonal antibodies, nanobodies, polyclonal antibodies, multispecific antibodies formed from at least 2 intact antibodies, and antibodies fragments so long as they exhibit the desired biological activity.

The phrase "compound which targets, decreases or inhibits the activity of a protein or lipid phosphatase" as used herein includes but is not limited to inhibitors of phosphatase 1, phosphatase 2A, PTEN or CDC25, e.g., okadaic acid or a derivative thereof.

The term "monoclonal antibodies", as used herein, includes, but is not limited to bevacizumab, cetuximab, trastuzumab, Ibritumomab tiuxetan, denosumab, anti-CD40, anti-GM-CSF, and tositumomab and iodine $I^{131}$. Bevacizumab can be administered in the form as it is marketed, e.g. AVASTIN; cetuximab as ERBITUX; trastuzumab as HERCEPTIN; Rituximab as MABTHERA; Ibritumomab tiuxetan as ZEVULIN; anti-RANKL as denosumab (AMG 162), anti-CD40 as HCD122 (U.S. patent application 2002-0106371), and tositumomab and iodine $I^{131}$ as BEXXAR.

The phrase "further anti-angiogenic compounds" includes but is not limited to compounds having another mechanism for their activity, e.g., unrelated to protein or lipid kinase inhibition, e.g., thalidomide (THALOMID) and TNP-470.

The phrase "compounds which induce cell differentiation processes" as used herein, include but is not limited to retinoic acid, α-, γ- or δ-tocopherol or α-, γ- or δtocotrienol.

The term "cyclooxygenase inhibitor" as used herein includes, but is not limited to, e.g., Cox-2 inhibitors, 5-alkyl substituted 2-arylaminophenylacetic acid and derivatives, such. as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid, lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., DIDRONEL™; "clodronic acid" as BONEFOS™; "tiludronic acid" as SKELID™; "pamidronic acid" as AREDIA™; "alendronic acid" as FOSAMAX™; "ibandronic acid" as BONDRANAT™; "risedronic acid" as ACTONEL™; and "zoledronic acid" as ZOMETA™.

The term "heparanase inhibitor", as used herein, refers to compounds which target, decrease or inhibit heparin sulphate degradation. The term includes, but is not limited to, PI 88.

The term "biological response modifier", as used herein, includes, but is not limited to lymphokine or interferons, e.g., interferon γ.

The term "inhibitor of Ras oncogenic isoforms", as used herein, includes, but is not limited to H-Ras, K-Ras or N-Ras, as used herein, refers to compounds which target, decrease or inhibit the oncogenic activity of Ras, e.g., a farnesyl transferase inhibitor (FTI), e.g., L-744832, DK8G557 or R115777 (ZARNESTRA).

The term "telomerase inhibitor", as used herein, includes, but is not limited to compounds which target, decrease or inhibit the activity of telomerase. Compounds which target, decrease or inhibit the activity of telomerase are especially compounds which inhibit the telomerase receptor, e.g., telomestatin.

The term "matrix metalloproteinase inhibitor" or (MMP inhibitor), as used herein, includes, but is not limited to, collagen peptidomimetic and non-peptidomimetic inhibitors;

tetracycline derivatives, e.g., hydroxamate peptidomimetic inhibitor batimastat; and its orally-bioavailable analogue marimastat (BB-2516), prinomastat (AG3340), metastat (NSC 683551) BMS 279251, BAY 12-9566, TAA211, MMI270B or AAJ996.

The term "methionine aminopeptidase inhibitor", as used herein, includes, but is not limited to, compounds which target, decrease or inhibit the activity of methionine aminopeptidase. Compounds which target, decrease or inhibit the activity of methionine aminopeptidase are, e.g., bengamide or a derivative thereof.

The term "proteasome inhibitors", as used herein, includes compounds which target, decrease or inhibit the activity of the proteosome. Compounds which target, decrease or inhibit the activity of the proteosome include, but are not limited to, PS-341; MLN 341. bortezomib or Velcade.

The phrase "agent used in the treatment of hematologic malignancies", as used. herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransyl-cytosine (ara-c) and bisulfan; and ALK inhibitors, e.g., compounds which target, decrease or inhibit anaplastic lymphoma kinase.

The phrase "compounds which target, decrease or inhibit the activity of Flt-3" as used herein, includes, but is not limited to compounds, proteins or antibodies which inhibit Flt-3, e.g., N-benzoyl-staurosporine, midostaurin, a staurosporine derivative, SU11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative; other geldanamycin-related compounds; radicicol and HDAC inhibitors.

The term "an antiproliferative antibody" as used herein, includes, but is not limited to trastuzumab (HERCEPTIN™TM), trastuzumab-DM1, erlotinib (TARCEVA™), bevacizumab (AVASTIN™), rituximab (RITUXAN™), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "HDAC inhibitor", as used herein relates to relates to compounds which inhibit the histone deacetylase and which possess anti-proliferative activity. This includes but is not limited to compounds disclosed in WO 02/22577, especially N-hydroxy-3-[4-[[(2-hydroxyethyl)[2-(1H-indol-3-yl)ethyl]-amino]methyl]phenyl]-2E-2-propenamide, and N-hydroxy-3-[4-[[[2-(2-methyl-1H-indol-3-yl)-ethyl]-amino]methyl]phenyl]-2E-2-propenamide and pharmaceutically acceptable salts thereof (LBH589). It further especially includes Suberoylanilide hydroxamic acid (SAHA); [4-(2-amino-phenylcarbamoyl)-benzyl]-carbamic acid pyridine-3-ylmethyl ester and derivatives thereof; butyric acid, pyroxamide, trichostatin A, Oxamflatin, apicidin, Depsipeptide; depudecin and trapoxin.

The phrase "compound which targets, decreases or inhibits the activity/function of serine/threonine mTOR kinase" as used herein, includes but is not limited to compounds, proteins or antibodies which target/inhibit members of the mTOR kinase family, e.g., RAD, RAD001, CCI-779, ABT578, SAR543, rapamycin and derivatives/analogs thereof, AP23573 and AP23841 from Ariad, everolimus (CERTICAN™) and sirolimus (RAPAMUNE™), CCI-779 and ABT578. CERTICAN™ (everolimus, RAD) an investigational novel proliferation signal inhibitor that prevents proliferation of T-cells and vascular smooth muscle cells.

The term "somatostatin receptor antagonist", as used herein, includes, but is not limited to, agents which target, treat or inhibit the somatostatin receptor, such as octreoride and SOM230.

The term "anti-leukemic compound" as used herein, includes, but is not limited to Ara-C, a pyrimidine analog, which is the 2'-α-hydroxy ribose (arabinoside) derivative of deoxycytidine. Also included is the purine analog of hypoxanthine, 6-mercaptopurine (6-MP) and fludarabine phosphate.

The phrase "tumor cell damaging approaches" refers to approaches, such as ionizing radiation. The term "ionizing radiation", referred to above and hereinafter, means ionizing radiation that occurs as either electromagnetic rays, such as X-rays and gamma rays; or particles, such. as alpha, beta and gamma particles. Ionizing radiation is provided in, but not limited to, radiation therapy and is known in the art. See Hellman, Cancer, 4th Edition, Vol. 1, Devita et al., Eds., pp. 248-275 (1993).

The term "EDG binder" as used herein, includes, but is not limited to, a class of immunosuppressants that modulates lymphocyte recirculation, such as FTY720.

The term "ribonucleotide reductase inhibitor" as used herein, includes, but is not limited to, pyrimidine or purine nucleoside analogs including, but not limited to, fludarabine and/or ara-C; 6-thioguanine; 5-FU; cladribine; 6-mercaptopurine, especially in combination with ara-C against ALL; and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL 8: See Nandy et al., Acta Oncologica, Vol. 33, No. 8, pp. 953-961 (1994).

The term "S-adenosylmethionine decarboxylase inhibitors", as used herein, includes, but is not limited to, the compounds disclosed in U.S. Pat. No. 5,461,076.

The phrase "monoclonal antibodies of VEGF or VEGFR", as used herein, includes but is not limited to, compounds disclosed in WO 98/35958, e.g., 1-(4-chloroanilino)-4-(4-pyridylmethyl)phthalazine or a pharmaceutically acceptable salt thereof, e.g., the succinate, or in WO 00/09495, WO 00/27820, WO 00/59509, WO 98/11223, WO 00/27819 and EP 0 769 947; those as described by Prewett et al., Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999) in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic, acid amides; ZD4190; ZD6474; SU5416; SU6668; bevacizumab; or anti-VEGF antibodies or anti-VEGF receptor antibodies, e.g., rhuMAb and RHUFab; VEGF aptamer, e.g., Macugon; FLT-4 inhibitors; FLT-3 inhibitors; VEGFR-2 IgG1 antibody; Angiozyme (RPI 4610); and Avastan.

The term "photodynamic therapy", as used herein, refers to therapy which uses certain chemicals known as photosensitizing agents to treat or prevent cancers. Examples of photodynamic therapy include, but are not limited to, treatment with agents, such as, e.g., VISUDYNE and porfimer sodium.

The term "angiostatic steroid", as used herein, includes, but is not limited to agents which block or inhibit angiogenesis, such as, e.g., anecortave, triamcinolone, hydrocortisone, 11-β-epihydrocotisol, cortexolone, 17 β-hydroxyprogesterone, corticosterone, desoxycorticosterone, testosterone, estrone and dexamethasone.

The phrase "Implant containing corticosteroids" as used herein, includes, but is not limited to agents, such as, e.g., fluocinolone and dexamethasone.

The term "AT1 receptor-antagonist" as used herein, includes, but is not limited to agents, such as DIOVAN.

The term "ACE inhibitor" as used herein, includes, but is not limited to CIBACEN, benazopril, enazepril (LOTENSIN), captopril, enalapril, fosinopril, lisinopril, moexipril, quinapril, ramipril, perindopril and trandolapril.

Other pharmaceutically active agents include, but are not limited to, plant alkaloids, hormonal agents and antagonists, biological response modifiers, preferably lymphokines or interferons, antisense oligonucleotides or oligonucleotide derivatives; or miscellaneous agents or agents with other or unknown mechanism of action.

In each case where citations of patent applications or scientific publications are given, in particular with regard to the respective compound claims and the final products of the working examples therein, the subject matter of the final products, the pharmaceutical preparations and the claims is hereby incorporated into the present application by reference to these publications. Comprised are likewise the corresponding stereoisomers, as well as the corresponding crystal modifications, e.g., solvates and polymorphs, which are disclosed therein. The compounds used as active ingredients in the combinations disclosed herein can be prepared and administered as described in the cited documents, respectively.

The structure of the active agents identified by code numbers, generic or trade names may be taken from the actual edition of the standard compendium "The Merck Index" or from databases, e.g., Patents International, e.g., IMS World Publications, or the publications mentioned above and below. The corresponding content thereof is hereby incorporated by reference.

It will be understood that references to the components (a) and (b) are meant to also include the pharmaceutically acceptable salts of any of the active substances. If active substances comprised by components (a) and/or (b) have, for example, at least one basic center, they can form acid addition salts. Corresponding acid addition salts can also be formed having, if desired, an additionally present basic center. Active substances having an acid group, e.g., COOH, can form salts with bases. The active substances comprised in components (a) and/or (b) or a pharmaceutically acceptable salts thereof may also be used in form of a hydrate or include other solvents used for crystallization.

Thus, in a first aspect, the present invention relates to a method for the prevention of. treatment of proliferative diseases or diseases that are triggered by persistent angiogenesis in a mammal, preferably a human patient, which comprises treating the patient concurrently or sequentially with pharmaceutically effective amounts of a combination of:
  (a) a c-Met antibody antagonist composition; and
  (b) an pharmaceutically active agent.

In preferred embodiment, the present invention provides a pharmaceutical preparation comprising:
  (a) a c-Met antibody antagonist composition; and
  (b) one or more pharmaceutically active agents selected from the group consisting of an aromatase inhibitor; an antiestrogen; an anti-androgen; a gonadorelin agonist; a topoisomerase I inhibitor; a topoisomerase II inhibitor; a microtubule active agent, an alkylating agent; an antineoplastic anti-metabolite; a platin compound; a compound targeting/decreasing a protein or lipid, kinase activity or a protein or lipid phosphatase activity, a anti-angiogenic compound; a compound which induces cell differentiation processes; monoclonal antibodies; a cyclooxygenase inhibitor; a bisphosphonate; a heparanase inhibitor; a biological response modifier; an inhibitor of Ras oncogenic isoforms; a telomerase inhibitor; a protease inhibitor, a matrix metalloproteinase inhibitor, a methionine aminopeptidase inhibitor; a proteasome inhibitor; agents which target, decrease or inhibit the activity of Flt-3; an HSP90 inhibitor; antiproliferative antibodies; an HDAC inhibitor; a compound which targets, decreases. or inhibits the activity/function of serine/threonine mTOR kinase; a somatostatin receptor antagonist; an anti-leukemic compound; tumor cell damaging approaches; an EDG binder; a ribonucleotide reductase inhibitor; an S-adenosylmethionine decarboxylase inhibitor; a monoclonal antibody of VEGF or VEGFR; photodynamic therapy; an Angiostatic steroid; an implant containing corticosteroids; an AT1 receptor antagonist; and an ACE inhibitor.

Any of the combination of components (a) and (b), the method of treating a warm-blooded animal comprising administering these two components, a pharmaceutical composition comprising these two components for simultaneous, separate or sequential use, the use of the combination for the delay of progression or the treatment of a proliferative disease or for the manufacture of a pharmaceutical preparation for these purposes or a commercial product comprising such a combination of components (a) and (b), all as mentioned or defined above, will be referred to subsequently also as combination of the invention (so that this term refers to each of these embodiments which thus can replace this term where appropriate).

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one-time point, other components at a different time point, that is, in a chronically staggered manner, preferably such that the combination shows more efficiency than the single compounds administered independently (especially showing synergism). Separate use (administration) preferably means administration of the components of the combination independently of each other at different time points, preferably meaning that the components (a) and (b) are administered such that no overlap of measurable blood levels of both compounds are present in an overlapping manner (at the same time).

Also combinations of two or more of sequential, separate and simultaneous. administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

"Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction point therapeutic effect). Whether this is the case, can inter alia be determined by following the blood levels, showing that both compounds are present in the blood of the human to be treated at least during certain time intervals.

"Pharmaceutically effective" preferably relates to an amount that is therapeutically or in a broader sense also prophylactically effective against the progression of a proliferative disease.

The term "a commercial package" or "a product", as used herein defines especially a "kit of parts" in the sense that the components (a) and (b) as defined above can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) (as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either-chronically, e.g., more than 3-4 weeks of daily dosing, at a later time point and subsequently the other component or the combination of both components at a still later time point (in subsequent drug combination treatment courses for an optimal anti-tumor effect) or the like.

The COMBINATION OF THE INVENTION can also be applied in combination with other treatments, e.g., surgical intervention, hyperthermia and/or irradiation therapy.

The pharmaceutical compositions according to the present invention can be prepared by conventional means and are those suitable for enteral, such as oral or rectal, and parenteral administration to mammals including man, comprising a therapeutically effective amount of a VEGF inhibitor and at least one pharmaceutically active agent alone or in combination with one or more pharmaceutically acceptable carriers, especially those suitable for enteral or parenteral application.

The pharmaceutical compositions comprise from about 0.00002 to about 100%, especially, e.g., in the case of infusion dilutions that are ready for use, of 0.0001 to 0.02%, or, e.g., in case of injection or infusion concentrates or especially parenteral formulations, from about 0.1% to about 95%, preferably from about 1% to about 90%, more preferably from about 20% to about 60% active ingredient (weight by weight, in each case). Pharmaceutical compositions according to the invention may be, e.g., in unit dose form, such as in the form of ampoules, vials, dragées, tablets, infusion bags or capsules.

The effective dosage of each of the combination partners employed in a formulation of the present invention may vary depending on the particular compound or pharmaceutical compositions employed, the mode of administration, the condition being treated and the severity of the condition being treated. A physician, clinician or veterinarian of ordinary skill can readily determine the effective amount of each of the active ingredients necessary to prevent, treat or inhibit the progress of the condition.

Tyrphostins, especially Adaphostin, are preferably administered to a warm-blooded animal, especially a human in a dosage in the range of about 1-6000 mg/day, more preferably 25-5000 mg/day, most preferably 50-4000 mg/day. Unless stated otherwise herein, the compound is preferably administered from one to 5, especially from 1-4 times per day.

Pharmaceutical preparations for the combination therapy for enteral or parenteral administration are, e.g., those in unit dosage forms, such as sugar-coated tablets, capsules or suppositories, and furthermore ampoules. If not indicated otherwise, these formulations are prepared by conventional means, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units. One of skill in the art has the ability to determine appropriate pharmaceutically effective amounts of the combination components.

Preferably, the compounds or the pharmaceutically acceptable salts thereof, are administered as an oral pharmaceutical formulation in the form of a tablet, capsule or syrup; or as parenteral injections if appropriate.

In preparing compositions for oral administration, any pharmaceutically acceptable media may be employed such as water, glycols, oils, alcohols, flavoring agents, preservatives, coloring agents. Pharmaceutically acceptable carriers include starches, sugars, microcrystalline celluloses, diluents, granulating agents, lubricants, binders, disintegrating agents.

Solutions of the active ingredient, and also suspensions, and especially isotonic aqueous solutions or suspensions, are useful for parenteral administration of the active ingredient, it being possible, e.g., in the case of lyophilized compositions that comprise the active ingredient alone or together with a pharmaceutically acceptable carrier, e.g., mannitol, for such solutions or suspensions to be produced prior to use. The pharmaceutical compositions may be sterilized and/or may comprise excipients, e.g., preservatives, stabilizers, wetting and/or emulsifying agents, solubilizers, salts for regulating the osmotic pressure and/or buffers, and are prepared in a manner known per se, e.g., by means of conventional dissolving or lyophilizing processes. The solutions or suspensions may comprise viscosity-increasing substances, such as sodium carboxymethylcellulose, carboxymethylcellulose, dextran, polyvinylpyrrolidone or gelatin. Suspensions in oil comprise as the oil component the vegetable, synthetic or semi-synthetic oils customary for injection purposes.

The isotonic agent may be selected from any of those known in the art, e.g. mannitol, dextrose, glucose and sodium chloride. The infusion formulation may be diluted with the aqueous medium. The amount of aqueous medium employed as a diluent is chosen according to the desired concentration of active ingredient in the infusion solution. Infusion solutions may contain other excipients commonly employed in formulations to be administered intravenously such as antioxidants.

The present invention further relates to "a combined preparation", which, as used herein, defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g., in order to cope with the needs of a patient sub-population to be treated or the needs of the single patient based on the severity of any side effects that the patient experiences.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders. The term "subject" as used herein in intended to include human and non-human animals. Non-human animals include all vertebrates, e.g., mammals, such as non-human primates, sheep, dogs, cats, cows, horses, chickens, and non-mammals, such as birds, amphibians and reptiles. The methods are particularly suitable for treating human patients having a disorder associated with aberrant c-Met expression. When antibodies to c-Met are administered together with another agent, the two can be administered in either order or simultaneously.

In one embodiment, the antibodies (and immunoconjugates and bispecific molecules) of the invention can be used to detect levels of c-Met, or levels of cells that contain c-Met. This can be achieved, for example, by contacting a sample (such as an in vitro sample) and a control sample with the anti-c-Met antibody under conditions that allow for the formation of a complex between the antibody and c-Met. Any complexes formed between the antibody and c-Met are detected and compared in the sample and the control. For example, standard detection methods, well known in the art, such as ELISA and flow cytometric assays, can be performed using the compositions of the invention.

Accordingly, in one aspect, the invention further provides methods for detecting the presence of c-Met (e.g., human c-Met antigen) in a sample, or measuring the amount of c-Met, comprising contacting the sample, and a control sample, with an antibody of the invention, or an antigen binding portion thereof, which specifically binds to c-Met, under conditions that allow for formation of a complex between the antibody or portion thereof and c-Met. The formation of a complex is then detected, wherein a difference in complex formation between the sample compared to the control sample is indicative of the presence of c-Met in the sample.

Also within the scope of the invention are kits consisting of the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

EXAMPLES

Example 1

Generation of Human c-Met-specific Antibodies from the HuCAL GOLD® Library

Therapeutic antibodies against human c-Met protein are generated by selection of clones having high binding affinities, using as the source of antibody variant proteins in a commercially available phage display library, the MorphoSys HuCAL GOLD® Fab library. HuCAL GOLD® is a Fab library (Knappik et al., 2000 J. Mol. Biol. 296:57-86; Krebs et al., 2001 J Immunol. Methods 254:67-84; Rauchenberger et al., 2003 J Biol Chem. 278(40):38194-38205), in which all CDRs are diversified by appropriate mutation, and which employs the CysDisplay™ phage display technology for linking Fab fragments to the phage surface (WO 01/05950 Löhning 2001).

The HuCAL GOLD® library is amplified in standard rich bacterial medium (2×YT) containing 34 μg/ml chloramphenicol and 1% glucose (2×YT-CG). After infection of cells at an $OD_{600\,nm}$ of 0.5 with VCSM13 helper phages (incubating the mix of cells and phage for 30 min at 37° C. without shaking followed by 30 min at 37° C. shaking at 250 rpm), cells are centrifuged (4120 g; 5 min; 4° C.), are resuspended in 2×YT/34 μg/ml chloramphenicol/50 μg/ml kanamycin/ 0.25 mM IPTG, and are grown overnight at 22° C. At the end of this period cells are removed by centrifugation, and phages are PEG-precipitated twice from the supernatant, are resuspended in PBS/20% glycerol and are stored at −80° C.

Phage amplification between two panning rounds is conducted as follows: mid-log phase *E. coli* strain TG1 cells are infected with phages that are eluted following the selection with c-Met protein, and are plated onto LB-agar supplemented with 1% of glucose and 34 μg/ml of chloramphenicol (LB-CG plates). After overnight incubation of the plates at 30° C., bacterial colonies are scraped off the agar surface, and used to inoculate 2×YT-CG broth to obtain an $OD_{600\,nm}$ of 0.5, then VCSM13 helper phages are added to obtain a productive infection as described above.

Pre-experiments for Solution Panning Using Strep-Tactin Magnetic Beads

The Strep-tag II has been reported to have low affinity for the Strep-Tactin matrix ($K_D \sim 1$ μM according to (Voss and Skerra, 1997 Protein Eng. 10:975-982), therefore, a pre-experiment is performed to assess the suitability of using Strep-Tactin-coated MagStrep beads for the capturing of the antigen during the antibody selections, and to avoid antigen loss during the pannings.

For that purpose, 8 mg of MagStrep beads is incubated with 46 μg of His-Strep-tagged c-Met for 1 h at room temperature and the sample is divided into four pre-blocked Eppendorf tubes. One tube serves as the positive control (no washing) and the other three samples are washed with different stringencies according to the HuCAL GOLD® manual panning section. Detection of binding of the His-Strep-tagged c-Met to the MagStrep beads (Strep-Tactin coated Magnetic beads obtained from IBA, Göttingen, Germany) is performed in BioVeris using a goat anti-c-Met antibody and a Rubidium-labeled anti-goat detection antibody.

As shown in the figures herein, no significant loss of His-Strep-tagged c-Met from the Strep-Tactin-coated beads is detectable when the non-washed beads are compared with those beads washed with different HuCAL® stringencies. Thus, the His-Strep-tagged c-Met seems to be suitable for the use in the solution pannings with Strep-Tactin-coated magnetic beads (MagStrep beads).

Selection by Panning of c-Met-specific Antibodies from the Library

For the selection of antibodies recognizing human c-Met, two panning strategies are applied.

Generally, HuCAL GOLD® phage-antibodies are divided into four pools comprising different combinations of $V_H$ master genes (pool 1 contained VH1/5λκ; pool 2 contained $V_H 3 \lambda \kappa$; pool 3 contained $V_H 2/4/6 \lambda \kappa$; and pool 4 contained $V_H 1$-6λκ). These pools are individually subjected to two rounds of solution panning on His-Strep-tagged c-Met captured onto StrepTactin magnetic beads (Mega Strep beads; IBA), and for the third selection round only, either on His-Strep-tagged c-Met captured onto StrepTactin magnetic beads or on APP-tagged human c-Met protein captured by Streptavidin beads (Dynabeads® M-280 Streptavidin; Dynal) with a biotinylated anti-APP antibody.

Specifically, for the solution panning using His-Strep-tagged c-Met coupled to StrepTactin magnetic beads, the following protocol is applied: pre-blocked tubes are prepared (1.5 ml Eppendorf tubes) by treatment with 1.5 ml 2× ChemiBLOCKER diluted 1:1 with PBS over night at 4° C. Pre-blocked beads are prepared by treatment as follows: 580 μl (28 mg beads) StrepTactin magnetic beads are washed once with 580 μl PBS and resuspended in 580 μl 1× ChemiBLOCKER (diluted in one volume 1×PBS). Blocking of the beads is performed in the pre-blocked tubes over night at 4° C.

Phage particles diluted in PBS to a final volume of 500 μl for each panning condition are mixed with 500 μl 2× ChemiBLOCKER/0.1% Tween and kept for one hour at room temperature on a rotating wheel. Pre-adsorption of phage particles for removal of StrepTactin or beads-binding phages is performed twice: 160 μl of blocked StrepTactin magnetic beads (4 mg) is added to the blocked phage particles, and is incubated for 30 min at room temperature on a rotating wheel. After separation of the beads by a magnetic device (Dynal MPC-E), the phage supernatant (~1.1 ml) is transferred to a fresh, blocked reaction tube and pre-adsorption is repeated using 160 μl blocked beads for 30 min. Then, His-Strep-tagged c-Met, either 400 nM or 100 nM, is added to the blocked phage particles in a fresh, blocked 1.5 ml reaction tube and the mixture is incubated for 60 min at room temperature on a rotating wheel.

The phage-antigen complexes are captured using either 320 μl or 160 μl of blocked StrepTactin magnetic beads added to the 400 nM or the 100 nM phage panning pools, respectively, which is then incubated for 20 min at room temperature on a rotating wheel. Phage particles bound to the StrepTactin magnetic beads are again collected with the magnetic particle separator.

Beads are then washed seven times with PBS/0.05% Tween (PBST), followed by washing another three times with PBS only. Elution of phage particles from the StrepTactin magnetic beads is performed by addition of 200 μl 20 mM DTT in 10 mM Tris-HCl, pH 8.0 to each tube for 10 min. The eluate is collected, and the beads are washed once with 200 μl PBS and the PBS eluate is added to the DTT eluate. This eluate sample is used to infect 14 ml of an E. coli TG-1 culture that are previously grown to an $OD_{600\ nm}$ of 0.6-0.8.

After infection and subsequent centrifugation for 10 min at 5000 rpm, each bacterial pellet is resuspended in 500 μl 2×YT medium, plated onto 2×YT-CG agar plates and incubated overnight at 30° C. The next morning, the resulting colonies are scraped off the plates and the phage is prepared by rescue and amplification as described above.

The second round of solution pannings on His-Strep-tagged c-Met is performed according to the protocol of the first round, except that decreasing amounts of antigen are used (50 nM, and 10 nM) and the stringency of the washing procedure is altered appropriately.

Two different panning strategies are applied for the third selection round: the amplified phage output of the second panning round is split and subjected to two different panning conditions. The first half of the phage output is used for the standard panning strategy on human His-Strep-tagged c-Met captured onto StrepTactin beads as described above (antigen amounts are 10 nM or 1 nM, respectively).

The second panning variation for the third selection round is performed on human APP-tagged c-Met. APP-tagged c-Met protein at a final concentration of 50 nM or 10 nM is mixed with 1 ml of pre-cleared, second round phage particles, and the mixture is incubated at room temperature for 1 hour on a rotating wheel. In parallel, 8 mg pre-blocked Dypabeads M-280 Streptavidin (Dynal) is incubated with 40 μg biotinylated mouse anti-APP antibody for 30 min at room temperature on a rotating wheel followed by two washing steps with PBST. The pre-formed complexes consisting of phage-antibodies bound to APP-tagged c-Met are captured by the anti-APP coated M-280 Streptavidin magnetic beads for 30 min at room temperature. Phage elution and amplification are performed as described above.

Subcloning and Expression of Soluble Fab Fragments

The Fab-encoding inserts of the selected HuCAL GOLD® phagemids are subcloned into expression vector pMORPH®X9_Fab_FH (see figures), in order to facilitate rapid and efficient expression of soluble Fabs. For this purpose, the plasmid DNA of the selected clones is digested with restriction enzyme endonucleases XbaI and EcoRI, thereby excising the Fab-encoding insert (ompA-VLCL and phoA-Fd). This insert as then cloned into XbaI/EcoRI-digested expression vector pMORPHG®X9_Fab_FH.

Fab proteins are expressed from this vector, and as a result carry two C-terminal tags (FLAG™ and 6×His, respectively) for both detection and purification.

Microexpression of HuCAL GOLD® Fab Antibodies in *E. coli*

To obtain sufficient amounts of protein encoded by each of the clones obtained above, chloramphenicol-resistant single bacterial colonies are selected after subcloning of the selected Fabs into the pMORPH®X9_Fab_FH expression vector. Each of these colonies is then used to inoculate the wells of a sterile 96-well microtiter plate; with each well containing 100 µl 2×YT-CG medium per well, and bacteria are grown overnight at 37° C. A sample (5 µl) of each *E. coli* TG-1 culture is transferred to a fresh, sterile 96-well microtiter plate prefilled with 100 µl 2×YT medium supplemented with 34 µg/ml chloramphenicol and 0.1% glucose per well. The microtiter plates are incubated at 30° C. with shaking at 400 rpm on a microplate shaker until the cultures are slightly turbid (~2-4 hrs) with an $OD_{600\,nm}$ of about 0.5.

For expression in the format of these plates, 20 µl 2×YT medium supplemented with 34 µg/ml chloramphenicol and 3 mM IPTG (isopropyl-β-D-thiogalactopyranoside) is added per well (final concentration 0.5 mM IPTG), the microtiter plates sealed with a gas-permeable tape, and incubated overnight at 30° C. shaking at 400 rpm.

Generation of Whole Cell Lysates (BEL Extracts)

To each well of the expression plates, 40 µl BEL buffer (2×BBS/EDTA: 24.7 g/l boric acid, 18.7 g NaCl/l, 1.49 g EDTA/l, pH 8.0) containing 2.5 mg/ml lysozyme is added, and plates are incubated for 1 h at 22° C. on a microtiter plate shaker (400 rpm). The BEL extracts are used for binding analysis by FMAT (see Example 2).

Expression of Microgram Amounts of HuCAL GOLD® Fab Antibodies in *E. coli* and Purification Expression of Fab fragments encoded by pMORPH®X9_Fab_FH in *E. coli* TG1 F-cells is carried out in 50 ml plastic tubes. For this purpose, pre-cultures inoculated with single clones are grown in 2×YT-CG medium overnight at 30° C. The next morning, 50 µl of each pre-culture are used to inoculate 25 ml 2×YT medium supplemented with 34 µg/ml Chloramphenicol, 1 mM IPTG, and 0.1% glucose in sterile 50 ml plastic tubes, and incubated over night at 30° C. *E. coli* cells are harvested, the cell pellets frozen and finally disrupted with Bug Buster (Novagen). The Fab fragments are isolated using Ni-NTA Agarose (Qiagen, Hilden, Germany).

Expression of Milligram Amounts of HuCAL GOLD® Fab Antibodies in *E. coli* and Purification Expression of Fab fragments encoded by pMORPH®X9_Fab_FH in TG1 F-cells is carried out in shaker flask cultures using 750 ml of 2×YT medium supplemented with 34 µg/ml chloramphenicol. Cultures are shaken at 30° C. until the $OD_{600\,nm}$ reached 0.5. Expression is induced by addition of 0.75 mM IPTG followed by incubation for 20 h at 30° C. Cells are disrupted using lysozyme, and Fab fragments are isolated by Ni-NTA chromatography (Qiagen, Hilden, Germany): Protein concentrations are determined by UV-spectrophotometry (Krebs et al., 2001).

Example 2

Identification of c-Met-specific HuCAL® Antibodies

BEL extracts of individual *E. coli* clones selected by the above mentioned panning strategies are analyzed by Fluorometric Microvolume Assay Technology (FMAT™, 8200 Cellular Detection System analyzer, Applied Biosystems), to identify clones encoding c-Met-specific Fabs.

Fluorometric Microvolume Assay Technology-based Binding Analysis (FMAT) for Detection of c-Met-binding Fabs from Bacterial Lysates For the detection of c-Met-binding Fab antibodies from *E. coli* lysates (BEL extracts), binding is analyzed with the FMAT 8200 cellular detection system (Applied Biosystems). To couple His-Strep-tagged c-Met onto M-450 Expoxy beads (Dynal), a sample of 300 µl M-450 Epoxy beads ($1.2 \times 10^8$ beads) is transferred into a reaction tube and captured with a magnetic particle separator. The supernatant is removed and the beads are washed four times in 1 ml of 100 mM sodium phosphate buffer, pH 7.4. For antigen coating, 60 µg His-Strep-tagged c-Met is added to the bead suspension in 150 µl 100 mM sodium phosphate buffer, pH 7.4. The antigen-bead suspension is incubated for 16 h at room temperature on a rotating wheel. The coated beads are then washed three times with PBS and resuspended in a final volume of 250 µl. PBS.

For each 384-well plate, a mixture of 20 ml PBS containing 3% BSA, 0.005% Tween-20, 4 µl c-Met-coated beads ($1.9 \times 10^6$ beads) and 4 µl Cy5™ detection antibody is prepared. A sample of 45 µl of this solution is dispensed per well into a 384-well FMAT black/clear bottom plate (Applied Biosystems). Fab-containing BEL extract (5 µl) is added to each well. The FMAT plates are incubated at room temperature overnight. The next morning the plates are analyzed in the 8200 Cellular Detection System (Applied Biosystems).

Positive clones are obtained, and the heavy and light chain sequences of clones yielding positive, specific signals in FMAT are analyzed. Unique (non-redundant) anti-c-Met clones are identified that show sufficiently strong binding to human c-Met. These clones are expressed, purified and tested for affinity and in functional assays.

Using these clones, kinetic SPR analysis is performed on a CM5 chip (Biacore, Sweden) which had been coated with a density of ~400 RU of either recombinant human c-Met, in 10 mM Na-acetate pH 4.5 using standard EDC-NHS amine coupling chemistry. A comparable amount of human serum albumin (HSA) is immobilized on the reference flow cell. PBS (136 mM NaCl, 2.7 mM KCl, 10 mM Na2HPO4 , 1.76 mM KH2PO4 pH 7.4) is used as the running buffer. The Fab preparations are applied in concentration series of 16-500 nM at a flow rate of 20 µl/min. Association phase is set to 60 s and dissociation phase to 120 s. A summary of the affinities in nM to human c-Met is shown in Table 1 herein.

TABLE 1

Affinities of selected Fabs to human, c-Met

| Antibody | KD [nM] human c-Met BIAcore |
|---|---|
| 4536 | 1.4 |
| 4537 | 1.7 |
| 4541 | 2.6 |
| 4682 | 11.2 |
| 4687 | 0.8 |
| 4690 | 66.0 |

Example 3

Quantitative Analysis of Binding Affinities: Determination of Anti-human c-Met Fab Candidates that Bind Full Length c-Met Affinity Determination In order to further characterize the anti-c-Met antibodies, the affinity to full length human and cynomolgus c-Met is determined. GTL16, CHO cells overexpressing cynomolgus c-Met or rhesus 4 MBr-5 cells are washed, trypsinised, and suspended in PBS containing 3% FCS (3% FCS/PBS) at 4° C. 2-5×10$^5$ cells/sample are resuspended in 140 µl of 3% FCS//PBS containing 5 µg/ml of purified anti-cMet Fabs or serial dilutions thereof. As a positive control 5 µg/ml of DO24 (mouse IgG2a), anti-human c-Met is used. The cells are incubated for 30-60 minutes at 4° C. before being pelleted by centrifugation for 2 min at 2000 rpm (716 g) at 4° C. and washed in 200 µl of in chilled 3% FCS/PBS. The cells are again pelleted by centrifugation and the PBS gently removed. Cells are resuspended in 100 µl of goat anti-human IgG (H+L) PE conjugated (Jackson Cat No. 109-116-088) diluted 1:200 in 3% FCS/0.02% NaN$_3$/PBS; For the positive control goat anti-mouse IgG (H+L)-PE conjugated (Jackson Cat No. 115-116-146) diluted 1:200 in 3% FCS/PBS is used. Samples are incubated in the dark for 30-60 min at 4° C. Following centrifugation and washing in 200 µl of 3% FCS/0.02%/NaN$_3$/PBS the cells are resuspended in 100 µl of 3% FCS/PBS and assayed using FACS-array or FACS-Calibur.

The summarized affinity data on human and cynomolgus c-Met is shown in Table 2 herein. All six tested Fabs shown in Table 2 are found to have affinity to human c-Met below 100 nM. Further, nine clones produce antibodies with affinities less than 10 nM. In all tested cases, the affinities for cynomolgus and mouse c-Met are almost identical to those for human c-Met.

TABLE 2

Affinity data of selected Fabs on human, rhesus and cynomolgus c-Met

| Antibody | KD [nM] human c-Met GTL-16 | KD [nM] cyno c-Met CHO-cMet cyno | KD [nM] rhesus c-Met 4MBr-5 |
|---|---|---|---|
| 4536 | 0.4 | 0.5 | 0.1 |
| 4537 | 2.6 | ND | 0.1 |
| 4541 | 0.5 | ND | 0.1 |
| 4682 | 1.2 | 0.3 | 0.3 |
| 4687 | 5.7 | 1.1 | 1.2 |
| 4690 | 1.1 | ND | 0.1 |

Example 4

Production of HuCAL® Immunoglobulins

Conversion into the IgG Format

Antibody mediated dimerization may result in agonistic activation of the c-Met tyrosine kinase activity. Therefore Fabs, selected on the basis of binding purified c-Met, are converted in the IgG format. In order to express full length immunoglobulin (Ig), variable domain fragments of heavy ($V_H$) and light chains ($V_L$) are subcloned from the pMORPH®X9_FH Fab expression vectors either into the pMORPH®_h_Ig or the pMORPH®2_h_Ig vector series for human IgG1 and human IgG4. Restriction enzymes EcoRI, MfeI, and BlpI are used for subcloning of the $V_H$ domain fragment into pMORPH®_h_IgG1 and pMORPH®_h_IgG4. Restriction enzymes MfeI and BlpI are used for subcloning of the $V_H$ domain fragment into pMORPH®2_h_IgG1f and pMORPH®2_h_IgG4. Subcloning of the $V_L$ domain fragment into pMORPH®_h_Igκ and pMORPH®2_h_Igκ is performed using the EcoRV and BsiWI sites, whereas subcloning into pMORPH®_h_Igλ and pMORPH®2_h_Igλ2 is done using EcoRV and HpaI.

Transient Expression and Purification of Human IgG

HEK293 cells are transfected with an equimolar amount of IgG heavy and light chain expression vectors. On days 4 or 5 after transfection, the cell culture supernatant is harvested. After adjusting the pH of the supernatant to 8.0 and sterile filtration, the solution is subjected to standard protein A column chromatography (Poros 20A, PE Biosystems).

Conversion of Parental Fabs into the IgG1 and IgG4 Formats

In parallel to the start of the affinity maturation, inserts are cloned into the pMORPH®_h_IgG1 and pMORPH®_h_IgG4 expression vectors. Small scale expression is performed by transient transfixion of HEK293 cells and the full length immunoglobulins are purified from the cell culture supernatant.

Identification of Anti-human c-Met IgG Candidates Modulating c-Met Dependent Proliferation The resulting different c-Met-specific antibodies selected from the HuCAL GOLD® library are then converted into IgG format and tested for potency to inhibit HGF driven proliferation.

The functional activity of each of the selected clones is assessed using a BrdU incorporation assay upon HGF stimulation of 4 MBr-5 cells. 4 MBr-5 cells are plated at a density of 3×10$^3$ cells per well, in a total volume of 100 µl/well Ham's F12K supplemented with 10% FBS in 96-well flat-bottom tissue culture treated plates (Costar, #3610). The plates are incubated at 37° C. in a 5% $CO_2$ atmosphere for 2 hrs, after which 50 µl of medium containing the purified antibody to be tested is added. As a negative control for lack of modulation, a sample of an unrelated antibody (having a known specificity unrelated to c-Met epitope determinants), or buffer, is added to designated wells. The plates are incubated at 37° C. in a 5% $CO_2$ atmosphere for 1 hr, after which, 50 µl of the medium alone or 50 µl containing HGF (e.g., about 0.5 µg/µl to about 50 ng/ml) is added. The plates are incubated at 37° C. in a 5% $CO_2$ atmosphere for 72 hrs, after which BrDU incorporation is assayed using the cell proliferation ELISA, BrdU-Assay (Roche) Cat No. 1 669 915. Briefly, 20 µM/well of BrdU solution (#1) is added and the plates incubated for 22 hrs at 37° C. in a 5% $CO_2$ atmosphere. Medium is gently removed and the plate dried for 1 hr at 60° C. 200 µl of FixDenat (solution #2) is added and the plates incubated at room temperature with gentle shaking for 30 minutes. The solution is gently removed and 100 µl/well anti-BrDU working solution added. The plates are incubated at room temperature with gentle shaking for 90 minutes. The solution is gently removed and the wells washed three times with 250 µl of washing solution. The solution is gently removed and 100 µl/well substrate solution added plates are measured at A405 nm.

$EC_{50}$ determination

The data showing the effective concentration for 50% inhibition of HGF stimulated proliferation for the clones of antibodies having the greatest affinity for c-Met is shown in Table 3 herein. The data show that effective concentrations $EC_{50}$ range from 4 nM, with a median value between 6 and 150 nM.

Identification of Anti-human c-Met IgG Candidates Modulating c-Met Dependent Migration Cellular migration in response to stimulation with HGF is assayed using NCI-H441 cells in the QCM™ chemotaxis 8 µM 96-well cell migration assay. As described above, 24 hrs prior to the assay cells are washed twice with sterile PBS and starved in the DMEM containing 1% FBS at 37° C. in a 5% $CO_2$ atmosphere. Subsequently, the cells are trypsinised and resuspended at 1.0×10$^6$ cells per mL in the presence of appropriate concentration of the purified antibody for 30 min at 37° C. As a negative control for lack of modulation, a sample of an unrelated antibody (having a known specificity unrelated to c-Met epitope determinants), or buffer, is added to designated wells.

Under sterile conditions the lid of the migration chamber plate is removed and 150 μL of serum free media containing 50 ng/ml HGF (R&D Cat No. 294-HGN) is added to the wells of the feeder tray (lower chamber). 100 μL of 5-10×10$^4$ cells in DMEM with 1% FBS preincubated with antibody is gently added to the top chamber. The plate is covered and incubated for 16 hours at 37° C. in 4-6% $CO_2$. Following the manufacturers instructions, the cells/media in the top chamber is discarded and the chamber placed into a 96-well Feeder Tray into which 150 μL/well prewarmed cell detachment solution has been added. Cells are dislodged by incubating for 30 minutes at 37° C. with periodic gentle agitation. Subsequently, 50 μl of prediluted CyQuant GR Dye is added to each well of the feeder tray. The plate is incubated for 15 minutes at room temperature and 150 μL of the mixture transferred to a new 96-well plate suitable for fluorescence measurement using a 480/520 nm filter set The data showing the effective concentration for 50% inhibition of HGF stimulated migration for the clones of antibodies having the greatest affinity for c-Met is shown in Table 3 herein. The data show that effective concentrations $EC_{50}$ range from 0.14 nM, with a median value between 0.27 and 0.61 nM.

TABLE 3

Effective concentration for 50% inhibition of selected Fabs

| Fab | EC50 [nM] Inhibition of HGF driven proliferation 4MBr-5 | EC50 [nM] Inhibition of HGF driven migration NCI-H441 |
|---|---|---|
| 4536 | 4 | 0.61 |
| 4537 | 150 | 0.14 |
| 4541 | 200 | 0.27 |
| 4687 | 6 | 1.68 |

Example 5

Affinity Maturation of Selected Anti-c-Met Fabs by Parallel Exchange of LCDR3 and HCDR2 Cassettes For optimizing the affinities of the antibodies described herein for c-Met for a pool of parental Fab fragments, the LCDR3, framework 4 and the constant region of the light chains (405 bp) of each parental Fab is removed using BpiI and SphI, and is replaced by a repertoire of diversified LCDR3s together with framework 4 and the constant domain. A sample of 0.5 μg of the binder pool vector is ligated with a 3-fold molar excess of the insert fragment carrying the diversified LCDR3s.

In a similar approach, the HCDR2 is diversified using the XhoI and BssHII sites, and the connecting framework regions are kept constant. In order to increase the cloning efficiency, the parental HCDR2 is replaced by a 590 bp stuffer sequence prior to the insertion of the diversified HCDR2 cassette.

Ligation mixtures of different libraries are electroporated into 4 ml E. coli TOP10 F' cells (Invitrogen, Carlsbad, Calif., USA), yielding from 2×10$^7$ to 2×10$^8$ independent colonies. Amplification of the libraries is performed as previously described (Rauchenberger et al., 2003 J Biol Chem. 278(40): 38194-38205). For quality control, several clones per library are randomly picked and sequenced (SequiServe, Vaterstetten, Germany) using primers CFR84 (VL) and OCAL_Seq_Hp (VH).

Selection of Candidates for Affinity Maturation

Six selected maturation candidates ("parental Fabs") are selected using the following properties: affinities to human c-Met less than 10 nM, with significant cross-reactivity to cynomolgus c-Met, $EC_{50}$ less than 250 nM, and good to moderate Fab expression levels in E. coli and activity in the IgG format in c-Met driven proliferation and migration assays. The properties of selected Fab fragments are provided in Table 4.

TABLE 4

Properties of selected Fabs

| Antibody | KD [nM] human c-Met BIAcore | KD [nM] human c-Met GTL-16 | KD [nM] cyno c-Met CHO-cyno c-Met | Fab expression [mg/l] | EC50 [nM] 4Mbr-5 Proliferation IgG | EC50 [nM] NCI-H441 Migration IgG |
|---|---|---|---|---|---|---|
| 4536 | 1.4 | 1.7 | 229.1 | 6.3 | 4 | 0.61 |
| 4537 | 1.7 | 1.5 | 12.7 | 7.4 | 150 | 0.14 |
| 4541 | 2.6 | 1.7 | 0.6 | 5.3 | 200 | 0.27 |
| 4687 | 0.8 | 4.0 | 1.3 | 1.4 | 6 | 1.68 |

Generation of Selected Fab Libraries for Affinity Maturation

In order to obtain clones having increased affinity and inhibitory activity of the anti-c-Met antibodies, the selected Fab clones shown in the previous example are subjected to further rounds of diversification and selection, a process known as affinity maturation: For this purpose; CDR regions are diversified using corresponding LCDR3 and HCDR2 maturation cassettes pre-built by trinucleotide mutagenesis Virnekäs et al., 1994 Nucleic Acids Res. 22:5600-5607; Nagy et al., 2002 Nature Medicine 8:801-807).

Fab fragments from expression vector pMORPH®X9_Fab_FH are subcloned into the phagemid vector pMORPH®25 (see U.S. Pat. No. 6,753,136). This vector provides the phage protein pIII fused N-terminally to a cysteine residue as well as a C-terminal cysteine to the Pd antibody chain and thus allows disulfide-linked display of the respective Fab fragments on the phage surface. Two different strategies are applied in parallel to optimize both the affinity and the efficacy of the parental Fabs.

Five phage antibody Fab libraries are generated in which the LCDR3 of five of the six parental clones is replaced by a repertoire of individual light chain CDR3 sequences. (The LCDR3 maturation of one clone is not performed, as this clone has an additional BpiI restriction site in one of the CDR regions and the BpiI restriction enzyme is used for the library-cloning procedure.)

In parallel, the HCDR2 region of each parental clone is replaced by a repertoire of individual heavy chain CDR2 sequences. Each parental Fab is excised and replaced for a 590 bp stuffer. This DNA stuffer facilitates the separation of single digested from double digested vector bands and reduces the background of the high-affinity parental Fabs during the maturation pannings. In a subsequent step, the stuffer is excised from the Fab-encoding plasmids of each parental clone and replaced for the highly diversified HCDR2 maturation cassette Large affinity maturation libraries of more than $2\times10^7$ members are generated by standard cloning procedures, and the diversified clones are transformed into electro-competent E. coli TOP10F' cells (Invitrogen). Fab-presenting phages are prepared as described above.

Maturation pools are built in order to facilitate the subsequent selection process: pool 1a consisted of the LCDR3-1 libraries; pool 1b consisted of the HCDR2-1 libraries; pool 2a consisted of the LCDR3-2 libraries; and pool 2b consisted of the HCDR2-2 libraries.

For each pool the panning is performed in solution using decreasing amounts of His-Strep-tagged c-Met and phage-antigen capturing by Strep-Tactin beads. In parallel, each pool is applied in pannings using decreasing amounts of biotinylated c-Met, which is captured onto Neutravidin-coated plates. In order to increase the panning stringency and to select for improved off rates, competition with purified parental Fabs as well as unlabeled antigen is performed during prolonged incubation periods.

Immediately after panning the enriched phagemid pools are subcloned into the pMORPH®X9_FH expression vector. Single clones are picked, and expression of genes in the Fabs is induced with IPTG.

Maturation Panning Strategies

Panning procedures using the four antibody pools are performed with His-Strep-tagged c-Met and with biotinylated His-Strep-tagged c-Met in solution for two or three rounds, respectively. For each of the panning strategies, competition with the purified parental Fab proteins or with unlabeled APP-tagged c-Met, as well as low antigen concentrations and extensive washing, are used to increase stringency.

The solution panning on unlabeled His-Strep-tagged c-Met is performed over two selection rounds mainly according to the standard protocol described in Example 1. Exceptions to these procedures are the application of reduced amounts of antigen (decreasing from 5 nM down to 1 nM), the high stringency of the washing procedure either with competitor or without, and prolonged incubation periods of antibody-phages together with the antigen.

For the first selection round using biotinylated c-Met, the wells of a Neutravidin plate are washed two times with 300 µl PBS. The wells are blocked with 2× ChemiBLOCKER (Chemicon, Temecula, Calif.) diluted 1:1 in PBS (Blocking Buffer). Prior to the selections, the HuCAL GOLD® phages are also blocked with one volume Blocking Buffer containing 0.1% Tween-20 for 30 min at room temperature. The blocked phage preparations are transferred in 100 µl aliquots to the wells of a Neutravidin-coated plate for 30 min at room temperature. This pre-adsorption step is repeated once. Blocked and pre-cleared phage preparations are incubated with 5 nM biotinylated c-Met for 2 h at 22° C. on a rotating wheel. A sample containing parental Fab and APP-c-Met, or a positive control containing no competitor, is added and the samples are incubated overnight at 4° C. on a rotating wheel.

Antigen-phage complexes are captured in the wells of a Neutravidin plate for 20 min at room temperature. After extensive washing steps, bound phage particles are eluted by addition of 200 µl of 20 mM DTT in 10 mM Tris pH 8.0 per well for 10 min at room temperature. The eluate is removed and added to 14 ml E. coli TG1 cells grown to an $OD_{600\,nm}$ of 0.6-0.8. The wells are rinsed once with 200 µl PBS and this solution is also added to the E. coli TG1 cells. Phage infection of E. coli is allowed for 45 min at 37° C. without shaking. After centrifugation for 10 min at 5000 rpm, the bacterial pellets are each resuspended in 500 µl 2×YT medium, plated onto 2×YT-CG agar plates and incubated overnight at 30° C.

The colonies are harvested by scraping from the surface of the plates and the phage particles are rescued and amplified as described above.

The second and third round of the selection are performed as described above for the first round of selection, excepted that washing conditions are more stringent and antigen concentrations are 1 and 0.1 nM, respectively.

Electrochemiluminescence (BioVeris)-based Binding Analysis of c-Met Binding Fabs For the detection of affinity-improved, c-Met-specific antibody fragments in E. coli lysates (BEL extracts), a BioVeris M-384 SERIES® Workstation (BioVeris Europe, Witney, Oxfordshire, UK), is used. The assay is carried out in 96-well polypropylene microtiter plates and PBS supplemented with 0.5% BSA and 0.02% Tween-20 as the assay buffer. Biotinylated human c-Met is immobilized on M-280 Streptavidin paramagnetic beads (Dynal) according to the instructions of the supplier. A 1:25 dilution of the bead stock solution is added per well. Samples of 100 µl diluted BEL extract and beads are incubated overnight at room temperature on a shaker. For detection, anti-human (Fab)'2 (Dianova) labelled with BV-TAG™ label according to instructions of the supplier (BioVeris Europe, Witney, Oxfordshire, UK) is used.

A set of randomly picked clones is analyzed by the method described above. A subset of those clones giving the highest values is chosen for further analysis in solution equilibrium titration.

Determination of Picomolar Affinities Using Solution Equilibrium Titration (SET)

For $K_D$ determination, monomer fractions (at least 90% monomer content, analyzed by analytical SEC; Superdex75, Amersham Pharmacia) of Fab are used. Electrochemiluminescence (ECL) based affinity determination in solution and data evaluation are basically performed as described by Haenel et al., 2005. A constant amount of Fab is equilibrated with different concentrations (serial $3^n$ dilutions) of human c-Met (4 nM starting concentration) in solution. Biotinylated human c-Met coupled to paramagnetic beads (M-280 Streptavidin, Dynal), and BV-tag™ (BioVeris Europe, Witney, Oxfordshire, UK) labelled anti-human (Fab)'$_2$ (Dianova) is added and the mixture incubated for 30 min. Subsequently, the concentration of unbound Fab is quantified by ECL detection using the M-SERIES® 384 analyzer (BioVeris Europe).

For this purpose, single clones are selected and purified by Ni-NTA Agarose in the µg scale. Preliminary affinities are determined by 4-point solution equilibrium titration (SET) in BioVeris. From these data, clones showing affinities are selected. These Fabs are purified in the mg scale. Final affinities are determined from two independent batches of each Fab clone using ah 8-point SET measurement and human, mouse, and cynomolgus c-Met.

Affinity determination to mouse and cynomolgus c-Met is done essentially as described above using mouse c-Met (R&D Systems) and cynomolgus c-Met as analyte in solution instead of human c-Met. For detection of free Fab, biotinylated human c-Met coupled to paramagnetic beads is used. Affinities are calculated according to methods known to those skilled in the art, e.g., Haenel et al., 2005 Anal Biochem 339.1:182-184.

Using the assay conditions described above, the affinities for the affinity-optimized anti-c-Met Fabs are determined in solution. Affinities are determined for antibodies with $K_D$s below 4.6 pM to human c-Met. FACs based analysis of binding to cyno-c-Met expressed on CHO cells, as described above, is carried out. The affinities are summarized in Table 5 herein.

TABLE 5

Affinities of Fabs

| Antibody | Affinity [pM]: solution equilibrium titration Human c-Met | KD [pM] cyno c-Met CHO-cyno c-Met Cyno c-Met |
|---|---|---|
| 5091 | 2.4 ± 0.5 | 90 |
| 5097 | 3.6 ± 0.9 | 0.68 |
| 5098 | 2.1 ± 0.5 | 0.3 ± 0.1 |
| 5185 | 4.6 ± 3.9 | 0.29 |

Example 6

Characterization of Affinity-optimized Anti-human c-Met Fabs

FACS Saturation Techniques

Binding specificity of the matured Fabs in the presence of 50% human serum (HS) is determined. Serial dilutions of optimized anti-cMet Fabs are incubated in the presence of either 50% human serum or in the presence of 2.8% BSA. FACS saturation binding to GTL-16 cells is assessed. GTL16 cells are washed, trypsinised, and suspended in PBS containing 3% FCS (3% FCS/PBS) at 4° C. $2\text{-}5 \times 10^5$ cells/sample are resuspended in 140 µl of 3% FCS//PBS containing 5 µg/ml of purified optimized anti-cMet Fabs or serial dilutions thereof. As a positive control 5 µg/ml of DO24 (mouse IgG2a), anti-human c-Met is used. The cells are incubated for 30-60 minutes at 4° C. before being pelleted by centrifugation for 2 min at 2000 rpm (716 g) at 4° C. and washed in 200 µl of chilled 3% FCS/PBS. The cells are again pelleted by centrifugation and the PBS gently removed. Cells are resuspended in 100 µl of goat anti-human IgG (H+L) PE conjugated (Jackson Cat No. 109-116-088) diluted 1:200 in 3% FCS/PBS; For the positive control goat anti-mouse IgG (H+L)-PE conjugated (Jackson Cat No. 115-116-146) diluted 1:200 in 3% FCS/PBS is used. Samples are incubated in the dark for 30-60 min at 4° C. Following centrifugation and washing in 200 µl of 3% FCS/PBS the cells are resuspended in 100 µl of 3% FCS/PBS and assayed using FACS-array or FACS-Calibur Exemplary binding curves are shown in Table 6, which summarizes the binding activity of the optimized anti-c-Met Fabs in presence of 50% human serum compared to binding activity in 2.8% BSA, which ranges from 83.3% to 100%. The median value is found to be 90.2%, thus the anti-c-Met Fabs are found to fully bind to target in the presence of human serum.

TABLE 6

Binding activity of Fabs

| Antibody | Binding activity w/ 50% Human serum vs 2.8% BSA (%) |
|---|---|
| 5091 | 83.8 |
| 5097 | 90.2 |
| 5098 | 100 |
| 5185 | * |

* Binding of 5185 not analyzed yet in terms of EC50 since saturation is not reached Conversion of Optimized Anti-cMet Candidate Fabs into the IgG Format Antibody mediated dimerization may result in agonistic activation of the c-Met tyrosine kinase activity. Therefore optimized Fabs, selected on the basis of binding purified c-Met, are converted in the IgG format. In order to express full length immunoglobulin (Ig), variable domain fragments of heavy ($V_H$) and light chains ($V_L$) are subcloned from the pMORPH®X9_FH Fab expression vectors either into the pMORPH®_h_Ig or the pMORPH®2_h_Ig vector series for human IgG1 and human IgG4. Restriction enzymes EcoRI, MfeI, and BlpI are used for subcloning of the $V_H$ domain fragment into pMORPH®_h_IgG1 and pMORPH®_h_IgG4. Restriction enzymes MfeI and BlpI are used for subcloning of the $V_H$ domain fragment into pMORPH®2_h_IgG1f and pMORPH®2_h_IgG4. Subcloning of the $V_L$ domain fragment into pMORPH®_h_Igκ and pMORPH®2_h—Igκ is performed using the EcoRV and BsiWI sites, whereas subcloning into pMORPH®_h_Igλ and pMORPH®2_h_Igλ2 is done using EcoRV and HpaI.

Transient Expression and Purification of Human IgG

HEK293 cells are transfected with an equimolar amount of IgG heavy and light chain expression vectors. On days 4 or 5 after transfection, the cell culture supernatant is harvested. After adjusting the pH of the supernatant to 8.0 and sterile filtration, the solution is subjected to standard protein A column chromatography (Poros 20A, PE Biosystems).

Identification of Optimized Anti-human c-Met IgG Candidates Modulating c-Met Dependent Proliferation The resulting optimized c-Met-specific antibodies selected from the HuCAL GOLD® library are then converted into IgG format and tested for potency to inhibit HGF driven proliferation.

The functional activity of each of the selected clones is assessed using a BrdU incorporation assay upon HGF stimulation of 4 MBr-5 cells. 4 MBr-5 cells are plated at a density of $3 \times 10^3$ cells per well in a total volume of 100 µl/well Ham's F12K supplemented with 10% FBS in 96-well flat-bottom tissue culture treated plates (Costar, #3610). The plates are incubated at 37° C. in a 5% $CO_2$ atmosphere for 2 hrs, after which 50 µl of medium containing the purified antibody to be tested is added. As a negative control for lack of modulation, a sample of an unrelated antibody (having a known specificity unrelated to c-Met epitope determinants), or buffer, is added to designated wells. The plates are incubated at 37° C. in a 5% $CO_2$ atmosphere for 1 hr, after which, 50 µl of the medium alone or 50 µl containing HGF (e.g., about 0.5 µg/µl to about 50 ng/ml) is added. The plates are incubated at 37° C. in a 5% $CO_2$ atmosphere for 72 hrs, after which BrDU incorporation is assayed using the cell proliferation ELISA, BrdU-Assay (Roche) Cat No. 1 669 915. Briefly, 20 µM/well of BrdU solution (#1) is added and the plates incubated for 22 hrs at 37° C. in a 5% $CO_2$ atmosphere. Medium is gently removed and the plate dried for 1 hr at 60° C. 200 µl of FixDenat (solution #2) is added and the plates incubated at room temperature with gentle shaking for 30 minutes. The solution is gently removed and 100 µl/well anti-BrDU working solution added. The plates are incubated at room temperature with gentle shaking for 90 minutes. The solution is gently removed and the wells washed three times with 250 µl of washing solution. The solution is gently removed and 100 µl/well substrate solution added plates are measured at A405 nm.
EC$_{50}$ determination The data showing the effective concentration for 50% inhibition of HGF stimulated proliferation for the clones of antibodies having the greatest affinity for c-Met is shown in Table 7 herein. The data show that effective concentrations EC$_{50}$ range from 0.13 nM, with a median value between 0.5 nM and 1.3 nM.

TABLE 7

Inhibitory activity of optimized anti-c-Met candidates in IgG formation on HGF stimulated proliferation

| Antibody | EC50 [nM] Inhibition of HGF driven proliferation 4MBr-5 in 10% serum |
|---|---|
| 5091 | 1.3 |
| 5097 | 1.6 |
| 5098 | 0.5 |
| 5185 | 0.13 |

Enzyme Linked Immuno Sorbent Assay (ELISA) Techniques

Binding specificity of the matured F$_{ab}$s in the presence of 50% human serum (HS) is determined. Serial dilutions of human recombinant, biotinylated antibody in TBS are coated onto. Neutravidin microtiter plates for 2 h at room temperature, from 8 ng antibody per well to a concentration of 125 ng antibody per well. After coating of the antigen, wells are blocked with TBS/0.05% Tween (TBS-T) supplemented with 1% BSA for 1 h at room temperature. Purified Fabs described above are diluted either in TBS/4% BSA or TBS/50% HS at a final concentration of 1 µg/ml, added to the coated and blocked wells and the plates are incubated for 1 h at room temperature. For detection, an anti-FLAG alkaline phosphatase (AP)-conjugated antibody (1:5000 dilution in TBST) and the fluorogenic substrate AttoPhos (Roche) are used. After each incubation, the wells of the microtiter plates are washed with TBST five times, except after the final incubation step with the labeled secondary antibody when wells are washed three times. The fluorescence is measured in a TECAN Spectrafluor plate reader.

Identification of Anti-human c-Met IgG Candidates Modulating c-Met Dependent Migration Cellular migration in response to stimulation with HGF is assayed using NCI-H441 cells in the QCM™ chemotaxis 8 µM 96-well cell migration assay. As described above, 24 hrs prior to the assay cells are washed twice with sterile PBS and starved in the DMEM containing 1% FBS at 37° C. in a 5% CO$_2$ atmosphere. Subsequently, the cells are trypsinised and resuspended at 1.0×10$^6$ cells per mL in the presence of appropriate concentration of the purified antibody for 30 min at 37° C. As a negative control for lack of modulation, a sample of an unrelated antibody (having a known specificity unrelated to c-Met epitope determinants), or buffer, is added to designated wells.

Under sterile conditions the lid of the migration chamber plate is removed and 150 µL of serum free media containing 50 ng/ml HGF (R&D Cat No. 294-HGN) is added to the wells of the feeder tray (lower chamber). 100 µL of 5-10×10$^4$ cells in DMEM with 1% FBS preincubated with antibody is gently added to the top chamber. The plate is covered and incubated for 16 hours at 37° C. in 4-6% CO$_2$. Following the manufacturers instructions, the cells/media in the top chamber is discarded and the chamber placed into a 96-well Feeder Tray into which 150 µL/well prewarmed cell detachment solution has been added. Cells are dislodged by incubating for 30 minutes at 37° C. with periodic gentle agitation. Subsequently, 50 µl of prediluted CyQuant GR Dye is added to each well of the feeder tray. The plate is incubated for 15 minutes at room temperature and 150 µL of the mixture transferred to a new 96-well plate suitable for fluorescence measurement using a 480/520 nm filter set The data showing the effective concentration for 50% inhibition of HGF stimulated migration for the clones of antibodies having the greatest affinity for c-Met is shown in Table 8 herein. The data show that effective concentrations EC$_{50}$ range from 0.61 nM, with a median value between 0.73 nM and 0.76 nM.

TABLE 8

Inhibitory activity of optimized anti-c-Met candidates in IgG formation on HGF stimulated migration

| Antibody | EC50 [nM] Inhibition of HGF driven migration NCI-H441 in 1% serum |
|---|---|
| 5091 | 0.61 ± 0.22 |
| 5097 | 0.76 ± 0.69 |
| 5098 | 0.73 ± 1.1 |
| 5185 | 1.2 ± 1.3 |

Example 7

Modulation of HGF Stimulated c-Met Autophosphorylation by Selected Antagonistic Anti-c-Met Antibodies Agonism or antagonism by anti-c-Met antibodies of the invention is measured by activation or inhibition of c-Met phosphorylation in cells with and without stimulation with HGF. Cells of a cell line such as A549 cells are plated at a density of 3×10$^4$ cells per well in a total volume of 100 µl/well DMEM supplemented with 10% FBS in 96-well flat-bottom tissue culture treated plates (Costar, #3595). The plates are incubated at 37° C. in a 5% CO$_2$ atmosphere for 24 hrs, after which the medium is gently aspirated from each well of the plates and a volume of 100 µl/well DMEM added. The plates are incubated at 37° C. in a 5% CO$_2$ atmosphere for 24 hrs, after which a sample of a purified antibody to be tested, 100 µl per well of the antibody or a dilution, is added to cells in the well diluted in DMEM. As a negative control for lack of activation, a sample of an unrelated antibody (having a known specificity unrelated to c-Met epitope determinants), or buffer, is added to designated wells.

The cells are incubated at 37° C. for a short time period (e.g., 2 hours) or a longer time period (e.g., 24 hours). Where appropriate, cells are stimulated by the addition of HGF in serum-free DMEM media at a final concentration of 200 ng/well. In general, when assaying the agonistic activity of the antibodies, except for the positive control (not treated with antibody), HGF is omitted from the test sample antibody wells. In general, when assaying the antagonistic activity of the antibodies, HGF is included in the test sample antibody wells. Plates are further incubated for 10 min at 37° C., then the medium is gently aspirated from the wells of the plates. The cells are washed with cold PBS containing and the solution is gently aspirated from the plates. The cells are lysed with 50 µl lysis buffer (NP-40 Lysis buffer: 120 mM NaCl, 50 mM Tris-HCl pH 7.5, 1% NP-40, 1 mM EDTA, 6 mM EGTA, 20 mM NaF, 1 mM Benzamidine with freshly added 0.5 mM Na$_3$VO$_4$, and 0.1 mM PMSF). The plates are shaken at room temperature for 15 minutes, and are then stored at −80° C. until needed for ELISA.

An ELISA is used to determine c-Met phosphorylation levels. For ELISA plate preparation, Nunc-Immuno™ Plate, MaxiSorb™ Surface (VWR International AG, No. 391-8786) are washed twice with wash buffer (PBS-0.05% Tween Biorad #670-6531), and 100 μl of c-Met monoclonal capture antibody (DO-24) in PBS is added. The plates are incubated overnight at 4° C. washed three times with PBS-0.05% Tween. Non-specific binding sites are blocked with 200 μl/well 3% BSA in PBS-T for 2 hours at room temperature, with shaking. Immediately before use blocking solution is removed.

Frozen cell lysates are melted by shaking at room temperature and 40 μl of lysate is added to the Nunc-Immuno plates and the plates are incubated at 4° C. for 4 hours. The plates are washed three times with PBS-T, and 50 μl/well of 0.2 μg/ml anti-phosphotyrosine antibody PY20-HRP (ZYMED, # 03-7722) in 3% bovine serum albumin-PBS-T. The plates are incubated overnight over night at 4° C. and washed three times with PBS-T. The PBS-T is aspirated and 90 μl/well alkaline phosphatase substrate (CDR-Star, TROPIX, #MS100RY) added and developed while gently shaking for 45 min at room temperature. The plates are read using a 96-well plate reader.

The data showing the effective concentration for 50% inhibition of HGF stimulated migration for the clones of antibodies having the greatest affinity for c-Met is shown in Table 9 herein. The data show that effective concentrations EC$_{50}$ range from 0.166 nM, with a median value between 0.193 and 0.219 nM.

TABLE 9

Inhibitory activity of optimized anti-c-Met candidates in IgG formation on HGF stimulated receptor autophosphorylation

| Antibody | EC50 [nM] Inhibition of HGF stimulated c-Met autophosphorylation in A549 |
| --- | --- |
| 5091 | 0.193 |
| 5097 | 0.166 |
| 5098 | 0.419 |
| 5185 | 0.219 |

Example 8

Amino Acid Sequences and Nucleotide Sequences of Genes Optimized for Expression

To increase mammalian expression, changes are introduced into the heavy and the light chains of Fabs herein for optimization of codon usage for expression in a mammalian cell. It is known that several negatively cis-acting motifs decrease expression in mammals. The optimization process herein removes negative cis-acting sites (such as splice sites or poly(A) signals) which negatively influence expression. The optimization process herein further enriches GC content, to prolong mRNA half-life.

Variable light and heavy chain regions are optimized using a clone of a Fab and isolated by selection with phage display. Then the nucleotide sequences encoding each of the entire light and heavy chains of this and other clones are each optimized using these procedures.

Optimization Process for V$_H$ and V$_L$ Chains

For optimizing the nucleotide sequence and amino acid sequence of each of the V$_L$ and V$_H$ chains, the codon usage is adapted to the codon bias of mammalian, especially *H. sapiens*, genes. In addition, regions of very high (>80%) or very low (<30%) GC content are reduced or eliminated where possible.

During the optimization process, the following cis-acting sequence motifs are avoided: internal TATA-boxes, chi-sites and ribosomal entry sites, AT-rich or GC-rich sequence stretches, RNA instability motif (ARE) sequence elements, inhibitory RNA sequence elements (INS), cAMP responsive (CRS) sequence elements, repeat sequences and RNA secondary structures, splice donor and acceptor sites including cryptic sites, and branch points. Except as indicated, introduction of MluI and HindIII sites is avoided in the process of optimizing the nucleotide sequence of the V$_L$ chain. Except as indicated, introduction of MlyI and BstEII sites is avoided in the process of optimizing the nucleotide sequence of the V$_H$ chain.

Amino Acid Sequences of V$_H$ and V$_L$ Chains Optimized for Expression

Codon usage is adapted to that of Mammals to enable higher and more stable expression rates in a mammalian cell for the resulting optimized amino acid sequences for the V$_H$ and V$_L$ chains of the clone described above.

Histograms may be used to show the percentages of sequence codons for each of the parental sequences and optimized genes respectively, and analyses the quality class of the respecting nucleotide sequences encoding the V$_H$ and V$_L$ chains. Quality value as used herein means that the most frequent codon used for a given amino acid in the desired expression system is set as 100, and the remaining codons are scaled accordingly to frequency of usage. (Sharp, P. M., Li, W. H., *Nucleic Acids Res.* 15 (3), 1987).

Further, the codon adaptation index (CAI) is a number that describes how well the codons of the nucleotide sequence match the codon usage preference of the target organism. The maximum value of CAI is set to 1.0, thus a CAI of >0.9 is considered as enabling high expression. The CAI for the V$_L$ chain prior to optimization is found to be 0.73, and after optimization, the CAI is determined to be 0.95. Similarly, the CAI for the V$_H$ chain prior to optimization is found to be 0.74, and after optimization, is determined to be 0.98.

The GC content in the V$_L$ chain is increased from the parent sequence for the optimized sequence.

Optimization for Expression of Full Length Light Chains and Heavy Chains

The optimization process is applied to each of the parent full length nucleotide sequences of the light chains and the parent full length nucleotide sequences of the heavy chains.

The optimization process is used to construct the light chain nucleotide sequences associated with the parent clone numbers. Further, the optimization process is used to construct the heavy chain nucleotide sequences associated with the parent clone numbers.

TABLE E

LISTING OF SEQUENCES OF THE INVENTION

| Ab Ref. No. - Chain Type | SEQ ID NO. | SEQUENCE |
|---|---|---|
| 04536 VL | 1 | GATATCGAACTGACCCAGCCGCCTTCAGTGAGCGTTGCACCAGGTCAGAC<br>CGCGCGTATCTCGTGTAGCGGCGATTCTATTGGTAATAAGTATGTTCATT<br>GGTACCAGCAGAAACCCGGGCAGGCGCCAGTTCTTGTGATTTATGCTGAT<br>TCTGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGGCTTATGATTCTTCTATGCTTCGTGTGTTTGGCGGC<br>GGCACGAAGTTAACCGTTCTTGGCCAG |
| 05087 VL | 2 | GATATCGAACTGACCCAGCCGCCTTCAGTGAGCGTTGCACCAGGTCAGAC<br>CGCGCGTATCTCGTGTAGCGGCGATTCTATTGGTAATAAGTATGTTCATT<br>GGTACCAGCAGAAACCCGGGCAGGCGCCAGTTCTTGTGATTTATGCTGAT<br>TCTGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGTCTTATGCTAATTATCATGATTCTTCGGTGTTTGGC<br>GGCGGCACGAAGTTAACCGTTCTTGGCCAG |
| 05088 VL | 3 | GATATCGAACTGACCCAGCCGCCTTCAGTGAGCGTTGCACCAGGTCAGAC<br>CGCGCGTATCTCGTGTAGCGGCGATTCTATTGGTAATAAGTATGTTCATT<br>GGTACCAGCAGAAACCCGGGCAGGCGCCAGTTCTTGTGATTTATGCTGAT<br>TCTGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGTCTTATGCTTCTGATTATACTTCTTGGGTGTTTGGC<br>GGCGGCACGAAGTTAACCGTTCTTGGCCAG |
| 05091 VL | 4 | GATATCGAACTGACCCAGCCGCCTTCAGTGAGCGTTGCACCAGGTCAGAC<br>CGCGCGTATCTCGTGTAGCGGCGATTCTATTGGTAATAAGTATGTTCATT<br>GGTACCAGCAGAAACCCGGGCAGGCGCCAGTTCTTGTGATTTATGCTGAT<br>TCTGATCGTCCCTCAGGCATCCCGGAACGCTTTAGCGGATCCAACAGCGG<br>CAACACCGCGACCCTGACCATTAGdGGCACTCAGGCGGAAGACGAAGCGG<br>ATTATTATTGCCAGTCTTATGCTCATTATCATGATATTTGGGTGTTTGGC<br>GGCGGCACGAAGTTAACCGTTCTTGGCCAG |
| 05092 VL | 5 | GATATCGAACTGACCCAGCCGCCTTCAGTGAGCGTTGCACCAGGTCAGAC<br>CGCGCGTATCTCGTGTAGCGGCGATTCTATTGGTAATATGTATGTTCATT<br>GGTACCAGCAGAAACCCGGGCAGGCGCCAGTTCTTGTGATTTATGCTGAT<br>TCTGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGGCTCATGATTCTCTTTATTCTCGTGTGTTTGGCGGC<br>GGCACGAAGTTAACCGTTCTTGGCCAG |
| 04687 VL | 6 | GATATCGTGATGACCCAGAGCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAATTTATTGGGCTTCTACTCGTGAAAGCGGGGTCCCGGATCGTTT<br>TAGCGGCTCTGGATCCGGCACTGATTTTACCCTGACCATTTCGTCCCTGC<br>AAGCTGAAGACGTGGCGGTGTATTATTGCCAGCAGTATTATAATCATCCT<br>CATACCTTTGGCCAGGGTACGAAGTTGAAATTAAACGTACG |
| 05097 VL | 7 | GATATCGTGATGACCCAGAGCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAATTTATTGGGCTTCTACTCGTGAAAGCGGGGTCCCGGATCGTTT<br>TAGCGGCTCTGGATCCGGCACTGATTTTACCCTGACCATTTCGTCCCTGC<br>AAGCTGAAGACGTGGCGGTGTATTATTGCCAGCAGTATGCTTTTGGTTGG<br>ACCTTTGGCCAGGGTACGAAAGTTGAAATTAAACGTACG |
| 05098 VL | .8 | GATATCGTGATGACCCAGAGCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAATTTATTGGGCTTCTACTCGTGAAAGCGGGGTCCCGGATCGTTT<br>TAGCGGCTCTGGATCCGGCACTGATTTTACCCTGACCATTTCGTCCCTGC<br>AAGCTGAAGACGTGGCGGTGTATTATTGCCTTCAGTATTCTGATGAGCCT<br>TGGACCTTTGGCCAGGGTACGAAAGTTGAAATTAAACGTACG |
| 05100 VL | 9 | GATATCGTGATGACCCAGAGCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAATTTATTGGGCTTCTACTCGTGAAACCGGGGTCCCGGATCGTTT<br>TAGCGGCTCTGGATCCGGCACTGATTTTACCCTGACCATTTCGTCCCTGC<br>AAGCTGAAGACGTGGCGGTGTATTATTGCCAGCAGTATGCTTATGAGCCT<br>AATACCTTTGGCCAGGGTACGAAAGTTGAAATTAAACGTACG |

TABLE E-continued

LISTING OF SEQUENCES OF THE INVENTION

| Ab Ref. No. -<br>Chain Type | SEQ ID<br>NO. | SEQUENCE |
|---|---|---|
| 05101 VL | 10 | GATATCGTGATGACCCAGAGCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAATTTATTGGGCTTCTACTCGTGAAAGCGGGGTCCCGGATCGTTT<br>TAGCGGCTCTGGATCCGGCACTGATTTTACCCTGACCATTTCGTCCCTGC<br>AAGCTGAAGACGTGGCGGTGTATTATTGCCTTCAGTATGCTTTTTCTCCT<br>TGGACCTTTGGCCAGGGTACGAAAGTTGAAATTAAACGTACG |
| 04541 VL | 11 | GATATCGAACTGACCCAGCCGCCTTCAGTGAGCGTTGCACCAGGTCAGAC<br>CGCGCGTATCTCGTGTAGCGGCGATAATATTGGTTCTTATTATGTTTATT<br>GGTACCAGCAGAAACCCGGGCAGGCGCCAGTTCTTGTGATTTATGATGAT<br>AATGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGTCTTATGATTTTCCTTCTATTGTGTTTGGCGGCGGC<br>ACGAAGTTAACCGTTCTTGGCCAG |
| 05093 VL | 12 | GATATCGAACTGACCCAGCCGCCTTCAGTGAGCGTTGCACCAGGTCAGAC<br>CGCGCGTATCTCGTGTAGCGGCGATAATATTGGTTCTTATTATGTTTATT<br>GGTACCAGCAGAAACCCGGGCAGGCGCCAGTTCTTGTGATTTATGATGAT<br>AATGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGTCTTATGATTCTTATATTTTTGTGTTTGGCGGCGGC<br>ACGAAGTTAACCGTTCTTGGCCAG |
| 05094 VL | 13 | GATATCGAACTGACCCAGCCGCCTTCAGTGAGCGTTGCACCAGGTCAGAC<br>CGCGCGTATCTCGTGTAGCGGCGATAATATTGGTTCTTATTATGTTTATT<br>GGTACCAGCAGAAACCCGGGCAGGCGCCAGTTCTTGTGATTTATGATGAT<br>AATGATCGTCCCTCACGCATCCCGGAACGCTTTAGCGGATCCAACAGCGG<br>CAACACCGCGACCCTGACCATTAGCGGCACTCAGGCGGAAGACGAAGCGG<br>ATTATTATTGCTCTACTTATGATGCTTTTACTTTTGTGTTTGGCGGCGGC<br>ACGAAGTTAACCGTTCTTGGCCAG |
| 05095 VL | 14 | GATATCGAACTGACCCAGCCGCCTTCAGTGAGCGTTGCACCAGGTCAGAC<br>CGCGCGTATCTCGTGTAGCGGCGATAATATTGGTTCTTATTATGTTTATT<br>GGTACCAGCAGAAACCCGGGCAGGCGCCAGTTCTTGTGATTTATGATGAT<br>AATGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGTCTTATGATAAGTATGTTTTTGTGTTTGGCGGCGGC<br>ACGAAGTTAACCGTTCTTGGCCAG |
| 04537 VL | 15 | GATATCGAACTGACCCAGCCGCCTTCAGTGAGCGTTGCACCAGGTCAGAC<br>CGCGCGTATCTCGTGTAGCGGCGATTCTCTTCGTTCTTATTTTGTTTCTT<br>GGTACCAGCAGAAACCCGGGCAGGCGCCAGTTCTTGTGATTTATGATGAT<br>GATGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCGCTTCTTGGGATACTCTTTCTGATGTTGAGGTGTTTGGC<br>GGCGGCACGAAGTTAACCGTTCTTGGCCAG |
| 05102 VL | 16 | GATATCGAACTGACCCAGCCGCCTTCAGTGAGCGTTGCACCAGGTCAGAC<br>CGCGCGTATCTCGTGTAGCGGCGATTCTCTTCGTTCTTATTTTGTTTCTT<br>GGTACCAGCAGAAACCCGGGCAGGCGCCAGTTCTTGTGATTTATGATGAT<br>GATGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCGCTTCTTGGGATCCTCCTTCTGCTTTTGAGGTGTTTGGC<br>GGCGGCACGAAGTTAACCGTTCTTGGCCAG |
| 05105 VL | 17 | GATATCGAACTGACCCAGCCGCCTTCAGTGAGCGTTGCACCAGGTCAGAC<br>CGCGCGTATCTCGTGTAGCGGCGATTCTCTTCGTTCTTATTTTGTTTCTT<br>GGTACCAGCAGAAACCCGGGCAGGCGCCAGTTCTTGTGATTTATGATGAT<br>GATGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCGCTTCTTGGGATAATGATCATTTTGAGGTGTTTGGCGGC<br>GGCACGAAGTTAACCGTTCTTGGCCAG |
| 04690 VL | 18 | GATATCGAACTGACCCAGCCGCCTTCAGTGAGCGTTGCACCAGGTCAGAC<br>CGCGCGTATCTCGTGTAGCGGCGATAAGCTTGGTTCTTATTTTGTTTATT<br>GGTACCAGCAGAAACCCGGGCAGGCGCCAGTTCTTGTGATTTATGATGAT<br>GATAATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGTCTTTTGGTATTTCTAATTTTATGTGTTTGGCGGC<br>GGCACGAAGTTAACCGTTCTTGGCCAG |

TABLE E-continued

LISTING OF SEQUENCES OF THE INVENTION

| Ab Ref. No. -<br>Chain Type | SEQ ID<br>NO. | SEQUENCE |
|---|---|---|
| 05106 VL | 19 | GATATCGAACTGACCCAGCCGCCTTCAGTGAGCGTTGCACCAGGTCAGAC<br>CGCGCGTATCTCGTGTAGCGGCGATAAGCTTGGTTCTTATTTTGTTTATT<br>GGTACCAGCAGAAACCCGGGCAGGCGCCAGTTCTTGTGATTTATGATGAT<br>GATAATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCGGTTCTTGGGCTTATCTTGGTGATGTGTTTGGCGGCGGC<br>ACGAAGTTAACCGTTCTTGGCCAG |
| 04682 VL | 20 | CAGGTGCAATTGGTTCAGAGCGGCGCGGAAGTGAAAAAACCGGGCGAAAG<br>CCTGAAAATTAGCTGCAAAGGTTCCGGATATTCCTTTACTAATTATGGTA<br>TTGCTTGGGTGCGCCAGATGCCTGGGAAGGGTCTCGAGTGGATGGGCATT<br>ATCTATCCGTCTGATAGCTATACCAATTATTCTCCGAGCTTTCAGGGCCA<br>GGTGACCATTAGCGCGGATAAAAGCATTAGCACCGCGTATCTTCAATGGA<br>GCAGCCTGAAAGCGAGCGATACGGCCATGTATTATTGCGCGCGTATGTCT<br>TATGATTATCAGCATCAGGCTCCTTCTATGGATTCTTGGGGCCAAGGCAC<br>CCTGGTGACGGTTAGCTCA |
| 04536 VH | 21 | CAGGTGCAATTGGTTCAGAGCGGCGCGGAAGTGAAAAAACCGGGCGCGAG<br>CGTGAAAGTGAGCTGCAAAGCCTCCGGATATACCTTTACTGGTTATTATA<br>TGAATTGGGTCCGCCAAGCCCCTGGGCAGGGTCTCGAGTGGATGGGCATT<br>ATCAATCCGTGGACTGGCATACGAATTACGCGCAGAAAGTTTCAGGGCCG<br>GGTGACCATGACCCGTGATACCAGCATTAGCACCGCGTATATGGAACTGA<br>GCAGCCTGCGTAGCGAAGATACGGCCGTGTATTATTGCGCGCGTGATCCT<br>GGTTTTTTTTATTATACTCCTTCTGATCTTTGGGGCCAAGGCACCCTGGT<br>GACGGTTAGCTCA |
| 05078 VH | 22 | CAGGTGCAATTGGTTCAGAGCGGCGCGGAAGTGAAAAAACCGGGCGCGAG<br>CGTGAAAGTGAGCTGCAAAGCCTCCGGATATACCTTTACTGGTTATTATA<br>TGAATTGGGTCCGCCAAGCCCCTGGGCAGGGTCTCGAGTGGATGGGCATT<br>ATTGATCCTTGGAATGGTCAGACTAATTATGCTCAGAAGTTTCAGGGTCG<br>GGTCACCATGACCCGTGATACCAGCATTAGCACCGCGTATATGGAACTGA<br>GCAGCCTGCGTAGCGAAGATACGGCCGTGTATTATTGCGCGCGTGATCCT<br>GGTTTTTTTTATTATACTCCTTCTGATCTTTGGGGCCAAGGCACCCTGGT<br>GACGGTTAGCTCA |
| 05079 VH | 23 | CAGGTGCAATTGGTTCAGAGCGGCGCGGAAGTGAAAAAACCGGGCGCGAG<br>CGTGAAAGTGAGCTGCAAAGCCTCCGGATATACCTTTACTGGTTATTATA<br>TGAATTGGGTCCGCCAAGCCCCTGGGCAGGGTCTCGAGTGGATGGGCGTT<br>ATTGATCCTTGGAATGGTATTACTAATTATGCTCAGAAGTTTCAGGGTCG<br>GGTCACCATGACCCGTGATACCAGCATTAGCACCGCGTATATGGAACTGA<br>GCAGCCTGCGTAGCGAAGATACGGCCGTGTATTATTGCGCGCGTGATCCT<br>GGTTTTTTTTATTATACTCCTTCTGATCTTTGGGGCCAAGGCACCCTGGT<br>GACGGTTAGCTCA |
| 04687 VH | 24 | CAGGTGCAATTGGTTCAGTCTGGCGCGGAAGTGAAAAAACCGGGCAGCAG<br>CGTGAAAGTGAGCTGCAAAGCCTCCGGAGGCACTTTTTCTTCTTATGCTA<br>TTTCTTGGGTGCGCCAAGCCCCTGGGCAGGGTCTCGAGTGGATGGGCGGT<br>ATCGATCCGTTTGGCACTGCGAATTACGCGCAGAAGTTTCAGGGCCGGGT<br>GACCATTACCGCGGATGAAAGCACCAGCACCGCGTATATGGAACTGAGCA<br>GCCTGCGTAGCGAAGATACGGCCGTGTATTATTGCGCGCGTGTTTATCAG<br>GATGTTTGGGGCCAAGGCACCCTGGTGACGGTTAGCTCA |
| 05081 VH | 25 | CAGGTGCAATTGGTTCAGTCTGGCGCGGAAGTGAAAAAACCGGGCAGCAG<br>CGTGAAAGTGAGCTGCAAAGCCTCCGGAGGCACTTTTTCTTCTTATGCTA<br>TTTCTTGGGTGCGCCAAGCCCCTGGGCAGGGTCTCGAGTGGATGGGCGGT<br>ATTGATCCTATTATGGGTACTGAGTATGCTCAGAAGTTTCAGGGTCGGGT<br>GACCATTACCGCGGATGAAAGCACCAGCACCGCGTATATGGAACTGAGCA<br>GCCTGCGTAGCGAAGATACGGCCGTGTATTATTGCGCGCGTGTTTATCAG<br>GATGTTTGGGGCCAAGGCACCCTGGTGACGGTTAGCTCA |
| 05082 VH | 26 | CAGGTGCAATTGGTTCAGTCTGGCGCGGAAGTGAAAAAACCGGGCAGCAG<br>CGTGAAAGTGAGCTGCAAAGCCTCCGGAGGCACTTTTTCTTCTTATGCTA<br>TTTCTTGGGTGCGCCAAGCCCCTGGGCAGGGTCTCGAGTGGATGGGCGAG<br>ATTGATCCTGTTATTGGTGAGACTGATTATGCTCAGAAGTTTCAGGGTCG<br>GGTGACCATTACCGCGGATGAAAGCACCAGCACCGCGTATATGGAACTGA<br>GCAGCCTGCGTAGCGAAGATACGGCCGTGTATTATTGCGCGCGTGTTTAT<br>CAGGATGTTTGGGGCCAAGGCACCCTGGTGACGGTTAGCTCA |

TABLE E-continued

LISTING OF SEQUENCES OF THE INVENTION

| Ab Ref. No. - Chain Type | SEQ ID NO. | SEQUENCE |
|---|---|---|
| 04541 VH | 27 | CAGGTGCAATTGCAAGAAAGTGGTCCGGGCCTGGTGAAACCGGGCGAAAC CCTGAGCCTGACCTGCACCGTTTCCGGAGGTAGCATTTCTTCTTCTTCTT ATTATTGGAATTGGATTCGCCAGGCCCCTGGGAAGGGTCTCGAGTGGATT GGCGAGATCTATTTTGGCTGGACCTATTATAATCCGAGCCTGAAAGGCCG GGTGACCATTAGCGTTGATACTTCGAAAAACCAGTTTAGCCTGAAACTGA GCAGCGTGACGGCGGAAGATACGGCCGTGTATTATTGCGCGCGTGGTTAT GAGTTTCATGGTTAThCTACTTTTGATTATTGGGGCCAAGGCACCCTGGT GACGGTTAGCTCA |
| 04537 VH | 28 | CAGGTGCAATTGGTTCAGAGCGGCGCGGAAGTGAAAAAACCGGGCGAAAG CCTGAAAATTAGCTGCAAAGGTTCCGGATATTCCTTTTCTAATTATTGGA TTGGTTGGGTGCGCCAGATGCCTGGGAAGGGTCTCGAGTGGATGGGCTTT ATCTTTCCGGATACTAGCTATACCCGTTATTCTCCGAGCTTTCAGGGCCA GGTGACCATTAGCGCGGATAAAAGCATTAGCACCGCGTATCTTCAATGGA GCAGCCTGAAAGCGAGCGATACGGCCATGTATTATTGCGCGCGTGTTAAG CTTATTACTGATTATTGGGGCCAAGGCACCCTGGTGACGGTAGCTCA |
| 04690 VH | 29 | CAGGTGCAATTGCAACAGTCTGGTCCGGGCCTGGTGAAACCGAGCCAAAC CCTGAGCCTGACCTGTGCGATTTCCGGAGATAGCGTGAGCTCTAATTCTG CTGCTTGGGGTTGGATTCGCCAGTCTCCTGGGCGTGGCCTCGAGTGGCTG GGCCGTATCTATTATCGTAGCAAGTGGGTTAACGATTATGCGGTGAGCGT GAAAAGCCGGATTACCATCAACCCGGATACTTCGAAAAACCAGTTTAGCC TGCAACTGAACAGCGTGACCCCGGAAGATACGGCCGTGTATTATTGCGCG CGTCAGGGTGCTGTTTATCCTGGTCCTTATGGTTTTGATGTTTGGGGCCA AGGCACCCTGGTGACGGTTAGCTCA |
| 04682 VH | 30 | GATATCGTGCTGACCCAGCCGCCTTCAGTGAGTGGCGCACCAGGTCAGCG TGTGACCATCTCGTGTAGCGGCAGCAGCAGCAACATTGGTTCTAATTATG TGATTTGGTACCAGCAGTTGCCCGGGRCGGCGCCGAAACTTCTGATTTAT GATGATACTAATCGTCCCTCAGGCGTGCCGGATCGTTTTAGCGGATCCAA AAGCGGCACCAGCGCGAGCCTTGCGATTACGGGCCTGCAAAGCGAAGACG AAGCGGATTATTATTGCTCTACTTATGATAATTATCAGGCTGGTTGGGTG TTTGGCGGCGGCACGAAGTTAACCGTTCTTGGCCAG |
| 04536 VL | 31 | DIELTQPPSVSVAPGQTARISCSGDSIGNKYVHWYQQKPGQAPVLVIYAD SDRPSGIPERFSGSNSGNTATLTISGTQAEDEADYYCQAYDSSMLRVFGG GTKLTVLGQ |
| 05087 VL | 32 | DIELTQPPSVSVAPGQTARISCSGDSIGNKYVHWYQQKPGQAPVLVIYAD SDRPSGIPERFSGSNSGNTATLTISGTQAEDEADYYCQSYANYHDSWVFG GGTKLTVLGQ |
| 05088 VL | 33 | DIELTQPPSVSVAPGQTARISCSGDSIGNKYVHWYQQKPGQAPVLVIYAD SDRPSGIPERFSGSNSGNTATLTISGTQAEDEADYYCQSYASDYTSWVFG GGTKLTVLGQ |
| 05091 VL | 34 | DIELTQPPSVSVAPGQTARISCSGDSIGNKYVHWYQQKPGQAFVLVIYAD SDRPSGIPERFSGSNSGWTATLTISGTQAEDEADYYC0SYAHYHDIWVFG GGTKLTVLGQ |
| 05092 VL | 35 | DIELTQPPSVSVAPGQTARISCSGDSIGNKYVHWYQQKPGQAPVLVIYAD SDRPSGIPERFSGSNSGNTATLTISGTQAEDEADYYCQAHDSLYSRVFGG GTKLTVLGQ |
| 04687 VL | 36 | DIVMTQSPDSLAVSLGERATINCRSSQSILYGINNNFLGWYQQKPGQPPK LLIYWASTRESGVPDRFSGSGSGTDFTLTISSLQAEDVAVYYCQQYYNHP HTFGQGTKVEIKRT |
| 05097 VL | 37 | DIVMTQSPDSLAVSLGERATINCRSSQSILYGINNNELGWYQQKPGQPPK LLIYWASTRESGVPDRFSGSGSGTDFTLTISSLQAEDVAVYYCQQYAFGW TFGQGTKVEIKRT |
| 05098 VL | 38 | DIVMTQSPDSLAVSLGERATINCRSSQSILYGINNNFLGWYQQKPGQPPK LLIYWASTRESGVPDRFSGSGSGTDFTLTISSLQAEDVAVYYCLQYSDEP WTFGQGTKVEIKRT |
| 05100 VL | 39 | DIVMTQSPDSLAVSLGERATINCRSSQSILYGINNNFLGWYQQKPGQPPK LLIYWASTRESGVPDRFSGSGSGTDFTLTISSLQAEDVAVYYCQQYAYEP NTFGQGTKVEIKRT |
| 05101 VL | 40 | DIVMTQSPDSLAVSLGERATINCRSSQSILYGINNNFLGWYQQKPGQPPK LLEYWASTRESGVPDRFSGSGSGTDFTLTISSLQAEDVAVYYCLQYAFSP WTFGQGTKVEIKRT |

TABLE E-continued

LISTING OF SEQUENCES OF THE INVENTION

| Ab Ref. No. - Chain Type | SEQ ID NO. | SEQUENCE |
|---|---|---|
| 04541 VL | 41 | VLDIELTQPPSVSVAPGQTARISCSGDNIGSYYVYWYQQKPGQAPVLVIY DDNDRPSGIPERFSGSNSGNTATLTISGTQAEDEADYYCQSYDFPSIVFG GGTKLTVLGQ |
| 05093 VL | 42 | DIELTQPPSVSVAPGQTARISCSGDNIGSYYVYWYQQKPGQAPVLVIYDD NDRPSGIPERFSGSNSGNTATLTISGTQAEDEADYYCQSYDSYIFVGGGG TKLTVLGQ |
| 05094 VL | 43 | DIELTQPPSVSVAPGQTARISCSGDNIGSYYVYWYQQKPGQAPVLVIYDD NDRPSGIPERFSGSNSGNTATLTISGTQAEDEADYYCSTYDAFTFVFGGG TKLTVLGQ |
| 05095 VL | 44 | DIELTQPPSVSVAPGQTARISCSGDNIGSYYVYwYQQKPGQAPVLVIYDD NDRPSGIPERFSGSNSGNTATLTISGTQAEDEADYYCQSYDKYVFVFGGG TKLTVLGQ |
| 04537 VL | 45 | DIELTQPPSVSVAPGQTARISCSGDSLRSYFVSwYQQKPGQAPVLVIYDD DDRPSGIPERFSGSNSGNTATLTISGTQAEDEADYYCASWDTLSDVEVFG GGTKLTVLGQ |
| 05102 VL | 46 | DIELTQPPSVSVAPGQTARISCSGDSLRSYFVSWYQQKPGQAPVLVIYDD DDRPSGIPERFSGSNSGNTATLTISGTQAEDEADYYCASWDPPSAFEVFG GGTKITVLGQ |
| 05105 VL | 47 | DIELTQPPSVSVAPGQTARISCSGDSLRSYFVSWYQQKPGQAPVLVIYDD DDRPSGIPERFSGSNSGNTATLTISGTQABDEADYYCASWDNDHFEVFGG GTKLTVLGQ |
| 04690 VL | 48 | DIELTQPPSVSVAEGQTARISCSGDKLGSYFVYWYQQKPGQAPVLVIYDD DNRPSGIPERFSGSNSGNTATLTISGTQAEDEADYYCQSFGISNFYVFGG GTKLTVLGQ |
| 05106 VL | 49 | DIELTQPPSVSVAPGQTARISCSGDKLGSYFVYWYQQKPGQAPVLVIYDD DNRPSGIPERFSGSNSGNTATLTISGTQAEDEADYYCGSWAYLGDVFGGG TKLTVLGQ |
| 04682 VL | 50 | DIVLTQPPSVSGAPGQRVTISCSGSSSNIGSNYVIWYQQLPGTAPKLLIY DDTNRPSGVPDRFSGSKSGTSASLAITGLQSEDEADYYCSTYDNYQAGWV FGGGTKLTVLGQ |
| 05174 VL | 51 | DIELTQPPSVSVAPGQTARISCSGDSIGNKYVHWYQQKPGQAPVLVIYAD SDRPSGIPERFSGSNSGNTATLTISGTQAEDEADYYCQSYANYHDSWVFG GGTKLTVLGQ |
| 05184 VL | 52 | DIELTQPPSVSVAPGQTARISCSGDSIGNKYVHWYQQKPGQAPVLVIYAD SDRPSGIPERFSGSNSGNTATLTISGTQAEDEADYYCQSYAHYHDIWVFG GGTKLTVLGQ |
| 05185 VL | 53 | DIVMTQSPDSLAVSLGERATINCRSSQSILYGINNNFLGWYQQKPGQPPK LLIYWASTRESGVPDRFSGSGSGTDFTLTISSLQAEDVAVYYCQQYAYEP NTFGQGTKVEIKRT |
| 05186 VL | 54 | DIVMTQSPDSLAVSLGERATINCRSSQSILYGINNNFLGWYQQKPGQPPK LLIYWASTRESGVPDRFSGSGSGTDFTLTISSLQAEDVAVYYCLQYAFSP WTFGQGTKVEIKRT |
| 04536 VH | 55 | QVQLVQSGAEVKKPGASVKVSCKASGYTFTGYYMNWVRQAPGQGLEWMGI INPWTGNTNYAQKFQGRVTMTRDTSISTAYMELSSLRSEDTAVYYCARDP GFFYYTPSDLWGQGTLVTVSS |
| 05078 VH | 56 | QVQLVQSGAEVKKPGASVKVSCKASGYTFTGYYMNWVRQAPGQGLEWMGI IDPWNGQTNYAQKFQGRVTMTRDTSISTAYNELSSLRSEDTAVYYCARDP GFFYYTPSDLWGQGTLVTVSS |
| 05079 VH | 57 | QVQLVQSGAEVKKPGASVKVSCKASGYTFTGYYMNWVRQAPGQGLEWMGV IDPWNGITNYAQKFQGRVTMTRDTSISTAYMELSSLRSEDTAVYYCARDP GFFYYTPSDLWGQGTLVTVSS |
| 04687 VH | 58 | QVQLVQSGAEVKKPGSSVKVSCKASGGTFSSYAISWVRQAPGQGLEWMGG IDPFGTANYAQKFQGRVTITADESTSTAYMELSSLRSEDTAVYYCAIWQ DVWGQGTLVTVSS |
| 05082 VH | 59 | QVQLVQSGAEVKKPGSSVKVSCKASGGTFSSYAISWVRQAPGQGLEWMGG IDPIMGTEYAQKFQGRVTITADESTSTAYMELSSLRSEDTAVYYCARVYQ DVWGQGTLVTVSS |

TABLE E-continued

LISTING OF SEQUENCES OF THE INVENTION

| Ab Ref. No. -<br>Chain Type | SEQ ID<br>NO. | SEQUENCE |
|---|---|---|
| 05082 VH | 60 | QVQLVQSGAEVKKPGSSVKVSCKASGGTFSSYAISWVRQAPGQGLEWMGE<br>IDPVIGETDYAQKFQGRVTITADESTSTAYMELSSLRSEDTAVYYCARVY<br>QDVWGQGTLVTVSS |
| 04541 VH | 61 | QVQLQESGPGLVKPGETLSLTCTVSGGSISSSSYYWNWIRQAPGKGLEWI<br>GEIYFGWTYYNPSLKGRVTISVDTSKNQFSLKLSSVTAEDTAVYYCARGY<br>EFHGYTTFDYWGQGTLVTVSS |
| 04537 VH | 62 | QVQLVQSGAEVKKPGESLKISCKGSGYSFSNYWIGWVRQMPGKGLEWMGF<br>IFPDTSYTRYSPSFQGQVTISADKSISTAYLQWSSLKASDTAMYYCARVK<br>LITDYWGQGTLVTVSS |
| 04690 VH | 63 | QVQLQQSGPGLVKPSQTLSLTCAISGDSVSSNSAAWGWIRQSPGRGLEWL<br>GRIYYRSKWVNDYAVSVKSRITINPDTSKNQESLQLNSVTPEDTAVYYCA<br>RQGAVYPGPYGFDVWGQGTLVTVSS |
| 04682 VH | 64 | QVQLVQSGAEVKKPGESLKISCKGSGYSFTNYGIAWVRQMPGKGLEWMGI<br>IYPSDSYTNYSPSFQGQVTISADKSISTAYLQWSSLKASDTAMYYCARMS<br>YDYQHQAPSMDSWGQGTLVTVSS |
| 05087 VH | 65 | QVQLVQSGAEVKKPGASVKVSCKASGYTFTGYYMNWVRQAPGQGLEWNGI<br>INPWTGNTNYAQKFQGRVTMTRDTSISTAYMELSSLRSEDTAVYYCARDP<br>GFFYYTPSDLWGQGTLVTVSS |
| 05091 VH | 66 | QVQLVQSGAEVKKPGASVKVSCKASGYTFTGYYMNWVRQAPGQGLEWMGI<br>INPWTGNTNYAQKFQGRVTMTRDTSISTAYMELSSLRSEDTAVYYCARDP<br>GFFYYTPSDLWGQGTLVTVSS |
| 05097 VH | 67 | QVQLVQSGAEVKKPGSSVKVSCKASGGTFSSYAISWVRQAPGQGLEWMGG<br>IDPFGTANYAQKFQGRVTITADESTSTAYMEL8SLRSEDTAVYYCARVYQ<br>DVWGQGTLVTVSS |
| 05098 VH | 68 | QVQLVQSGAEVKKPGSSVKVSCKASGGTFSSYAISWVRQAPGQGLEWMGG<br>IDPFGTANYAQKFQGRVTITADESTSTAYMELSSLRSEDTAVYYCARVYQ<br>DVWGQGTLVTVSS |
| 05174 VH | 69 | QVQLVQSGAEVKKPGASVKVSCKASGYTFTGYYMNWVRQAPGQGLEWMGI<br>IDPWNGQTNYAQKFQGRVTMTRDTSISTAYMELSSLRSEDTAVYYCARDP<br>GFFYYTPSDLWGQGTLVTVSS |
| 05184 VH | 70 | QVQLVQSGAEVKKPGASVKVSCKASGYTFTGYYMNWVRQAPGQGLEWMGI<br>IDPWNGQTNYAQKFQGRVTMTRDTSISTAYMELSSLRSEDTAVYYCARDP<br>GFFYYTPSDLWGQGTLVTVSS |
| 05185 VH | 71 | QVQLVQSGAEVKKPGSSVKVSCKASGGTFSSYAISWVRQAPGQGLEWMGG<br>IDPIMGTEYAQPCFQGRVTITADESTSTAYMELSSLRSEDTAVYCARVYQ<br>DVWGQCTLVTVSS |
| 05186 VH | 72 | QVQLVQSGAEVKKPGSSVKVSCKASGGTFSSYAISWVRQAPGOGLEWMGG<br>IDPIMGTEYAQKFOGRVTITAPESTSTAYMELSSLRSEDTAVYYCARVYQ<br>DVWGQGTLVTVSS |
| 05091_Ig<br>lambda | 73 | GATATCGAACTGACCCAGCCGCCTTCAGTGAGCGTTGCACCAGGTCAGAC<br>CGCGCGTATCTCGTGTAGCGGCGATTCTATTGGTAATAAGTATGTTCATT<br>GGTACCAGCAGAAACCCGGGCAGGCGCCAGTTCTTGTGATTTATGCTGAT<br>TCTGATCGTCCCTCAGGCATCCCGGAACGCTTTAGCGGATCCAACAGCGG<br>CAACACCGCGACCCTGACCATTAGCGGCACTCAGGCGGAAGACGAAGCGG<br>ATTATTATTGCCAGTCTTATGCTCATTATCATGATATTTGGGTGTTTGGC<br>GGCGGCACGAAGTTAACCGTCCTAGGTCAGCCCAAGGCTGCCCCCTCGGT<br>CACTCTGTTCCCGCCCTCCTCTGAGGAGCTTCAAGCCAACAAGGCCACAC<br>TGGTGTGTCTCATAAGTGACTTCTACCCGGGAGCCGTGACAGTGGCCTGG<br>AAGGCAGATAGCAGCCCCGTCAAGGCGGGAGTGGAGACCACCACACCCTC<br>CAAACAAAGCAACAACAAGTACGCGGCCAGCAGCTATCTGAGCCTGACGC<br>CTGAGCAGTGGAAGTCCCACAGAAGCTACAGCTGCCAGGTCACGCATGAA<br>GGGAGCACCGTGGAGAAGACAGTGGCCCCTACAGAATGTTCA |
| 05185_Ig<br>kappa | 74 | GATATCGTGATGACCCAGAGCCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAAATTTATTGGGCTTCTACTCGTGAAAGCGGGGTCCCGGATCGTTT<br>TAGCGGCTCTGGATCCGGCACTGATTTTACCCTGACCATTTCGTCCCTGC<br>AAGCTGAAGACGTGGCGGTGTATTATTGCCAGCAGTATGCTTATGAGCCT<br>AATACCTTTGGCCAGGGTACGAAAGTTGAAATTAAACGTACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA |

TABLE E-continued

LISTING OF SEQUENCES OF THE INVENTION

| Ab Ref. No. - Chain Type | SEQ ID NO. | SEQUENCE |
|---|---|---|
| | | GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTAG |
| 05098_Ig kappa | 75 | GATATCGTGATGACCCAGAGCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAATTTATTGGGCTTCTACTCGTGAAAGCGGGGTCCCGGATCGTTT<br>TAGCGGCTCTGGATCCGGCACTGATTTTACCCTGACCATTCGTCCCTGC<br>AAGCTGAAGACGTGGCGGTGTATTATTGCCTTCAGTATTCTGATGAGCCT<br>TGGACCTTTGGCCAGGGTACGAAAGTTGAAATTAAACGTACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTAG |
| 05097_Ig kappa | 76 | GATATCGTGATGACCCAGAGCCCGGATAGCCTGGCGGTGAGCCTGGGCGA<br>ACGTGCGACCATTAACTGCAGAAGCAGCCAGTCTATTCTTTATGGTATTA<br>ACAATAATTTTCTGGGTTGGTACCAGCAGAAACCAGGTCAGCCGCCGAAA<br>CTATTAATTTATTGGGCTTCTACTCGTGAAAGCGGGGTCCCGGATCGTTT<br>TAGCGGCTCTGGATCCGGCACTGATTTTACCCTGACCATTCGTCCCTGC<br>AAGCTGAAGACGTGGCGGTGTATTATTGCCAGCAGTATGCTTTTGGTTGG<br>ACCTTTGGCCAGGGTACGAAAGTTGAAATTAAACGTACGGTGGCTGCACC<br>ATCTGTCTTCATCTTCCCGCCATCTGATGAGCAGTTGAAATCTGGAACTG<br>CCTCTGTTGTGTGCCTGCTGAATAACTTCTATCCCAGAGAGGCCAAAGTA<br>CAGTGGAAGGTGGATAACGCCCTCCAATCGGGTAACTCCCAGGAGAGTGT<br>CACAGAGCAGGACAGCAAGGACAGCACCTACAGCCTCAGCAGCACCCTGA<br>CGCTGAGCAAAGCAGACTACGAGAAACACAAAGTCTACGCCTGCGAAGTC<br>ACCCATCAGGGCCTGAGCTCGCCCGTCACAAAGAGCTTCAACAGGGGAGA<br>GTGTTAG |
| 05091_Ig lambda | 77 | DIELTQPPSVSVAPGQTARISCSGDSIGNKYVHWYQQKPGQAPVLVIYAD<br>SDRPSGIPERFSGSNSGNTATLTISGTQAEDEADYYCQ8YAHYHDIWVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS |
| 05087_Ig lambda | 78 | DIELTQPPSVSVAPGQTARISCSGDSIGNKYVHWYQQKPGQAPVLVIYAD<br>SDRPSGIPERFSGSNSGNTATLTISGTQAEDEADYYCQSYANYHDSWVEG<br>GGTKLTVLGQPKAAPSVTLFPPSSEELQANKATLVCLISDFYPGAVTVAW<br>KAPSSPVKAGVETTTPSKQSNNKYAASSYLSLTPEQWKSHRSYSCQVTHE<br>GSTVEKTVAPTECS |
| 05174_Ig lambda | 79 | DIELTQPPSVSVAPGQTARISCSGDSIGNKYVHWYQQKPGQAPVLVIYAD<br>SDRPSGIPERFSGSNSGNTATLTISGTQAEDEADYYCQSYANYHDSWVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS |
| 05184_Ig lambda | 80 | DIELTQPPSVSVAPGQTARISCSGDSIGNKYVHWYQQKPGQAPVLVIYAD<br>SDRPSGIPERFSGSNSGNTATLTISGTQAEDEADYYCQSYAHYHDIWVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS |
| 05185_Ig kappa | 81 | DIVMTQSPDSIAVSLGERATINCRSSQSILYGINNNFLGWYQQKPGQPPK<br>LLIYWASTRESGVFDRFSGSGSGTDFTLTISSLQAEDVAVYYCQQYAYEP<br>NTFGQGTKVEIKRTVAAPSVFIFPPSDEQLKSGTASVVCLLNNEYPREAK<br>VQWKVDNALQSGNSQESVTEQDSKDSTYSLSSTLTLSKADYEKHKVYACE<br>VTHQGLSSPVTKSFNRGEC |
| 05098_Ig kappa | 82 | DIVMTQSPDSLAVSLGERATINCRS8QSILYGINNNFLGWYQQKPGQPPK<br>LLIYWASTRESGVPDRFSGSGSGTDFTLTISSLQAEDVAVYYCLQYSDEP<br>WTFGQGTKVEIKRTVAAPSVFIFPPSDEQLICSGTASWCLLNNFYPREAK<br>VQWKVDNALQSGNSQESVTEQDSKDSTYSLSSTLTLSKADYEKHKVYACE<br>VTHQGLSSPVTKSFNRGEC |

TABLE E-continued

LISTING OF SEQUENCES OF THE INVENTION

| Ab Ref. No. - Chain Type | SEQ ID NO. | SEQUENCE |
|---|---|---|
| 05097_Ig kappa | 83 | DIVMTQSPDSLAVSLGERATINCRSSQSILYGINNNFLGWYQQKPGQPPK<br>LLIYWASTRESGVPDRFSGSGSGTDFTLTISSLQAEDVAVYYCQQYAFGW<br>TFGQGTKVEIKRTVAAPSVFIFPPSDEQLKSGTASVVCLLNNFYPREAKV<br>QWKVDNALQSGNSQESVTEQDSKDSTYSLSSTLTLSKADYEKHKVYACEV<br>THQGLSSPVTKSFNRGEC |
| 05186_Ig kappa | 84 | DIVMTQSPDSIAVSLGERATINCRSSQSILYGINNNFLGWYQQKPGQPPK<br>LLIYWASTRESGVPDRFSGSGSGTDFTLTISSLQAEDVAVYYCLQYAFSP<br>WTFGQGTKVEIKRTVAAPSVFIFPPSDEQLKSGTASVVCLLNNFYPREAK<br>VQWKVDNALQSGNSQESVTEQDSKDSTYSLSSTLTLSKADYEKHKVYACE<br>VTHQGLSSPVTKSFNRGEC |
| 05091_IgG4 | 85 | CAGGTGCAATTGGTTCAGAGCGGCGCGGAAGTGAAAAAACCGGGCGCGAG<br>CGTGAAAGTGAGCTGCAAAGCCTCCGGATATACCTTTACTGGTTATTATA<br>TGAATTGGGTCCGCCAAGCCCCTGGGCAGGGTCTCGAGTGGATGGGCATT<br>ATCAATCCGTGGACTGGCAATACGAATTACGCGCAGAAGTTTCAGGGCCG<br>GGTGACCATGACCCGTGATACCAGCATTAGCACCGCGTATATGGAACTGA<br>GCAGCCTGCGTAGCGAAGATACGGCCGTGTATTATTGCGCGCGTGATCCT<br>GGTTTTTTTTATTATACTCCTTCTGATCTTTGGGGCCAAGGCACCCTGGT<br>GACGGTTAGCTCAGCTTCCACCAAGGGACCATCCGTCTTCCCCCTGGCGC<br>CCTGCTCCAGGAGCACCTCCGAGAGCACAGCCGCCCTGGGCTGCCTGGTC<br>AAGGACTACTTCCCCGAACCGGTGACGGTGTCGTGGAACTCAGGCGCCCT<br>GACCAGCGGCGTGCACACCTTCCCGGCTGTCCTACAGTCCTCAGGACTCT<br>ACTCCCTCAGCAGCGTGGTGACCCTGCCCTCCAGCAGCTTGGGCACGAAG<br>ACCTACACCTGCAACGTAGATCACAAGCCCAGCAACACCAAGGTGGACAA<br>GAGAGTTGAGTCCAAATATGGTCCCCCATGCCCATCATGCCCACCACCTG<br>AGTTCCTGGGGGGACCATCAGTCTTCCTGTTCCCCCAAAACCCAAGGAC<br>ACTCTCATGATCTCCCGGACCCCTGAGGTCACGTGCGTGGTGGTGGACGT<br>GAGCCAGGAAGACCCCGAGGTCCAGTTCAACTGGTACGTGGATGGCGTGG<br>AGGTGCATAATGCCAAGACAAAGCCGCGGGAGGAGCAGTTCAACAGCACG<br>TACCGTGTGGTCAGCGTCCTCACCGTCCTGCACCAGGACTGGCTGAACGG<br>CAAGGAGTACAAGTGCAAGGTCTCCAACAAAGGCCTCCCGTCCTCCATCG<br>AGAAAACCATCTCCAAAGCCAAAGGGCAGCCCCGAGAGCCACAGGTGTAC<br>ACCCTGCCCCCATCCCAGGAGGAGATGACCAAGAACCAGGTCAGCCTGAC<br>CTGCCTGGTCAAAGGCTTCTACCCCAGCGACATCGCCGTGGAGTGGGAGA<br>GCAATGGGCAGCCGGAGAACAACTACAAGACCACGCCTCCCGTGCTGGAC<br>TCCGACGGCTCCTTCTTCCTCTACAGCAGGCTAACCGTGGACAAGAGCAG<br>GTGGCAGGAGGGGAATGTCTTCTCATGCTCCGTGATGCATGAGGCTCTGC<br>ACAACCACTACACACAGAAGAGCCTCTCCCTGTCTCTGGGTAAATGA |
| 05185_IgG4 | 86 | CAGGTGCAATTGGTTCAGTCTGGCGCGGAAGTGAAAAAACCGGGCAGCAG<br>CGTGAAAGTGAGCTGCAAAGCCTCCGGAGGCACTTTTTCTTCTTATGCTA<br>TTTCTTGGGTGCGCCAAGCCCCTGGGCAGGGTCTCGAGTGGATGGGCGGT<br>ATTGATCCTATTATGGGTACTGAGTATGCTCAGAAGTTTCAGGGTCGGGT<br>GACCATTACCGCGGATGAAAGCACCAGCACCGCGTATATGGAACTGAGCA<br>GCCTGCGTAGCGAAGATACGGCCGTGTATTATTGCGCGCGTGTTTATCAG<br>GATGTTTGGGGCCAAGGCACCCTGdTGACGGTTAGCTCAGCTTCCACCAA<br>GGGACCATCCGTCTTCCCCCTGGCGCCCTGCTCCAGGAGCACCTCCGAGA<br>GCACAGCCGCCCTGGGCTGCCTGGTCAAGGACTACTTCCCCGAACCGGTG<br>ACGGTGTCGTGGAACTCAGGCGCCCTGACCAGCGGCGTGCACACCTTCCC<br>GGCTGTCCTACAGTCCTCAGGACTCTACTCCCTCAGCAGCGTGGTGACCG<br>TGCCCTCCAGCAGCTTGGGCACGAAGACCTACACCTGCAACGTAGATCAC<br>AAGCCCAGCAACACCAAGGTGGACAAGAGAGTTGAGTCCAAATATGGTCC<br>CCCATGCCCATCATGCCCAGCACCTGAGTTCCTGGGGGGACCATCAGTCT<br>TCCTGTTCCCCCCAAAACCCAAGGACACTCTCATGATCTCCCGGACCCCT<br>GAGGTCACGTGCGTGGTGGTGGACGTGAGCCAGGAAGACCCCGAGGTCCA<br>GTTCAACTGGTACGTGGATGGCGTGGAGGTGCATAATGCCAAGACAAAGC<br>CGCGGGAGGAGCAGTTCAACAGCACGTACCGTGTGGTCAGCGTCCTCACC<br>GTCCTGCACCAGGACTGGCTGAACGGCAAGGAGTACAAGTGCAAGGTCTC<br>CAACAAAGGCCTCCCGTCCTCCATCGAGAAAACCATCTCCAAAGCCAAAG<br>GGCAGCCCCGAGAGCCACAGGTGTACACCCTGCCCCCATCCCAGGAGGAG<br>ATGACCAAGAACCAGGTCAGCCTGACCTGCCTGGTCAAAGGCTTCTACCC<br>CAGCGACATCGCCGTGGAGTGGGAGAGCAATGGGCAGCCGGAGAACAACT<br>ACAAGACCACGCCTCCCGTGCTGGACTCCGACGGCTCCTTCTTCCTCTAC<br>AGCAGGCTAACCGTGGACAAGAGCAGGTGGCAGGAGGGGAATGTCTTCTC<br>ATGCTCCGTGATGCATGAGGCTCTGCACAACCACTACACACAGAAGAGCC<br>TCTCCCTGTCTCTGGGTAAATGA |
| 05098_IgG4 | 87 | CAGGTGCAATTGGTTCAGTCTGGCGCGGAAGTGAAAAAACCGGGCAGCAG<br>CGTGAAAGTGAGCTGCAAAGCCTCCGGAGGCACTTTTTCTTCTTATGCTA<br>TTTCTTGGGTGCGCCAAGCCCCTGGGCAGGGTCTCGAGTGGATGGGCGGT<br>ATCGATCCGTTTGGCACTGCGAATTACGCGCAGAAGTTTCAGGGCCGGGT<br>GACCATTACCGCGGATGAAAGCACCAGCACCGCGTATATGGAACTGAGCA<br>GCCTGCGTAGCGAAGATACGGCCGTGTATTATTGCGCGCGTGTTTATCAG<br>GATGTTTGGGGCCAAGGCACCCTGGTGACGGTTAGCTCAGCTTCCACCAA |

TABLE E-continued

LISTING OF SEQUENCES OF THE INVENTION

| Ab Ref. No. -<br>Chain Type | SEQ ID<br>NO. | SEQUENCE |
|---|---|---|
| | | GGGACCATCCGTCTTCCCCCTGGCGCCCTGCTCCAGGAGCACCTCCGAGA<br>GCACAGCCGCCCTGGGCTGCCTGGTCAAGGACTACTTCCCCGAACCGGTG<br>ACGGTGTCGTGGAACTCAGGCGCCCTGACCAGCGGCGTGCACACCTTCCC<br>GGCTGTCCTACAGTCCTCAGGACTCTACTCCCTCAGCAGCGTGGTGACCG<br>TGCCCTCCAGCAGCTTGGGCACGAAGACCTACACCTGCAACGTAGATCAC<br>AAGCCCAGCAACACCAAGGTGGACAAGAGAGTTGAGTCCAAATATGGTCC<br>CCCATGCCCATCATGCCCAGCACCTGAGTTCCTGGGGGGACCATCAGTCT<br>TCCTGTTCCCCCCAAAACCCAAGGACACTCTCATGATCTCCCGGACCCCT<br>GAGGTCACGTGCGTGGTGGTGGACGTGAGCCAGGAAGACCCCGAGGTCCA<br>GTTCAACTGGTACGTGGATGGCGTGGAGGTGCATAATGCCAAGACAAAGC<br>CGCGGGAGGAGCAGTTCAACAGCACGTACCGTGTGGTCAGCGTCCTCACC<br>GTCCTGCACCAGGACTGGCTGAACGGCAAGGAGTACAAGTGCAAGGTCTC<br>CAACAAAGGCCTCCCGTCCTCCATCGAGAAAACCATCTCCAAAGCCAAG<br>GGCAGCCCCGAGAGCCACAGGTGTACACCCTGCCCCCATCCCAGGAGGAG<br>ATGACCAAGAACCAGGTCAGCCTGACCTGCCTGGTCAAAGGCTTCTACCC<br>CAGCGACATCGCCGTGGACTGGGAGAGCAATGGGCAGCCGGAGAACAACT<br>ACAAGACCACGCCTCCCGTGCTGGACTCCGACGGCTCCTTCTTCCTCTAC<br>AGCAGGCTAACCGTGGACAAGAGCAGGTGGCAGGAGGGGAATGTCTTCTC<br>ATGCTCCGTGATGCATGAGGCTCTGCACAACCACTACACACAGAAGAGCC<br>TCTCCCTGTCTCTGGGTAAATGA |
| 05097_IgG4 | 88 | CAGGTGCAATTGGTTCAGTCTGGCGCGGAAGTGAAAAAACCGGGCAGCAG<br>CGTGAAAGTGAGCTGCAAAGCCTCCGGAGGCACTTTTTCTTCTTATGCTA<br>TTTCTTGGGTGCGCCAAGCCCCTGGGCAGGGTCTCGAGTGGATGGGCGGT<br>ATCGATCCGTTTGGCACTGCGAATTACGCGCAGAAGTTTCAGGGCCGGGT<br>GACCATTACCGCGGATGAAAGCACCAGCACCGCGTATATGGAACTGAGCA<br>GCCTGCGTAGCGAAGATACGGCCGTGTATTATTGCGCGCGTGTTTATCAG<br>GATGTTTGGGGCCAAGGCACCCTGGTGACGGTTAGCTCAGCTTCCACCAA<br>GGGACCATCCGTCTTCCCCCTGGCGCCCTGCTCCAGGAGCACCTCCGAGA<br>GCACAGCCGCCCTGGGCTGCCTGGTCAAGGACTACTTCCCCGAACCGGTG<br>ACGGTGTCGTGGAACTCAGGCGCCCTGACCAGCGGCGTGCACACCTTCCC<br>GGCTGTCCTACAGTCCTCAGGACTCTACTCCCTCAGCAGCGTGGTGACCG<br>TGCCCTCCAGCAGCTTGGGCACGAAGACCTACACCTGCAACGTAGATCAC<br>AAGCCCAGCAACACCAAGGTGGACAAGAGAGTTGAGTCCAAATATGGTCC<br>CCCATGCCCATCATGCCCAGCACCTGAGTTCCTGGGGGGACCATCAGTCT<br>TCCTGTTCCCCCCAAAACCCAAGGACACTCTCATGATCTCCCGGACCCCT<br>GAGGTCACGTGCGTGGTGGTGGACGTGAGCCAGGAAGACCCCGAGGTCCA<br>GTTCAACTGGTACGTGGATGGCGTGGAGGTGCATAATGCCAAGACAAAGC<br>CGCGGGAGGAGCAGTTCAACAGCACGTACCGTGTGGTCAGCGTCCTCACC<br>GTCCTGCACCAGGACTGGCTGAACGGCAAGGAGTACAAGTGCAAGGTCTC<br>CAACAAAGGCCTCCCGTCCTCCATCGAGAAAACCATCTCCAAAGCCAAG<br>GGCAGCCCCGAGAGCCACAGGTGTACACCCTGCCCCCATCCCAGGAGGAG<br>ATGACCAAGAACCAGGTCAGCCTGACCTGCCTGGTCAAAGGCTTCTACCC<br>CAGCGACATCGCCGTGGAGTGGGAGAGCAATGGGCAGCCGGAGAACAACT<br>ACAAGACCACGCCTCCCGTGCTGGACTCCGACGGCTCCTTCTTCCTCTAC<br>AGCAGGCTAACCGTGGACAAGAGCAGGTGGCAGGAGGGGAATGTCTTCTC<br>ATGCTCCGTGATGCATGAGGCTCTGCACAACCACTACACACAGAAGAGCC<br>TCTCCCTGTCTCTGGGTAAATGA |
| 05091_IgG4 | 89 | QVQLVQSGAEVKKPGASVKVSCKASGYTFTGYYMNWVRQAPGQGLEWMGI<br>INPWTGNTNYAQKFQGRVTMTRDTSISTAYMELSSLRSEDTAVYYCARDP<br>GFFYYTPSDLWGQGTLVTVSSASTKGPSVFPLAPCSRSTSESTAALGCLV<br>KDYFPEPVTVSWNSGALTSGVHTFPAVLQSSGLYSLSSVVTVPSSSLGTK<br>TYTCWVDHKPSNTKVDKRVESKYGPPCPSCPAPEFLGGPSVFLFPPKPKD<br>TLMISRTPEVTCVVVDVSQEDPEVQFNWYVDGVEVHNAKTKPREEQFNST<br>YRVVSVLTVLHQDWLNGKEYKCKVSNKGLPSSIEKTISKTKGQPREPQVY<br>TLPPSQEEMTKNQVSLTCLVKGFYPSDIAVEWESNGQPENNYKTTPPVLD<br>SDGSFFLYSRLTVDKSRWQEGNVFSCSVMHEALHNHYTQKSLSLSLGK |
| 05185_IgG4 | 90 | QVQLVQSGAEVKKPGSSVKVSCKASGGTFSSYAISWVRQAPGQGLEWMGG<br>IDPIMGTEYAQKFQGRVTITADESTSTAYMELSSLRSEDTAVYYCARVYQ<br>DVWGQGTLVTVSSASTKGPSVFPLAPCSRSTSESTAALGCLVKDYFPEPV<br>TVSWNSGALTSGVHTFPAVLQSSGLYSLSSVVTVPSSSLGTKTYTCNVDS<br>KPSNTKVDKRVESKYGPPCPSCPAPEFLGGPSVFLFPPKPKDTLMISRTP<br>EVTCVVVDVSQEDPEVQFNWYVDGVEVHNAKTKPREEQFNSTYRVVSVLT<br>VLHQDWLNGKEYKCKVSNKGLPSSIEKTISKAKGQPREPQVYTLPPSQEE<br>MTKNQVSLTCLVKGFYPSDIAVEWESNGQPENNYKTTFPVLDSDGSFFLY<br>SRLTVDKSRWQEGNVFSCSVMHEALHNHYTQKSLSLSLGK |
| 05098_IgG4 | 91 | QVQLVQSGAEVKKPGSSVKVSCKASGGTFSSYAISWVRQAPGQGLEWMGG<br>IDPFGTANYAQKFQGRVTITADESTSTAYMELSSLRSEDTAVYYCARVYQ<br>DVWGQGTLVTVSSASTKGPSVFPLAPCSRSTSESTAALGCLVKDYFPEPV<br>TVSWNSGALTSGVHTFPAVLQSSGLYSLSSVVTVPSSSLGTKTYTCNVDH<br>KPSNTKVDKRVESKYGPPCPSCPAPEFLGGPSVFLFPPKPKDTLMISRTP<br>EVTCVVVDVSQEDPEVQFNWYVDGVEVHNAKTKPREEQFNSTYRVVSVLT |

TABLE E-continued

LISTING OF SEQUENCES OF THE INVENTION

| Ab Ref. No. - Chain Type | SEQ ID NO. | SEQUENCE |
|---|---|---|
| | | VLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLY<br>SRLTVDKSRWQEGNVFSCSVMHEALHNHYTQKSLSLSLGK |
| 05097_IgG4 | 92 | QVQLVQSGAEVKKPGSSVKVSCKASGGTFSSYAISWVRQAPGQGLEWMGG<br>IDPFGTANYAQKFQGRVTITADESTSTAYMELSSLRSEDTAVYYCARVYQ<br>DVWGQGTLVTVSSASTKGPSVFPLAPCSRSTSESTAALGCLVKDYFPEPV<br>TVSWNSGALTSGVHTFPAVLQSSGLYSLSSVVTVPSSSLGTKTYTCNVDH<br>KPSNTKVDKRVESKYGPPCPSCPAPEFLGGPSVFLFPPKPKDTLMISRTP<br>EVTCVVVDVSQEDPEVQFNWYVDGVEVHNAKTKPREEQFNSTYRVVSVLT<br>VLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLY<br>SRLTVDKSRWQEGNVFSCSVMHEALHNHYTQKSLSLSLGK |
| 05087_IgG4 | 93 | QVQLVQSGAEVKKPGASVKVSCKASGYTFTGYYMNWVRQAPGQGLEWMGI<br>INPWTGNTNYAQKFQGRVTMTRDTSISTAYMELSSLRSEDTAVYYCARDP<br>GFFYYTPSDLWGQGTLVTVSSASTKGPSVFPLAPCSRSTSESTAALGCLV<br>KDYFPEPVTVSWNSGALTSGVHTFPAVLQSSGLYSLSSVVTVPSSSLGTK<br>TYTCNVDHKPSNTKVDKRVESKYGPPCPSCPAPEFLGGPSVFLFPPKPKD<br>TLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVY<br>TLPPSQEEMTKNQVSLTCLVKGFYPSDIAVEWESNGQPENNYKTTPPVLD<br>SDGSFFLYSRLTVDXSRWQEGNVFSCSVMHEALHNHYTQKSLSLSLGK |
| 05174_IgG4 | 94 | QVQLVQSGAEVKKPGASVKVSCKASGYTFTGYYMNWVRQAPGQGLEWMGI<br>IDPWNGQTNYAQKFQGRVTMTRDTSISTAYMELSSLRSEDTAVYYCARDP<br>GFFYYTPSDLWGQGTLVTVSSASTKGPSVFPLAPCSRSTSESTAALGCLV<br>KDYFPEPVTVSWNSGALTSGVHTFPAVLQSSGLYSLSSVVTVPSSSLGTK<br>TYTCNVDHKPSNTRVDKRVESKYGPPCPSCPAPEFLGGPSVFLFPPKPKD<br>TLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVY<br>TLPPSQEEMTKNQVSLTCLVKGFYPSDIAVEWESNGQPENNYKTTPPVLD<br>SDGSFFLYSRLTVDKSRWQEGNVFSCSVMHEALHNHYTQKSLSLSLGK |
| 05184_IgG4 | 95 | QVQLVQSGAEVKKPGASVKVSCKASGYTFTGYYMNWVRQAPGQGLEWMGI<br>IDPWNGQTNYAQKFQGRVTMTRDTSISTAYMELSSLRSEDTAVYYCARDP<br>GFFYYTPSDLWGQGTLVTVSSASTKGPSVFPLAPCSRSTSESTAALGCLV<br>KDYFPEPVTVSWNSGALTSGVHTFPAVLQSSGLYSLSSVVTVPSSSLGTK<br>TYTCNVDHKPSNTKVDKRVESKYGPPCPSCFAPEFLGGPSVFLFPPKPKD<br>TLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVY<br>TLPPSQEEMTKNQVSLTCLVKGFYPSDIAVEWESNGQPENNYKTTPPVLD<br>SDGSFFLYSRLTVDKSRWQEGNVFSCSVMHEALHNHYTQKSLSLSLGK |
| 05186_IgG4 | 96 | QVQLVQSGAEVKKPGSSVKVSCKASGGTFSSYAISWVRQAEGQGLEWMGG<br>IDPIMGTEYAQKFQGRVTITADESTSTAYMELSSLRSEDTAVYYCARVYQ<br>DVWGQGTLVTVSSASTKGPSVFPLAPCSRSTSESTAALGCLVKDYFPEPV<br>TVSWNSGALTSGVHTFFAVLQSSGLYSLSSVVTVPSSSLGTKTYTCNVDH<br>KPSNTKVDKRVESKYGPPCPSCPAPEFLGGPSVFLFPPKPKDTLMISRTP<br>EVTCVVVDVSQEDPEVQNWYVDGVEVHNAKTKPREEQFNSTYRSVVSVLT<br>VLHQDWLNGKEYKCKVSNKGLPSSIEKTISKAKGQPREPQVYTLFPSQEE<br>MTKNQVSLTCLVKGFYPSDIAVEWESNGQPENNYKTTPPVLDSDGSFFLY<br>SRLTVDKSRWQEGNVFSCSVNHEALHNHYTQKSLSLSLGK |

SEQUENCE LISTING

<160> NUMBER OF SEQ ID NOS: 104

<210> SEQ ID NO 1
<211> LENGTH: 327
<212> TYPE: DNA
<213> ORGANISM: Homo sapiens

<400> SEQUENCE: 1

```
gatatcgaac tgacccagcc gccttcagtg agcgttgcac caggtcagac cgcgcgtatc      60
tcgtgtagcg gcgattctat tggtaataag tatgttcatt ggtaccagca gaaacccggg     120
```

```
caggcgccag ttcttgtgat ttatgctgat tctgatcgtc cctcaggcat cccggaacgc      180
tttagcggat ccaacagcgg caacaccgcg accctgacca ttagcggcac tcaggcggaa      240
gacgaagcgg attattattg ccaggcttat gattcttcta tgcttcgtgt gtttggcggc      300
ggcacgaagt taaccgttct tggccag                                          327

<210> SEQ ID NO 2
<211> LENGTH: 330
<212> TYPE: DNA
<213> ORGANISM: Homo sapiens

<400> SEQUENCE: 2
gatatcgaac tgacccagcc gccttcagtg agcgttgcac caggtcagac cgcgcgtatc      60
tcgtgtagcg gcgattctat tggtaataag tatgttcatt ggtaccagca gaaacccggg     120
caggcgccag ttcttgtgat ttatgctgat tctgatcgtc cctcaggcat cccggaacgc     180
tttagcggat ccaacagcgg caacaccgcg accctgacca ttagcggcac tcaggcggaa     240
gacgaagcgg attattattg ccagtcttat gctaattatc atgattcttg ggtgtttggc     300
ggcggcacga agttaaccgt tcttggccag                                      330

<210> SEQ ID NO 3
<211> LENGTH: 330
<212> TYPE: DNA
<213> ORGANISM: Homo sapiens

<400> SEQUENCE: 3
gatatcgaac tgacccagcc gccttcagtg agcgttgcac caggtcagac cgcgcgtatc      60
tcgtgtagcg gcgattctat tggtaataag tatgttcatt ggtaccagca gaaacccggg     120
caggcgccag ttcttgtgat ttatgctgat tctgatcgtc cctcaggcat cccggaacgc     180
tttagcggat ccaacagcgg caacaccgcg accctgacca ttagcggcac tcaggcggaa     240
gacgaagcgg attattattg ccagtcttat gcttctgatt atacttcttg ggtgtttggc     300
ggcggcacga agttaaccgt tcttggccag                                      330

<210> SEQ ID NO 4
<211> LENGTH: 330
<212> TYPE: DNA
<213> ORGANISM: Homo sapiens

<400> SEQUENCE: 4
gatatcgaac tgacccagcc gccttcagtg agcgttgcac caggtcagac cgcgcgtatc      60
tcgtgtagcg gcgattctat tggtaataag tatgttcatt ggtaccagca gaaacccggg     120
caggcgccag ttcttgtgat ttatgctgat tctgatcgtc cctcaggcat cccggaacgc     180
tttagcggat ccaacagcgg caacaccgcg accctgacca ttagcggcac tcaggcggaa     240
gacgaagcgg attattattg ccagtcttat gctcattatc atgatatttg ggtgtttggc     300
ggcggcacga agttaaccgt tcttggccag                                      330

<210> SEQ ID NO 5
<211> LENGTH: 327
<212> TYPE: DNA
<213> ORGANISM: Homo sapiens

<400> SEQUENCE: 5
gatatcgaac tgacccagcc gccttcagtg agcgttgcac caggtcagac cgcgcgtatc      60
tcgtgtagcg gcgattctat tggtaataag tatgttcatt ggtaccagca gaaacccggg     120
```

```
caggcgccag ttcttgtgat ttatgctgat tctgatcgtc cctcaggcat cccggaacgc        180
tttagcggat ccaacagcgg caacaccgcg accctgacca ttagcggcac tcaggcggaa        240
gacgaagcgg attattattg ccaggctcat gattctcttt attctcgtgt gtttggcggc        300
ggcacgaagt taaccgttct tggccag                                            327

<210> SEQ ID NO 6
<211> LENGTH: 342
<212> TYPE: DNA
<213> ORGANISM: Homo sapiens

<400> SEQUENCE: 6
gatatcgtga tgacccagag cccggatagc ctggcggtga gcctgggcga acgtgcgacc         60
attaactgca gaagcagcca gtctattctt tatggtatta acaataattt tctgggttgg        120
taccagcaga aaccaggtca gccgccgaaa ctattaattt attgggcttc tactcgtgaa        180
agcggggtcc cggatcgttt tagcggctct ggatccggca ctgattttac cctgaccatt        240
tcgtccctgc aagctgaaga cgtggcggtg tattattgcc agcagtatta taatcatcct        300
catacctttg gccagggtac gaaagttgaa attaaacgta cg                           342

<210> SEQ ID NO 7
<211> LENGTH: 339
<212> TYPE: DNA
<213> ORGANISM: Homo sapiens

<400> SEQUENCE: 7
gatatcgtga tgacccagag cccggatagc ctggcggtga gcctgggcga acgtgcgacc         60
attaactgca gaagcagcca gtctattctt tatggtatta acaataattt tctgggttgg        120
taccagcaga aaccaggtca gccgccgaaa ctattaattt attgggcttc tactcgtgaa        180
agcggggtcc cggatcgttt tagcggctct ggatccggca ctgattttac cctgaccatt        240
tcgtccctgc aagctgaaga cgtggcggtg tattattgcc agcagtatgc ttttggttgg        300
acctttggcc agggtacgaa agttgaaatt aaacgtacg                               339

<210> SEQ ID NO 8
<211> LENGTH: 342
<212> TYPE: DNA
<213> ORGANISM: Homo sapiens

<400> SEQUENCE: 8
gatatcgtga tgacccagag cccggatagc ctggcggtga gcctgggcga acgtgcgacc         60
attaactgca gaagcagcca gtctattctt tatggtatta acaataattt tctgggttgg        120
taccagcaga aaccaggtca gccgccgaaa ctattaattt attgggcttc tactcgtgaa        180
agcggggtcc cggatcgttt tagcggctct ggatccggca ctgattttac cctgaccatt        240
tcgtccctgc aagctgaaga cgtggcggtg tattattgcc ttcagtattc tgatgagcct        300
tggacctttg gccagggtac gaaagttgaa attaaacgta cg                           342

<210> SEQ ID NO 9
<211> LENGTH: 342
<212> TYPE: DNA
<213> ORGANISM: Homo sapiens

<400> SEQUENCE: 9
gatatcgtga tgacccagag cccggatagc ctggcggtga gcctgggcga acgtgcgacc         60
attaactgca gaagcagcca gtctattctt tatggtatta acaataattt tctgggttgg        120
```

```
taccagcaga aaccaggtca gccgccgaaa ctattaattt attgggcttc tactcgtgaa    180
agcggggtcc cggatcgttt tagcggctct ggatccggca ctgattttac cctgaccatt    240
tcgtccctgc aagctgaaga cgtggcggtg tattattgcc agcagtatgc ttatgagcct    300
aatacctttg gccagggtac gaaagttgaa attaaacgta cg                       342
```

<210> SEQ ID NO 10
<211> LENGTH: 342
<212> TYPE: DNA
<213> ORGANISM: Homo sapiens

<400> SEQUENCE: 10

```
gatatcgtga tgacccagag cccggatagc ctggcggtga gcctgggcga acgtgcgacc    60
attaactgca gaagcagcca gtctattctt tatggtatta caataatttt ctgggttgg     120 taccagcaga aaccaggtca gccgccgaaa ctattaattt attgggcttc tactcgtgaa    180
agcggggtcc cggatcgttt tagcggctct ggatccggca ctgattttac cctgaccatt    240
tcgtccctgc aagctgaaga cgtggcggtg tattattgcc ttcagtatgc tttttctcct    300
tggacctttg gccagggtac gaaagttgaa attaaacgta cg                       342
```

<210> SEQ ID NO 11
<211> LENGTH: 324
<212> TYPE: DNA
<213> ORGANISM: Homo sapiens

<400> SEQUENCE: 11

```
gatatcgaac tgacccagcc gccttcagtg agcgttgcac caggtcagac cgcgcgtatc    60
tcgtgtagcg gcgataatat tggttcttat tatgtttatt ggtaccagca gaaacccggg    120
caggcgccag ttcttgtgat ttatgatgat aatgatcgtc cctcaggcat cccggaacgc    180
tttagcggat ccaacagcgg caacaccgcg accctgacca ttagcggcac tcaggcggaa    240
gacgaagcgg attattattg ccagtcttat gattttcctt ctattgtgtt tggcggcggc    300
acgaagttaa ccgttcttgg ccag                                            324
```

<210> SEQ ID NO 12
<211> LENGTH: 324
<212> TYPE: DNA
<213> ORGANISM: Homo sapiens

<400> SEQUENCE: 12

```
gatatcgaac tgacccagcc gccttcagtg agcgttgcac caggtcagac cgcgcgtatc    60
tcgtgtagcg gcgataatat tggttcttat tatgtttatt ggtaccagca gaaacccggg    120
caggcgccag ttcttgtgat ttatgatgat aatgatcgtc cctcaggcat cccggaacgc    180
tttagcggat ccaacagcgg caacaccgcg accctgacca ttagcggcac tcaggcggaa    240
gacgaagcgg attattattg ccagtcttat gattcttata ttttgtgtt tggcggcggc    300 acgaagttaa ccgttcttgg ccag                                            324
```

<210> SEQ ID NO 13
<211> LENGTH: 324
<212> TYPE: DNA
<213> ORGANISM: Homo sapiens

<400> SEQUENCE: 13

```
gatatcgaac tgacccagcc gccttcagtg agcgttgcac caggtcagac cgcgcgtatc    60
tcgtgtagcg gcgataatat tggttcttat tatgtttatt ggtaccagca gaaacccggg    120
```

| | |
|---|---|
| caggcgccag ttcttgtgat ttatgatgat aatgatcgtc cctcaggcat cccggaacgc | 180 |
| tttagcggat ccaacagcgg caacaccgcg accctgacca ttagcggcac tcaggcggaa | 240 |
| gacgaagcgg attattattg ctctacttat gatgctttta cttttgtgtt tggcggcggc | 300 |
| acgaagttaa ccgttcttgg ccag | 324 |

<210> SEQ ID NO 14
<211> LENGTH: 324
<212> TYPE: DNA
<213> ORGANISM: Homo sapiens

<400> SEQUENCE: 14

| | |
|---|---|
| gatatcgaac tgacccagcc gccttcagtg agcgttgcac caggtcagac cgcgcgtatc | 60 |
| tcgtgtagcg gcgataatat tggttcttat tatgtttatt ggtaccagca gaaacccggg | 120 |
| caggcgccag ttcttgtgat ttatgatgat aatgatcgtc cctcaggcat cccggaacgc | 180 |
| tttagcggat ccaacagcgg caacaccgcg accctgacca ttagcggcac tcaggcggaa | 240 |
| gacgaagcgg attattattg ccagtcttat gataagtatg tttttgtgtt tggcggcggc | 300 |
| acgaagttaa ccgttcttgg ccag | 324 |

<210> SEQ ID NO 15
<211> LENGTH: 330
<212> TYPE: DNA
<213> ORGANISM: Homo sapiens

<400> SEQUENCE: 15

| | |
|---|---|
| gatatcgaac tgacccagcc gccttcagtg agcgttgcac caggtcagac cgcgcgtatc | 60 |
| tcgtgtagcg gcgattctct tcgttcttat tttgtttctt ggtaccagca gaaacccggg | 120 |
| caggcgccag ttcttgtgat ttatgatgat gatgatcgtc cctcaggcat cccggaacgc | 180 |
| tttagcggat ccaacagcgg caacaccgcg accctgacca ttagcggcac tcaggcggaa | 240 |
| gacgaagcgg attattattg cgcttcttgg gatactcttt ctgatgttga ggtgtttggc | 300 |
| ggcggcacga agttaaccgt tcttggccag | 330 |

<210> SEQ ID NO 16
<211> LENGTH: 330
<212> TYPE: DNA
<213> ORGANISM: Homo sapiens

<400> SEQUENCE: 16

| | |
|---|---|
| gatatcgaac tgacccagcc gccttcagtg agcgttgcac caggtcagac cgcgcgtatc | 60 |
| tcgtgtagcg gcgattctct tcgttcttat tttgtttctt ggtaccagca gaaacccggg | 120 |
| caggcgccag ttcttgtgat ttatgatgat gatgatcgtc cctcaggcat cccggaacgc | 180 |
| tttagcggat ccaacagcgg caacaccgcg accctgacca ttagcggcac tcaggcggaa | 240 |
| gacgaagcgg attattattg cgcttcttgg gatcctcctt ctgcttttga ggtgtttggc | 300 |
| ggcggcacga agttaaccgt tcttggccag | 330 |

<210> SEQ ID NO 17
<211> LENGTH: 327
<212> TYPE: DNA
<213> ORGANISM: Homo sapiens

<400> SEQUENCE: 17

| | |
|---|---|
| gatatcgaac tgacccagcc gccttcagtg agcgttgcac caggtcagac cgcgcgtatc | 60 |
| tcgtgtagcg gcgattctct tcgttcttat tttgtttctt ggtaccagca gaaacccggg | 120 |

```
caggcgccag ttcttgtgat ttatgatgat gatgatcgtc cctcaggcat cccggaacgc    180
tttagcggat ccaacagcgg caacaccgcg accctgacca ttagcggcac tcaggcggaa    240
gacgaagcgg attattattg cgcttcttgg gataatgatc attttgaggt gtttggcggc    300
ggcacgaagt taaccgttct tggccag                                       327

<210> SEQ ID NO 18
<211> LENGTH: 327
<212> TYPE: DNA
<213> ORGANISM: Homo sapiens

<400> SEQUENCE: 18
gatatcgaac tgacccagcc gccttcagtg agcgttgcac caggtcagac cgcgcgtatc     60
tcgtgtagcg gcgataagct tggttcttat tttgtttatt ggtaccagca gaaacccggg    120
caggcgccag ttcttgtgat ttatgatgat gataatcgtc cctcaggcat cccggaacgc    180
tttagcggat ccaacagcgg caacaccgcg accctgacca ttagcggcac tcaggcggaa    240
gacgaagcgg attattattg ccagtctttt ggtatttcta attttatgt gtttggcggc     300 ggcacgaagt taaccgttct tggccag                                       327

<210> SEQ ID NO 19
<211> LENGTH: 324
<212> TYPE: DNA
<213> ORGANISM: Homo sapiens

<400> SEQUENCE: 19
gatatcgaac tgacccagcc gccttcagtg agcgttgcac caggtcagac cgcgcgtatc     60
tcgtgtagcg gcgataagct tggttcttat tttgtttatt ggtaccagca gaaacccggg    120
caggcgccag ttcttgtgat ttatgatgat gataatcgtc cctcaggcat cccggaacgc    180
tttagcggat ccaacagcgg caacaccgcg accctgacca ttagcggcac tcaggcggaa    240
gacgaagcgg attattattg cggttcttgg gcttatcttg gtgatgtgtt tggcggcggc    300
acgaagttaa ccgttcttgg ccag                                          324

<210> SEQ ID NO 20
<211> LENGTH: 369
<212> TYPE: DNA
<213> ORGANISM: Homo sapiens

<400> SEQUENCE: 20
caggtgcaat tggttcagag cggcgcggaa gtgaaaaaac cgggcgaaag cctgaaaatt      60
agctgcaaag gttccggata ttcctttact aattatggta ttgcttgggt gcgccagatg    120
cctgggaagg gtctcgagtg gatgggcatt atctatccgt ctgatagcta taccaattat    180
tctccgagct ttcagggcca ggtgaccatt agcgcggata aaagcattag caccgcgtat    240
cttcaatgga gcagcctgaa agcgagcgat acggccatgt attattgcgc gcgtatgtct    300
tatgattatc agcatcaggc tccttctatg gattcttggg gccaaggcac cctggtgacg    360
gttagctca                                                           369

<210> SEQ ID NO 21
<211> LENGTH: 363
<212> TYPE: DNA
<213> ORGANISM: Homo sapiens
```

```
<400> SEQUENCE: 21
caggtgcaat tggttcagag cggcgcggaa gtgaaaaaac cgggcgcgag cgtgaaagtg    60
agctgcaaag cctccggata tacctttact ggttattata tgaattgggt ccgccaagcc   120
cctgggcagg gtctcgagtg gatgggcatt atcaatccgt ggactggcaa tacgaattac   180
gcgcagaagt ttcagggccg ggtgaccatg acccgtgata ccagcattag caccgcgtat   240
atggaactga gcagcctgcg tagcgaagat acggccgtgt attattgcgc gcgtgatcct   300 ggttttttt attatactcc ttctgatctt tggggccaag gcaccctggt gacggttagc   360
tca                                                                 363

<210> SEQ ID NO 22
<211> LENGTH: 363
<212> TYPE: DNA
<213> ORGANISM: Homo sapiens

<400> SEQUENCE: 22
caggtgcaat tggttcagag cggcgcggaa gtgaaaaaac cgggcgcgag cgtgaaagtg    60
agctgcaaag cctccggata tacctttact ggttattata tgaattgggt ccgccaagcc   120
cctgggcagg gtctcgagtg gatgggcatt attgatcctt ggaatggtca gactaattat   180
gctcagaagt ttcagggtcg ggtcaccatg acccgtgata ccagcattag caccgcgtat   240
atggaactga gcagcctgcg tagcgaagat acggccgtgt attattgcgc gcgtgatcct   300 ggttttttt attatactcc ttctgatctt tggggccaag gcaccctggt gacggttagc   360
tca                                                                 363

<210> SEQ ID NO 23
<211> LENGTH: 363
<212> TYPE: DNA
<213> ORGANISM: Homo sapiens

<400> SEQUENCE: 23
caggtgcaat tggttcagag cggcgcggaa gtgaaaaaac cgggcgcgag cgtgaaagtg    60
agctgcaaag cctccggata tacctttact ggttattata tgaattgggt ccgccaagcc   120
cctgggcagg gtctcgagtg gatgggcgtt attgatcctt ggaatggtat tactaattat   180
gctcagaagt ttcagggtcg ggtcaccatg acccgtgata ccagcattag caccgcgtat   240
atggaactga gcagcctgcg tagcgaagat acggccgtgt attattgcgc gcgtgatcct   300 ggttttttt attatactcc ttctgatctt tggggccaag gcaccctggt gacggttagc   360
tca                                                                 363

<210> SEQ ID NO 24
<211> LENGTH: 339
<212> TYPE: DNA
<213> ORGANISM: Homo sapiens

<400> SEQUENCE: 24
caggtgcaat tggttcagtc tggcgcggaa gtgaaaaaac cgggcagcag cgtgaaagtg    60
agctgcaaag cctccggagg cacttttttct tcttatgcta tttcttgggt gcgccaagcc   120
cctgggcagg gtctcgagtg gatgggcggt atcgatccgt ttggcactgc gaattacgcg   180
cagaagtttc agggccgggt gaccattacc gcggatgaaa gcaccagcac cgcgtatatg   240
gaactgagca gcctgcgtag cgaagatacg gccgtgtatt attgcgcgcg tgtttatcag   300
gatgtttggg gccaaggcac cctggtgacg gttagctca                          339
```

```
<210> SEQ ID NO 25
<211> LENGTH: 339
<212> TYPE: DNA
<213> ORGANISM: Homo sapiens

<400> SEQUENCE: 25
caggtgcaat tggttcagtc tggcgcggaa gtgaaaaaac cgggcagcag cgtgaaagtg      60
agctgcaaag cctccggagg cacttttttct tcttatgcta tttcttgggt gcgccaagcc    120
cctgggcagg gtctcgagtg gatgggcggt attgatccta ttatgggtac tgagtatgct    180
cagaagtttc agggtcgggt gaccattacc gcggatgaaa gcaccagcac cgcgtatatg    240
gaactgagca gcctgcgtag cgaagatacg gccgtgtatt attgcgcgcg tgtttatcag    300
gatgtttggg gccaaggcac cctggtgacg gttagctca                           339

<210> SEQ ID NO 26
<211> LENGTH: 342
<212> TYPE: DNA
<213> ORGANISM: Homo sapiens

<400> SEQUENCE: 26
caggtgcaat tggttcagtc tggcgcggaa gtgaaaaaac cgggcagcag cgtgaaagtg      60
agctgcaaag cctccggagg cacttttttct tcttatgcta tttcttgggt gcgccaagcc    120
cctgggcagg gtctcgagtg gatgggcgag attgatcctg ttattggtga gactgattat    180
gctcagaagt ttcagggtcg ggtgaccatt accgcggatg aaagcaccag caccgcgtat    240
atggaactga gcagcctgcg tagcgaagat acggccgtgt attattgcgc gcgtgtttat    300
caggatgttt ggggccaagg cacccctggtg acggttagct ca                      342

<210> SEQ ID NO 27
<211> LENGTH: 363
<212> TYPE: DNA
<213> ORGANISM: Homo sapiens

<400> SEQUENCE: 27
caggtgcaat tgcaagaaag tggtccgggc ctggtgaaac cgggcgaaac cctgagcctg      60
acctgcaccg tttccggagg tagcatttct tcttcttctt attattggaa ttggattcgc    120
caggcccctg gaagggtct cgagtggatt ggcgagatct attttggctg gacctattat    180
aatccgagcc tgaaaggccg ggtgaccatt agcgttgata cttcgaaaaa ccagtttagc    240
ctgaaactga gcagcgtgac ggcggaagat acggccgtgt attattgcgc gcgtggttat    300
gagtttcatg gttatactac ttttgattat tgggggccaag gcaccctggt gacggttagc    360
tca                                                                  363

<210> SEQ ID NO 28
<211> LENGTH: 348
<212> TYPE: DNA
<213> ORGANISM: Homo sapiens

<400> SEQUENCE: 28
caggtgcaat tggttcagag cggcgcggaa gtgaaaaaac cgggcgaaag cctgaaaatt      60
agctgcaaag gttccggata ttcctttttct aattattgga ttggttgggt gcgccagatg    120
cctgggaagg gtctcgagtg gatgggcttt atctttccgg atactagcta tacccgttat    180
tctccgagct ttcagggcca ggtgaccatt agcgcggata aaagcattag caccgcgtat    240
cttcaatgga gcagctgaa agcgagcgat acggccatgt attattgcgc gcgtgttaag    300
cttattactg attattgggg ccaaggcacc ctggtgacgg ttagctca                348
```

<210> SEQ ID NO 29
<211> LENGTH: 375
<212> TYPE: DNA
<213> ORGANISM: Homo sapiens

<400> SEQUENCE: 29

```
caggtgcaat tgcaacagtc tggtccgggc ctggtgaaac cgagccaaac cctgagcctg      60
acctgtgcga tttccggaga tagcgtgagc tctaattctg ctgcttgggg ttggattcgc     120
cagtctcctg ggcgtggcct cgagtggctg ggccgtatct attatcgtag caagtggggtt    180
aacgattatg cggtgagcgt gaaaagccgg attaccatca acccggatac ttcgaaaaac     240
cagtttagcc tgcaactgaa cagcgtgacc ccggaagata cggccgtgta ttattgcgcg     300
cgtcagggtg ctgtttatcc tggtccttat ggttttgatg tttggggcca aggcaccctg     360
gtgacggtta gctca                                                     375
```

<210> SEQ ID NO 30
<211> LENGTH: 336
<212> TYPE: DNA
<213> ORGANISM: Homo sapiens

<400> SEQUENCE: 30

```
gatatcgtgc tgacccagcc gccttcagtg agtggcgcac aggtcagcg tgtgaccatc       60
tcgtgtagcg gcagcagcag caacattggt tctaattatg tgatttggta ccagcagttg     120
cccgggacgg cgccgaaact tctgatttat gatgatacta atcgtccctc aggcgtgccg     180
gatcgtttta gcggatccaa aagcggcacc agcgcgagcc ttgcgattac gggcctgcaa     240
agcgaagacg aagcggatta ttattgctct acttatgata attatcaggc tggttgggtg     300
tttggcggcg gcacgaagtt aaccgttctt ggccag                              336
```

<210> SEQ ID NO 31
<211> LENGTH: 109
<212> TYPE: PRT
<213> ORGANISM: Homo sapiens

<400> SEQUENCE: 31

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Tyr Asp Ser Ser Met Leu Arg
                85                  90                  95

Val Phe Gly Gly Gly Thr Lys Leu Thr Val Leu Gly Gln
            100                 105
```

<210> SEQ ID NO 32
<211> LENGTH: 110
<212> TYPE: PRT
<213> ORGANISM: Homo sapiens -continued

<400> SEQUENCE: 32

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala Asn Tyr His Asp Ser
                85                  90                  95

Trp Val Phe Gly Gly Gly Thr Lys Leu Thr Val Leu Gly Gln
            100                 105                 110

<210> SEQ ID NO 33
<211> LENGTH: 110
<212> TYPE: PRT
<213> ORGANISM: Homo sapiens

<400> SEQUENCE: 33

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala Ser Asp Tyr Thr Ser
                85                  90                  95

Trp Val Phe Gly Gly Gly Thr Lys Leu Thr Val Leu Gly Gln
            100                 105                 110

<210> SEQ ID NO 34
<211> LENGTH: 110
<212> TYPE: PRT
<213> ORGANISM: Homo sapiens

<400> SEQUENCE: 34

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala His Tyr His Asp Ile
                85                  90                  95

Trp Val Phe Gly Gly Gly Thr Lys Leu Thr Val Leu Gly Gln
            100                 105                 110

-continued

```
<210> SEQ ID NO 35
<211> LENGTH: 109
<212> TYPE: PRT
<213> ORGANISM: Homo sapiens

<400> SEQUENCE: 35

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala His Asp Ser Leu Tyr Ser Arg
                85                  90                  95

Val Phe Gly Gly Gly Thr Lys Leu Thr Val Leu Gly Gln
            100                 105

<210> SEQ ID NO 36
<211> LENGTH: 114
<212> TYPE: PRT
<213> ORGANISM: Homo sapiens

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Asn His Pro His Thr Phe Gly Gln Gly Thr Lys Val Glu Ile Lys
            100                 105                 110

Arg Thr

<210> SEQ ID NO 37
<211> LENGTH: 113
<212> TYPE: PRT
<213> ORGANISM: Homo sapiens

<400> SEQUENCE: 37

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
    50                  55                  60
```

-continued

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Ala Phe Gly Trp Thr Phe Gly Gln Gly Thr Lys Val Glu Ile Lys Arg
            100                 105                 110

Thr

<210> SEQ ID NO 38
<211> LENGTH: 114
<212> TYPE: PRT
<213> ORGANISM: Homo sapiens

<400> SEQUENCE: 38

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Leu Gln Tyr
                85                  90                  95

Ser Asp Glu Pro Trp Thr Phe Gly Gln Gly Thr Lys Val Glu Ile Lys
            100                 105                 110

Arg Thr

<210> SEQ ID NO 39
<211> LENGTH: 114
<212> TYPE: PRT
<213> ORGANISM: Homo sapiens

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Ala Tyr Glu Pro Asn Thr Phe Gly Gln Gly Thr Lys Val Glu Ile Lys
            100                 105                 110

Arg Thr

<210> SEQ ID NO 40
<211> LENGTH: 114
<212> TYPE: PRT
<213> ORGANISM: Homo sapiens -continued

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Leu Gln Tyr
                85                  90                  95

Ala Phe Ser Pro Trp Thr Phe Gly Gln Gly Thr Lys Val Glu Ile Lys
            100                 105                 110

Arg Thr

<210> SEQ ID NO 41
<211> LENGTH: 108
<212> TYPE: PRT
<213> ORGANISM: Homo sapiens

<400> SEQUENCE: 41

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

Tyr Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Phe Pro Ser Ile Val
                85                  90                  95

Phe Gly Gly Gly Thr Lys Leu Thr Val Leu Gly Gln
            100                 105

<210> SEQ ID NO 42
<211> LENGTH: 108
<212> TYPE: PRT
<213> ORGANISM: Homo sapiens

<400> SEQUENCE: 42

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

Tyr Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ser Tyr Ile Phe Val
                85                  90                  95

Phe Gly Gly Gly Thr Lys Leu Thr Val Leu Gly Gln
            100                 105

<210> SEQ ID NO 43
<211> LENGTH: 108
<212> TYPE: PRT
<213> ORGANISM: Homo sapiens

<400> SEQUENCE: 43

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

Tyr Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Tyr Asp Ala Phe Thr Phe Val
                85                  90                  95

Phe Gly Gly Gly Thr Lys Leu Thr Val Leu Gly Gln
            100                 105

<210> SEQ ID NO 44
<211> LENGTH: 108
<212> TYPE: PRT
<213> ORGANISM: Homo sapiens

<400> SEQUENCE: 44

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Tyr Tyr Val
            20                  25                  30

Tyr Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Lys Tyr Val Phe Val
                85                  90                  95

Phe Gly Gly Gly Thr Lys Leu Thr Val Leu Gly Gln
            100                 105

<210> SEQ ID NO 45
<211> LENGTH: 110
<212> TYPE: PRT
<213> ORGANISM: Homo sapiens

<400> SEQUENCE: 45

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Arg Ser Tyr Phe Val
            20                  25                  30

Ser Trp Tyr Gln Gln Lys Pro Gly Gln Ala Pro Val Leu Val Ile Tyr
            35                  40                  45

Asp Asp Asp Asp Arg Pro Ser Gly Ile Pro Glu Arg Phe Ser Gly Ser
 50                      55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ser Trp Asp Thr Leu Ser Asp Val
                 85                  90                  95

Glu Val Phe Gly Gly Gly Thr Lys Leu Thr Val Leu Gly Gln
            100                 105                 110

<210> SEQ ID NO 46
<211> LENGTH: 110
<212> TYPE: PRT
<213> ORGANISM: Homo sapiens

<400> SEQUENCE: 46

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Arg Ser Tyr Phe Val
                 20                  25                  30

Ser Trp Tyr Gln Gln Lys Pro Gly Gln Ala Pro Val Leu Val Ile Tyr
            35                  40                  45

Asp Asp Asp Asp Arg Pro Ser Gly Ile Pro Glu Arg Phe Ser Gly Ser
 50                      55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ser Trp Asp Pro Pro Ser Ala Phe
                 85                  90                  95

Glu Val Phe Gly Gly Gly Thr Lys Leu Thr Val Leu Gly Gln
            100                 105                 110

<210> SEQ ID NO 47
<211> LENGTH: 109
<212> TYPE: PRT
<213> ORGANISM: Homo sapiens

<400> SEQUENCE: 47

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Arg Ser Tyr Phe Val
                 20                  25                  30

Ser Trp Tyr Gln Gln Lys Pro Gly Gln Ala Pro Val Leu Val Ile Tyr
            35                  40                  45

Asp Asp Asp Asp Arg Pro Ser Gly Ile Pro Glu Arg Phe Ser Gly Ser
 50                      55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ser Trp Asp Asn Asp His Phe Glu
                 85                  90                  95

Val Phe Gly Gly Gly Thr Lys Leu Thr Val Leu Gly Gln
            100                 105

<210> SEQ ID NO 48
<211> LENGTH: 109
<212> TYPE: PRT
<213> ORGANISM: Homo sapiens

<400> SEQUENCE: 48

Asp Ile Glu Leu Thr Gln Pro Pro Ser Val Ser Val Ala Pro Gly Gln
1               5                   10                  15

Thr Ala Arg Ile Ser Cys Ser Gly Asp Lys Leu Gly Ser Tyr Phe Val
            20                  25                  30

Tyr Trp Tyr Gln Gln Lys Pro Gly Gln Ala Pro Val Leu Val Ile Tyr
        35                  40                  45

Asp Asp Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Gly Ile Ser Asn Phe Tyr
                85                  90                  95

Val Phe Gly Gly Gly Thr Lys Leu Thr Val Leu Gly Gln
            100                 105

<210> SEQ ID NO 49
<211> LENGTH: 108
<212> TYPE: PRT
<213> ORGANISM: Homo sapiens

<400> SEQUENCE: 49

Asp Ile Glu Leu Thr Gln Pro Pro Ser Val Ser Val Ala Pro Gly Gln
1               5                   10                  15

Thr Ala Arg Ile Ser Cys Ser Gly Asp Lys Leu Gly Ser Tyr Phe Val
            20                  25                  30

Tyr Trp Tyr Gln Gln Lys Pro Gly Gln Ala Pro Val Leu Val Ile Tyr
        35                  40                  45

Asp Asp Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Ser Trp Ala Tyr Leu Gly Asp Val
                85                  90                  95

Phe Gly Gly Gly Thr Lys Leu Thr Val Leu Gly Gln
            100                 105

<210> SEQ ID NO 50
<211> LENGTH: 112
<212> TYPE: PRT
<213> ORGANISM: Homo sapiens

<400> SEQUENCE: 50

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ile Trp Tyr Gln Gln Leu Pro Gly Thr Ala Pro Lys Leu Leu
        35                  40                  45

Ile Tyr Asp Asp Thr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Thr Tyr Asp Asn Tyr Gln
                85                  90                  95

Ala Gly Trp Val Phe Gly Gly Gly Thr Lys Leu Thr Val Leu Gly Gln
            100                 105                 110

```
<210> SEQ ID NO 51
<211> LENGTH: 110
<212> TYPE: PRT
<213> ORGANISM: Homo sapiens

<400> SEQUENCE: 51

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala Asn Tyr His Asp Ser
                85                  90                  95

Trp Val Phe Gly Gly Gly Thr Lys Leu Thr Val Leu Gly Gln
            100                 105                 110

<210> SEQ ID NO 52
<211> LENGTH: 110
<212> TYPE: PRT
<213> ORGANISM: Homo sapiens

<400> SEQUENCE: 52

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala His Tyr His Asp Ile
                85                  90                  95

Trp Val Phe Gly Gly Gly Thr Lys Leu Thr Val Leu Gly Gln
            100                 105                 110

<210> SEQ ID NO 53
<211> LENGTH: 114
<212> TYPE: PRT
<213> ORGANISM: Homo sapiens

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80
```

```
Ser Ser Leu Gln Ala Glu Asp Val Ala Val Tyr Tyr Cys Gln Gln Tyr
            85                  90                  95

Ala Tyr Glu Pro Asn Thr Phe Gly Gln Gly Thr Lys Val Glu Ile Lys
            100                 105                 110

Arg Thr

<210> SEQ ID NO 54
<211> LENGTH: 114
<212> TYPE: PRT
<213> ORGANISM: Homo sapiens

<400> SEQUENCE: 54

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Phe Leu Gly Trp Tyr Gln Gln Lys Pro Gly Gln Pro
            35                  40                  45

Pro Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Leu Gln Tyr
            85                  90                  95

Ala Phe Ser Pro Trp Thr Phe Gly Gln Gly Thr Lys Val Glu Ile Lys
            100                 105                 110

Arg Thr

<210> SEQ ID NO 55
<211> LENGTH: 121
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
            35                  40                  45

Gly Ile Ile Asn Pro Trp Thr Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser
115                 120

<210> SEQ ID NO 56
<211> LENGTH: 121
<212> TYPE: PRT
<213> ORGANISM: Homo sapiens
```

-continued

```
<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Ile Ile Asp Pro Trp Asn Gly Gln Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser
115                 120

<210> SEQ ID NO 57
<211> LENGTH: 121
<212> TYPE: PRT
<213> ORGANISM: Homo sapiens

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Val Ile Asp Pro Trp Asn Gly Ile Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser
        115                 120

<210> SEQ ID NO 58
<211> LENGTH: 113
<212> TYPE: PRT
<213> ORGANISM: Homo sapiens

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Phe Gly Thr Ala Asn Tyr Ala Gln Lys Phe Gln
    50                  55                  60

Gly Arg Val Thr Ile Thr Ala Asp Glu Ser Thr Ser Thr Ala Tyr Met
65                  70                  75                  80
```

```
Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser
```

```
<210> SEQ ID NO 59
<211> LENGTH: 113
<212> TYPE: PRT
<213> ORGANISM: Homo sapiens

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Asp Pro Ile Met Gly Thr Glu Tyr Ala Gln Lys Phe Gln
        50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser
```

```
<210> SEQ ID NO 60
<211> LENGTH: 114
<212> TYPE: PRT
<213> ORGANISM: Homo sapiens

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Glu Ile Asp Pro Val Ile Gly Glu Thr Asp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Gln Asp Val Trp Gly Gln Gly Thr Leu Val Thr Val
            100                 105                 110

Ser Ser
```

```
<210> SEQ ID NO 61
<211> LENGTH: 121
<212> TYPE: PRT
<213> ORGANISM: Homo sapiens
```

```
<400> SEQUENCE: 61

Gln Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Ser Ser
            20                  25                  30

Ser Tyr Tyr Trp Asn Trp Ile Arg Gln Ala Pro Gly Lys Gly Leu Glu
        35                  40                  45

Trp Ile Gly Glu Ile Tyr Phe Gly Trp Thr Tyr Tyr Asn Pro Ser Leu
    50                  55                  60

Lys Gly Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Arg Gly Tyr Glu Phe His Gly Tyr Thr Thr Phe Asp Tyr Trp Gly
            100                 105                 110

Gln Gly Thr Leu Val Thr Val Ser Ser
        115                 120

<210> SEQ ID NO 62
<211> LENGTH: 116
<212> TYPE: PRT
<213> ORGANISM: Homo sapiens

<400> SEQUENCE: 62

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Phe Ile Phe Pro Asp Thr Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Lys Leu Ile Thr Asp Tyr Trp Gly Gln Gly Thr Leu Val
            100                 105                 110

Thr Val Ser Ser
        115

<210> SEQ ID NO 63
<211> LENGTH: 125
<212> TYPE: PRT
<213> ORGANISM: Homo sapiens

<400> SEQUENCE: 63

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Val Asn Asp Tyr Ala
    50                  55                  60

Val Ser Val Lys Ser Arg Ile Thr Ile Asn Pro Asp Thr Ser Lys Asn
65                  70                  75                  80
```

Gln Phe Ser Leu Gln Leu Asn Ser Val Thr Pro Glu Asp Thr Ala Val
                85                  90                  95

Tyr Tyr Cys Ala Arg Gln Gly Ala Val Tyr Pro Gly Pro Tyr Gly Phe
            100                 105                 110

Asp Val Trp Gly Gln Gly Thr Leu Val Thr Val Ser Ser
        115                 120                 125

<210> SEQ ID NO 64
<211> LENGTH: 123
<212> TYPE: PRT
<213> ORGANISM: Homo sapiens

<400> SEQUENCE: 64

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Gly Ile Ala Trp Val Arg Gln Met Pro Gly Lys Gly Leu Glu Trp Met
        35                  40                  45

Gly Ile Ile Tyr Pro Ser Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Ser Tyr Asp Tyr Gln His Gln Ala Pro Ser Met Asp Ser
            100                 105                 110

Trp Gly Gln Gly Thr Leu Val Thr Val Ser Ser
        115                 120

<210> SEQ ID NO 65
<211> LENGTH: 121
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Ile Ile Asn Pro Trp Thr Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Homo sapiens -continued

```
<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Ile Ile Asn Pro Trp Thr Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser
        115                 120

<210> SEQ ID NO 67
<211> LENGTH: 113
<212> TYPE: PRT
<213> ORGANISM: Homo sapiens

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Phe Gly Thr Ala Asn Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser

<210> SEQ ID NO 68
<211> LENGTH: 113
<212> TYPE: PRT
<213> ORGANISM: Homo sapiens

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
20                  25                  30

Ala Ile Ser Trp Val Arg Gln Ala Pro Gly Gln Gly Leu Glu Trp Met
35                  40                  45

Gly Gly Ile Asp Pro Phe Gly Thr Ala Asn Tyr Ala Gln Lys Phe Gln
50                  55                  60

Gly Arg Val Thr Ile Thr Ala Asp Glu Ser Thr Ser Thr Ala Tyr Met
65                  70                  75                  80
```

```
Glu Leu Ser Ser Leu Arg Ser Glu Asp Thr Ala Val Tyr Tyr Cys Ala
 85                  90                  95

Arg Val Tyr Gln Asp Val Trp Gly Gln Gly Thr Leu Val Thr Val Ser
100                 105                 110

Ser

<210> SEQ ID NO 69
<211> LENGTH: 121
<212> TYPE: PRT
<213> ORGANISM: Homo sapiens

<400> SEQUENCE: 69

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met Asn Trp Val Arg Gln Ala Pro Gly Gln Gly Leu Glu Trp Met
             35                  40                  45

Gly Ile Ile Asp Pro Trp Asn Gly Gln Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Pro Gly Phe Phe Tyr Tyr Thr Pro Ser Asp Leu Trp Gly
                100                 105                 110

Gln Gly Thr Leu Val Thr Val Ser Ser
            115                 120

<210> SEQ ID NO 70
<211> LENGTH: 121
<212> TYPE: PRT
<213> ORGANISM: Homo sapiens

<400> SEQUENCE: 70

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met Asn Trp Val Arg Gln Ala Pro Gly Gln Gly Leu Glu Trp Met
             35                  40                  45

Gly Ile Ile Asp Pro Trp Asn Gly Gln Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Pro Gly Phe Phe Tyr Tyr Thr Pro Ser Asp Leu Trp Gly
                100                 105                 110

Gln Gly Thr Leu Val Thr Val Ser Ser
            115                 120

<210> SEQ ID NO 71
<211> LENGTH: 113
<212> TYPE: PRT
<213> ORGANISM: Homo sapiens
```

```
<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Ile Met Gly Thr Glu Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser

<210> SEQ ID NO 72
<211> LENGTH: 113
<212> TYPE: PRT
<213> ORGANISM: Homo sapiens

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Ile Met Gly Thr Glu Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser

<210> SEQ ID NO 73
<211> LENGTH: 642
<212> TYPE: DNA
<213> ORGANISM: Homo sapiens

<400> SEQUENCE: 73
gatatcgaac tgacccagcc gccttcagtg agcgttgcac caggtcagac cgcgcgtatc      60
tcgtgtagcg gcgattctat tggtaataag tatgttcatt ggtaccagca gaaacccggg     120
caggcgccag ttcttgtgat ttatgctgat tctgatcgtc cctcaggcat cccggaacgc     180
tttagcggat ccaacagcgg caacaccgcg accctgacca ttagcggcac tcaggcggaa     240
gacgaagcgg attattattg ccagtcttat gctcattatc atgatatttg ggtgtttggc     300
ggcggcacga agttaaccgt cctaggtcag cccaaggctg ccccctcggt cactctgttc     360
ccgccctcct ctgaggagct tcaagccaac aaggccacac tggtgtgtct cataagtgac     420
ttctacccgg gagccgtgac agtggcctgg aaggcagata gcagccccgt caaggcggga     480
```

| | |
|---|---|
| gtggagacca ccacaccctc caaacaaagc aacaacaagt acgcggccag cagctatctg | 540 |
| agcctgacgc ctgagcagtg gaagtcccac agaagctaca gctgccaggt cacgcatgaa | 600 |
| gggagcaccg tggagaagac agtggcccct acagaatgtt ca | 642 |

<210> SEQ ID NO 74
<211> LENGTH: 660
<212> TYPE: DNA
<213> ORGANISM: Homo sapiens

<400> SEQUENCE: 74

| | |
|---|---|
| gatatcgtga tgacccagag cccggatagc ctggcggtga gcctgggcga acgtgcgacc | 60 |
| attaactgca gaagcagcca gtctattctt tatggtatta acaataattt tctgggttgg | 120 |
| taccagcaga aaccaggtca gccgccgaaa ctattaattt attgggcttc tactcgtgaa | 180 |
| agcggggtcc cggatcgttt tagcggctct ggatccggca ctgattttac cctgaccatt | 240 |
| tcgtccctgc aagctgaaga cgtggcggtg tattattgcc agcagtatgc ttatgagcct | 300 |
| aataccttg gccagggtac gaaagttgaa attaaacgta cggtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct caacagggg agagtgttag | 660 |

<210> SEQ ID NO 75
<211> LENGTH: 660
<212> TYPE: DNA
<213> ORGANISM: Homo sapiens

<400> SEQUENCE: 75

| | |
|---|---|
| gatatcgtga tgacccagag cccggatagc ctggcggtga gcctgggcga acgtgcgacc | 60 |
| attaactgca gaagcagcca gtctattctt tatggtatta acaataattt tctgggttgg | 120 |
| taccagcaga aaccaggtca gccgccgaaa ctattaattt attgggcttc tactcgtgaa | 180 |
| agcggggtcc cggatcgttt tagcggctct ggatccggca ctgattttac cctgaccatt | 240 |
| tcgtccctgc aagctgaaga cgtggcggtg tattattgcc ttcagtattc tgatgagcct | 300 |
| tggacctttg gccagggtac gaaagttgaa attaaacgta cggtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct caacagggg agagtgttag | 660 |

<210> SEQ ID NO 76
<211> LENGTH: 657
<212> TYPE: DNA
<213> ORGANISM: Homo sapiens

<400> SEQUENCE: 76

| | |
|---|---|
| gatatcgtga tgacccagag cccggatagc ctggcggtga gcctgggcga acgtgcgacc | 60 |
| attaactgca gaagcagcca gtctattctt tatggtatta acaataattt tctgggttgg | 120 |
| taccagcaga aaccaggtca gccgccgaaa ctattaattt attgggcttc tactcgtgaa | 180 |

| | | |
|---|---|---|
| agcggggtcc cggatcgttt tagcggctct ggatccggca ctgattttac cctgaccatt | 240 | |
| tcgtccctgc aagctgaaga cgtggcggtg tattattgcc agcagtatgc ttttggttgg | 300 | |
| acctttggcc agggtacgaa agttgaaatt aaacgtacgg tggctgcacc atctgtcttc | 360 | |
| atcttcccgc catctgatga gcagttgaaa tctggaactg cctctgttgt gtgcctgctg | 420 | |
| aataacttct atcccagaga ggccaaagta cagtggaagg tggataacgc cctccaatcg | 480 | |
| ggtaactccc aggagagtgt cacagagcag gacagcaagg acagcaccta cagcctcagc | 540 | |
| agcaccctga cgctgagcaa agcagactac gagaaacaca agtctacgc ctgcgaagtc | 600 | |
| acccatcagg gcctgagctc gcccgtcaca aagagcttca cagggggaga gtgttag | 657 | |

<210> SEQ ID NO 77
<211> LENGTH: 214
<212> TYPE: PRT
<213> ORGANISM: Homo sapiens

<400> SEQUENCE: 77

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala His Tyr His Asp Ile
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 78
<211> LENGTH: 214
<212> TYPE: PRT
<213> ORGANISM: Homo sapiens

<400> SEQUENCE: 78

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
            35                  40                  45

Ala Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Ala Asn Tyr His Asp Ser
                 85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
210

<210> SEQ ID NO 79
<211> LENGTH: 214
<212> TYPE: PRT
<213> ORGANISM: Homo sapiens

<400> SEQUENCE: 79

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
            35                  40                  45

Ala Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Ala Asn Tyr His Asp Ser
                 85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 80
<211> LENGTH: 214
<212> TYPE: PRT
<213> ORGANISM: Homo sapiens

<400> SEQUENCE: 80

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Asn Lys Tyr Val
            20                  25                  30

His Trp Tyr Gln Gln Lys Pro Gly Gln Ala Pro Val Leu Val Ile Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala His Tyr His Asp Ile
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 81
<211> LENGTH: 219
<212> TYPE: PRT
<213> ORGANISM: Homo sapiens

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

```
Ser Ser Leu Gln Ala Glu Asp Val Ala Val Tyr Tyr Cys Gln Gln Tyr
            85                  90                  95

Ala Tyr Glu Pro Asn Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 82
<211> LENGTH: 219
<212> TYPE: PRT
<213> ORGANISM: Homo sapiens

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
            35                  40                  45

Pro Lys Leu Leu Ile Tyr Trp Ala Ser Thr Arg Glu Ser Gly Val Pro
50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Leu Gln Tyr
            85                  90                  95

Ser Asp Glu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 83
<211> LENGTH: 218
<212> TYPE: PRT
<213> ORGANISM: Homo sapiens

<400> SEQUENCE: 83

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Ala Phe Gly Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 84
<211> LENGTH: 219
<212> TYPE: PRT
<213> ORGANISM: Homo sapiens

<400> SEQUENCE: 84

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Gly
            20                  25                  30

Ile Asn Asn Asn Phe Leu Gly Trp Tyr Gln Gln Lys Pro Gly Gln Pro
        35                  40                  45

Pro Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Leu Gln Tyr
                85                  90                  95

Ala Phe Ser Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

-continued

```
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 85
<211> LENGTH: 1347
<212> TYPE: DNA
<213> ORGANISM: Homo sapiens

<400> SEQUENCE: 85
caggtgcaat tggttcagag cggcgcggaa gtgaaaaaac cgggcgcgag cgtgaaagtg      60
agctgcaaag cctccggata tacctttact ggttattata tgaattgggt ccgccaagcc     120
cctgggcagg gtctcgagtg gatgggcatt atcaatccgt ggactggcaa tacgaattac     180
gcgcagaagt tcagggccg gtgaccatg acccgtgata ccagcattag caccgcgtat      240
atggaactga gcagcctgcg tagcgaagat acggccgtgt attattgcgc gcgtgatcct     300 ggttttttttt attatactcc ttctgatctt tggggccaag caccctggt gacggttagc     360 tcagcttcca ccaagggacc atccgtcttc cccctggcgc cctgctccag gagcacctcc     420
gagagcacag ccgccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtcccccatg cccatcatgc ccagcacctg agttcctggg gggaccatca     720
gtcttcctgt tccccccaaa acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca aagccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaga gcaatgggca gccggagaac aactacaaga ccacgcctcc cgtgctggac    1200
tccgacggct ccttcttcct ctacagcagg ctaaccgtgg acaagagcag gtggcaggag    1260
gggaatgtct tctcatgctc cgtgatgcat gaggctctgc acaaccacta cacacagaag    1320
agcctctccc tgtctctggg taaatga                                        1347

<210> SEQ ID NO 86
<211> LENGTH: 1323
<212> TYPE: DNA
<213> ORGANISM: Homo sapiens
```

<400> SEQUENCE: 86

```
caggtgcaat tggttcagtc tggcgcggaa gtgaaaaaac cgggcagcag cgtgaaagtg      60
agctgcaaag cctccggagg cacttttct tcttatgcta tttcttgggt gcgccaagcc     120
cctgggcagg gtctcgagtg gatgggcggt attgatccta ttatgggtac tgagtatgct     180
cagaagtttc agggtcgggt gaccattacc gcggatgaaa gcaccagcac cgcgtatatg     240
gaactgagca gcctgcgtag cgaagatacg gccgtgtatt attgcgcgcg tgtttatcag     300
gatgtttggg gccaaggcac cctggtgacg gttagctcag cttccaccaa gggaccatcc     360
gtcttccccc tggcgccctg ctccaggagc acctccgaga gcacagccgc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acgaagacct acacctgcaa cgtagatcac     600
aagcccagca acaccaaggt ggacaagaga gttgagtcca aatatggtcc cccatgccca     660
tcatgcccag cacctgagtt cctgggggga ccatcagtct tcctgttccc cccaaaaccc     720
aaggacactc tcatgatctc ccggacccct gaggtcacgt gcgtggtggt ggacgtgagc     780
caggaagacc ccgaggtcca gttcaactgg tacgtggatg gcgtggaggt gcataatgcc     840
aagacaaagc cgcgggagga gcagttcaac agcacgtacc gtgtggtcag cgtcctcacc     900
gtcctgcacc aggactggct gaacggcaag gagtacaagt gcaaggtctc caacaaaggc     960
ctcccgtcct ccatcgagaa aaccatctcc aaagccaaag gcagccccg agagccacag    1020
gtgtacaccc tgcccccatc ccaggaggag atgaccaaga accaggtcag cctgacctgc    1080
ctggtcaaag gcttctaccc cagcgacatc gccgtggagt gggagagcaa tgggcagccg    1140
gagaacaact acaagaccac gcctcccgtg ctggactccg acggctcctt cttcctctac    1200
agcaggctaa ccgtggacaa gagcaggtgg caggagggga atgtcttctc atgctccgtg    1260
atgcatgagg ctctgcacaa ccactacaca cagaagagcc tctccctgtc tctgggtaaa    1320
tga                                                                  1323
```

<210> SEQ ID NO 87
<211> LENGTH: 1323
<212> TYPE: DNA
<213> ORGANISM: Homo sapiens

<400> SEQUENCE: 87

```
caggtgcaat tggttcagtc tggcgcggaa gtgaaaaaac cgggcagcag cgtgaaagtg      60
agctgcaaag cctccggagg cacttttct tcttatgcta tttcttgggt gcgccaagcc     120
cctgggcagg gtctcgagtg gatgggcggt atcgatccgt ttggcactgc gaattacgcg     180
cagaagtttc agggccgggt gaccattacc gcggatgaaa gcaccagcac cgcgtatatg     240
gaactgagca gcctgcgtag cgaagatacg gccgtgtatt attgcgcgcg tgtttatcag     300
gatgtttggg gccaaggcac cctggtgacg gttagctcag cttccaccaa gggaccatcc     360
gtcttccccc tggcgccctg ctccaggagc acctccgaga gcacagccgc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acgaagacct acacctgcaa cgtagatcac     600
aagcccagca acaccaaggt ggacaagaga gttgagtcca aatatggtcc cccatgccca     660
```

| | |
|---|---|
| tcatgcccag cacctgagtt cctgggggga ccatcagtct tcctgttccc cccaaaaccc | 720 |
| aaggacactc tcatgatctc ccggacccct gaggtcacgt gcgtggtggt ggacgtgagc | 780 |
| caggaagacc ccgaggtcca gttcaactgg tacgtggatg gcgtggaggt gcataatgcc | 840 |
| aagacaaagc cgcgggagga gcagttcaac agcacgtacc gtgtggtcag cgtcctcacc | 900 |
| gtcctgcacc aggactggct gaacggcaag gagtacaagt gcaaggtctc caacaaaggc | 960 |
| ctcccgtcct ccatcgagaa aaccatctcc aaagccaaag gcagccccg agagccacag | 1020 |
| gtgtacaccc tgcccccatc ccaggaggag atgaccaaga accaggtcag cctgacctgc | 1080 |
| ctggtcaaag gcttctaccc cagcgacatc gccgtggagt gggagagcaa tgggcagccg | 1140 |
| gagaacaact acaagaccac gcctcccgtg ctggactccg acggctcctt cttcctctac | 1200 |
| agcaggctaa ccgtggacaa gagcaggtgg caggagggga atgtcttctc atgctccgtg | 1260 |
| atgcatgagg ctctgcacaa ccactacaca cagaagagcc tctccctgtc tctgggtaaa | 1320 |
| tga | 1323 |

<210> SEQ ID NO 88
<211> LENGTH: 1323
<212> TYPE: DNA
<213> ORGANISM: Homo sapiens

<400> SEQUENCE: 88

| | |
|---|---|
| caggtgcaat tggttcagtc tggcgcggaa gtgaaaaaac cgggcagcag cgtgaaagtg | 60 |
| agctgcaaag cctccggagg cactttttct tcttatgcta tttcttgggt gcgccaagcc | 120 |
| cctgggcagg gtctcgagtg gatgggcggt atcgatccgt ttggcactgc gaattacgcg | 180 |
| cagaagtttc agggccgggt gaccattacc gcggatgaaa gcaccagcac cgcgtatatg | 240 |
| gaactgagca gcctgcgtag cgaagatacg gccgtgtatt attgcgcgcg tgtttatcag | 300 |
| gatgtttggg gccaaggcac cctggtgacg gttagctcag cttccaccaa gggaccatcc | 360 |
| gtcttccccc tggcgccctg ctccaggagc acctccgaga gcacagccgc cctgggctgc | 420 |
| ctggtcaagg actacttccc cgaaccggtg acggtgtcgt ggaactcagg cgccctgacc | 480 |
| agcggcgtgc acaccttccc ggctgtccta cagtcctcag actctactc cctcagcagc | 540 |
| gtggtgaccg tgccctccag cagcttgggc acgaagacct acacctgcaa cgtagatcac | 600 |
| aagcccagca acaccaaggt ggacaagaga gttgagtcca aatatggtcc cccatgccca | 660 |
| tcatgcccag cacctgagtt cctgggggga ccatcagtct tcctgttccc cccaaaaccc | 720 |
| aaggacactc tcatgatctc ccggacccct gaggtcacgt gcgtggtggt ggacgtgagc | 780 |
| caggaagacc ccgaggtcca gttcaactgg tacgtggatg gcgtggaggt gcataatgcc | 840 |
| aagacaaagc cgcgggagga gcagttcaac agcacgtacc gtgtggtcag cgtcctcacc | 900 |
| gtcctgcacc aggactggct gaacggcaag gagtacaagt gcaaggtctc caacaaaggc | 960 |
| ctcccgtcct ccatcgagaa aaccatctcc aaagccaaag gcagccccg agagccacag | 1020 |
| gtgtacaccc tgcccccatc ccaggaggag atgaccaaga accaggtcag cctgacctgc | 1080 |
| ctggtcaaag gcttctaccc cagcgacatc gccgtggagt gggagagcaa tgggcagccg | 1140 |
| gagaacaact acaagaccac gcctcccgtg ctggactccg acggctcctt cttcctctac | 1200 |
| agcaggctaa ccgtggacaa gagcaggtgg caggagggga atgtcttctc atgctccgtg | 1260 |
| atgcatgagg ctctgcacaa ccactacaca cagaagagcc tctccctgtc tctgggtaaa | 1320 |
| tga | 1323 |

<210> SEQ ID NO 89
<211> LENGTH: 448
<212> TYPE: PRT
<213> ORGANISM: Homo sapiens

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Ile Ile Asn Pro Trp Thr Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

-continued

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445

<210> SEQ ID NO 90
<211> LENGTH: 440
<212> TYPE: PRT
<213> ORGANISM: Homo sapiens

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Ile Met Gly Thr Glu Tyr Ala Gln Lys Phe Gln
50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Ser Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

-continued

```
Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 91
<211> LENGTH: 440
<212> TYPE: PRT
<213> ORGANISM: Homo sapiens

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Phe Gly Thr Ala Asn Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Ser Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255
```

-continued

```
Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 92
<211> LENGTH: 440
<212> TYPE: PRT
<213> ORGANISM: Homo sapiens

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Phe Gly Thr Ala Asn Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190
```

```
Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Ser Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 93
<211> LENGTH: 448
<212> TYPE: PRT
<213> ORGANISM: Homo sapiens

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Ile Ile Asn Pro Trp Thr Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser Ala Ser Thr Lys Gly Pro Ser
        115                 120                 125
```

-continued

```
Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 94
<211> LENGTH: 448
<212> TYPE: PRT
<213> ORGANISM: Homo sapiens

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Ile Ile Asp Pro Trp Asn Gly Gln Thr Asn Tyr Ala Gln Lys Phe
    50                  55                  60
```

```
Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 95
<211> LENGTH: 448
<212> TYPE: PRT
<213> ORGANISM: Homo sapiens
```

```
<400> SEQUENCE: 95

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met Asn Trp Val Arg Gln Ala Pro Gly Gln Gly Leu Glu Trp Met
         35                  40                  45

Gly Ile Ile Asp Pro Trp Asn Gly Gln Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Pro Gly Phe Phe Tyr Tyr Thr Pro Ser Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415
```

-continued

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 96
<211> LENGTH: 440
<212> TYPE: PRT
<213> ORGANISM: Homo sapiens

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Asp Pro Ile Met Gly Thr Glu Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Val Tyr Gln Asp Val Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Ser Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

-continued

```
Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 97
<211> LENGTH: 127
<212> TYPE: PRT
<213> ORGANISM: Homo sapiens
<220> FEATURE:
<221> NAME/KEY: misc_feature
<222> LOCATION: (99)..(116)
<223> OTHER INFORMATION: Xaa can be any amino acid

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Xaa Xaa Trp Gly Gln Gly Thr Leu Val Thr Val Ser Ser
        115                 120                 125

<210> SEQ ID NO 98
<211> LENGTH: 127
<212> TYPE: PRT
<213> ORGANISM: Homo sapiens
<220> FEATURE:
<221> NAME/KEY: misc_feature
<222> LOCATION: (99)..(116)
<223> OTHER INFORMATION: Xaa can be any amino acid

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Ser Leu Arg Ser Glu Asp Thr Ala Val Tyr Tyr Cys
            85                  90                  95

Ala Arg Xaa Xaa Xaa Xaa Xaa Xaa Xaa Xaa Xaa Xaa Xaa Xaa
            100                 105                 110

Xaa Xaa Xaa Xaa Trp Gly Gln Gly Thr Leu Val Thr Val Ser Ser
        115                 120                 125
```

<210> SEQ ID NO 99
<211> LENGTH: 126
<212> TYPE: PRT
<213> ORGANISM: Homo sapiens
<220> FEATURE:
<221> NAME/KEY: misc_feature
<222> LOCATION: (98)..(115)
<223> OTHER INFORMATION: Xaa can be any amino acid

<400> SEQUENCE: 99

```
Gln Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Ala Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Glu Asp Thr Ala Val Tyr Tyr Cys Ala
                85                  90                  95

Arg Xaa Xaa Xaa Xaa Xaa Xaa Xaa Xaa Xaa Xaa Xaa Xaa Xaa
            100                 105                 110

Xaa Xaa Xaa Trp Gly Gln Gly Thr Leu Val Thr Val Ser Ser
        115                 120                 125
```

<210> SEQ ID NO 100
<211> LENGTH: 127
<212> TYPE: PRT
<213> ORGANISM: Homo sapiens
<220> FEATURE:
<221> NAME/KEY: misc_feature
<222> LOCATION: (99)..(116)
<223> OTHER INFORMATION: Xaa can be any amino acid

<400> SEQUENCE: 100

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Xaa Xaa Xaa Xaa Xaa Xaa Xaa Xaa Xaa Xaa Xaa Xaa Xaa
            100                 105                 110

Xaa Xaa Xaa Xaa Trp Gly Gln Gly Thr Leu Val Thr Val Ser Ser
        115                 120                 125
```

```
<210> SEQ ID NO 101
<211> LENGTH: 130
<212> TYPE: PRT
<213> ORGANISM: Homo sapiens
<220> FEATURE:
<221> NAME/KEY: misc_feature
<222> LOCATION: (102)..(119)
<223> OTHER INFORMATION: Xaa can be any amino acid

<400> SEQUENCE: 101

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Xaa Xaa Xaa Xaa Xaa Xaa Xaa Xaa Xaa Xaa Xaa
            100                 105                 110

Xaa Xaa Xaa Xaa Xaa Xaa Xaa Trp Gly Gln Gly Thr Leu Val Thr Val
        115                 120                 125

Ser Ser
130

<210> SEQ ID NO 102
<211> LENGTH: 112
<212> TYPE: PRT
<213> ORGANISM: Homo sapiens
<220> FEATURE:
<221> NAME/KEY: misc_feature
<222> LOCATION: (90)..(99)
<223> OTHER INFORMATION: Xaa can be any amino acid

<400> SEQUENCE: 102

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Xaa Xaa Xaa Xaa Xaa Xaa Xaa
                85                  90                  95

Xaa Xaa Xaa Val Phe Gly Gly Gly Thr Lys Leu Thr Val Leu Gly Gln
            100                 105                 110

<210> SEQ ID NO 103
<211> LENGTH: 110
<212> TYPE: PRT
<213> ORGANISM: Homo sapiens
<220> FEATURE:
<221> NAME/KEY: misc_feature
<222> LOCATION: (88)..(97)
<223> OTHER INFORMATION: Xaa can be any amino acid
```

```
<400> SEQUENCE: 103

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Xaa Xaa Xaa Xaa Xaa Xaa Xaa Xaa
                85                  90                  95

Xaa Val Phe Gly Gly Thr Lys Leu Thr Val Leu Gly Gln
            100                 105                 110

<210> SEQ ID NO 104
<211> LENGTH: 115
<212> TYPE: PRT
<213> ORGANISM: Homo sapiens
<220> FEATURE:
<221> NAME/KEY: misc_feature
<222> LOCATION: (95)..(102)
<223> OTHER INFORMATION: Xaa can be any amino acid

<400> SEQUENCE: 104

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Xaa Xaa
                85                  90                  95

Xaa Xaa Xaa Xaa Xaa Thr Phe Gly Gln Gly Thr Lys Val Glu Ile
            100                 105                 110

Lys Arg Thr
        115
```

What is claimed is:

1. An isolated human or humanized antibody or functional fragment thereof comprising an antigen-binding region that is specific for target protein c-Met, wherein the antibody or functional fragment thereof binds to c-Met, and wherein the sequence of the antibody or functional fragment thereof comprises:

the sequences of CDR1, CDR2 and CDR3 of heavy chain 4687, wherein the sequences of CDR1, CDR2, and CDR3 of heavy chain 4687 are residues 26-35, 50-65, and 98-102, respectively, of SEQ ID NO: 58; and the sequences of CDR1, CDR2, and CDR3 of light chain 5097, wherein the sequences of CDR1, CDR2, and CDR3 of light chain 5097 are residues 24-39, 55-61, and 94-100 of SEQ ID NO: 37.

2. The antibody or functional fragment thereof according to claim 1, wherein the antibody or functional fragment thereof binds the target protein c-Met with a $K_D$ of $2.0 \times 10^{-5}$ M or less, $2.0 \times 10^{-6}$ M or less, $2.0 \times 10^{-7}$ M or less, $2.0 \times 10^{-8}$ M or less, and $2.0 \times 10^{-9}$ M or less.

3. The antibody or functional fragment thereof according to claim 1, wherein the antibody or functional fragment thereof has an off rate ($K_{off}$) for target protein c-Met of $1.0 \times 10^{-2}$ per sec or smaller, $1.0 \times 10^{-3}$ per sec or smaller, $1 \times 10^{-4}$ per sec or smaller or $1.0 \times 10^{-5}$ per sec or smaller.

4. The antibody or functional fragment thereof according to claim 1, wherein the antibody or functional fragment thereof binds the target protein c-Met with a $K_D$ of $2.0 \times 10^{-5}$ M or less, $2.0 \times 10^{-6}$ M or less, $2.0 \times 10^{-7}$ M or less, $2.0 \times 10^{-8}$ M or less, and $2.0 \times 10^{-9}$ M or less, and inhibits HGF binding to c-Met.

5. The antibody or functional fragment thereof according to claim 1, wherein the antibody or functional fragment thereof binds the target protein c-Met and modulates c-Met phosphorylation.

6. The antibody or functional fragment thereof according to claim 5, wherein activating c-Met phosphorylation stimulates at least one of an activity selected from the group of organ regeneration, wound healing, and tissue regeneration.

7. The antibody or functional fragment thereof according to claim 6, wherein the organ is selected from the group of kidney, liver, pancreas, heart, lung, intestine, skin, thymus, and thyroid.

8. The antibody according to claim 1, wherein binding of the antibody to c-Met is determined by at least one assay selected from an amount of antagonism or agonism of: ligand induction of a c-Met signal transduction pathway enzyme activity; ligand induction of a c-Met signal transduction pathway gene expression; electrochemiluminescence-based binding of a ligand to c-Met; enzyme-linked immunosorbent assay of binding of a ligand to c-Met; and proliferation, survival, migration or metastasis of a cell.

9. An isolated functional fragment according to claim 1.

10. An isolated amino acid sequence that binds to and is specific for target protein c-Met comprising CDR1, CDR2 and CDR3 sequences of the heavy and light chains of an antigen-binding region that is specific for target protein c-Met, wherein the CDR1, CDR2 and CDR3 of the heavy and light chains are encoded by nucleotides 78-105, 150-195, and 294-306, respectively, of SEQ ID NO:24 and nucleotides 72-117, 165-183, and 282-300, respectively, of SEQ ID NO:7.

11. The isolated amino acid sequence of claim 10 comprising an antigen-binding region, said region comprising a light chain encoded by a nucleotide sequence of SEQ ID NO: 7.

12. The isolated amino acid sequence of claim 10 comprising an antigen-binding region, said region comprising a heavy chain encoded by a nucleotide sequence of SEQ ID NO: 24.

13. An isolated amino acid sequence comprising CDR1, CDR2 and CDR3 sequences of a light chain and a heavy chain of an antigen-binding region that is specific for target protein c-Met, wherein the CDR sequences from the heavy chain are:
CDR1=GGTFSSYAIS (residues 26-35 of SEQ ID NO: 58)
CDR2=GIDPFGTANYAQKFQG (residues 50-65 of SEQ ID NO: 58)
CDR3=VYQDV (residues 98-102 of SEQ ID NO: 58), and
the CDR sequences from the light chain are:
CDR1=RSSQSILYGINNNFLG (residues 24-39 of SEQ ID NO: 37)
CDR2=WASTRES (residues 55-61 of SEQ ID NO: 37)
CDR3=QQYAFGW (residues 94-100 of SEQ ID NO: 37).

14. The isolated antibody according to claim 1, which is an IgG.

15. The isolated antibody according to claim 14, which is an IgG1, an IgG2, an IgG3 or an IgG4.

16. The isolated antibody or functional fragment according to claim 1 that is a Fab or scFv antibody fragment.

17. The isolated antibody or functional fragment thereof according to claim 1, comprising an antigen-binding region that is specific for an epitope of c-Met, wherein the epitope is a conformational epitope.

18. The isolated antibody or functional fragment thereof according to claim 17 wherein the conformational epitope comprises residues of an amino acid sequence of an extracellular domain of c-Met.

19. A pharmaceutical composition comprising at least one antibody or functional fragment according to claim 1 and a pharmaceutically acceptable carrier or excipient therefore.

20. A human or humanized antibody or antibody fragment thereof as described in claim 1, wherein the antibody is a synthetic antibody.

21. The pharmaceutical composition according to claim 19, further comprising an additional therapeutic agent.

22. The pharmaceutical composition according to claim 21, wherein the additional therapeutic agent is selected from the group consisting of an anti-cancer agent; an antibiotic; an anti-inflammatory agent; a growth factor; and a cytokine.

23. An immunoconjugate comprising a first component which is an antibody or fragment thereof according to claim 1.

24. The immunoconjugate according to claim 23, comprising a second component having a second amino acid sequence.

25. The immunoconjugate according to claim 24, further comprising a cytotoxin.

26. The immunoconjugate according to claim 24, wherein the second component is a binding protein or antibody having a binding specificity for a target that is different from c-Met.

27. A bispecific antibody comprising an immunoconjugate comprising a first component comprising a functional fragment according to claim 1.

28. The bispecific antibody according to claim 27, wherein the target of the binding specificity different from c-Met is a tumor antigen or tumor-associated protein on a surface of a cancer cell.

29. A kit comprising an antibody or fragment thereof according to claim 1.

30. The kit according to claim 29, further comprising a pharmaceutically acceptable carrier or excipient therefore.

31. The kit according to claim 29 wherein the antibody is present in a unit dose and further comprising instructions for use in administering to a subject.

* * * * *